US012186265B2

(12) United States Patent
Vaughn et al.

(10) Patent No.: US 12,186,265 B2
(45) Date of Patent: Jan. 7, 2025

(54) ISOLATION SYSTEM

(71) Applicant: NUMOTECH, INC., Northridge, CA (US)

(72) Inventors: Mark Roy Vaughn, Albuquerque, NM (US); Alva Keith Miller, Albuquerque, NM (US); Joseph Alexander Sember, III, Chatsworth, CA (US); Robert Michael Felton, Northridge, CA (US)

(*) Notice: Subject to any disclaimer, the term of this patent is extended or adjusted under 35 U.S.C. 154(b) by 888 days.

(21) Appl. No.: 17/338,877

(22) Filed: Jun. 4, 2021

(65) Prior Publication Data
US 2021/0386947 A1    Dec. 16, 2021

Related U.S. Application Data

(60) Provisional application No. 63/038,943, filed on Jun. 15, 2020.

(51) Int. Cl.
A61G 10/00    (2006.01)
A61J 1/10    (2006.01)
A61M 16/00    (2006.01)

(52) U.S. Cl.
CPC ............ *A61J 1/10* (2013.01); *A61G 10/00* (2013.01); *A61M 16/00* (2013.01); *A61M 2202/0208* (2013.01)

(58) Field of Classification Search
CPC .... A61M 21/0094; A62B 31/00; A61B 90/40; A61B 2090/401
See application file for complete search history.

(56) References Cited

U.S. PATENT DOCUMENTS

| 3,602,221 | A | 8/1971 | Bleicken |
| 5,865,722 | A | 2/1999 | Heng |
| 5,950,625 | A * | 9/1999 | Bongiovanni ......... A61B 90/40 128/845 |
| 6,241,653 | B1 | 6/2001 | Gauger et al. |
| 6,321,746 | B1 | 11/2001 | Schneider et al. |
| 6,321,764 | B1 | 11/2001 | Gauger et al. |
| 6,461,290 | B1 | 10/2002 | Reichman et al. |
| 7,137,736 | B2 | 11/2006 | Pawloski et al. |
| 7,520,277 | B1 | 4/2009 | Grady |
| 2002/0112754 | A1* | 8/2002 | Gauger ............... A61G 1/0293 135/128 |

(Continued)

FOREIGN PATENT DOCUMENTS

CN    111297587 A  *  6/2020
DE    202019104175 U1  *  12/2019

(Continued)

OTHER PUBLICATIONS

PCT/US2021/036372; Notification of Transmittal of ISR and Written Opinion; Date: Oct. 25, 2021.

(Continued)

*Primary Examiner* — Thaddeus B Cox
(74) *Attorney, Agent, or Firm* — Patent Law Agency, LLC; Peter Ganjian

(57) ABSTRACT

The present invention discloses an isolation system, comprising a flexible, portable, disposable membrane with no rigid structures. The membrane inflates from a contracted state having a small form-factor for storage to an inflated state for use. The membrane has an opening on one side defining a chamber within, with the opening having a sealing member that when closed, seals off the chamber. The membrane includes a first port for ingress of gas into the chamber a second port for egress of exhaust gas via an associated exhaust filter assembly, with the second port intrinsically functioning as a passive pressure regulator.

22 Claims, 57 Drawing Sheets

(56) References Cited

U.S. PATENT DOCUMENTS

| | | | |
|---|---|---|---|
| 2004/0074529 A1 | 4/2004 | Levey et al. | |
| 2004/0154616 A1 | 8/2004 | Parker Risley et al. | |
| 2004/0261796 A1* | 12/2004 | Butler | A61G 10/026 |
| | | | 128/205.26 |
| 2005/0251084 A1 | 11/2005 | Rosati | |
| 2006/0041994 A1* | 3/2006 | Germain | A41D 13/002 |
| | | | 2/457 |
| 2006/0185670 A1 | 8/2006 | Loori et al. | |
| 2008/0058735 A1 | 3/2008 | Rosati | |
| 2009/0048555 A1 | 2/2009 | Stryker et al. | |
| 2009/0120433 A1 | 5/2009 | Loori et al. | |
| 2016/0074268 A1 | 3/2016 | Breegi et al. | |
| 2021/0338509 A1* | 11/2021 | Clendenin | A61G 10/005 |
| 2022/0192780 A1* | 6/2022 | Okajima | A61B 90/40 |

FOREIGN PATENT DOCUMENTS

| | | |
|---|---|---|
| GB | 1027114 | 4/1966 |
| WO | WO20020022069 | 3/2002 |
| WO | WO2002004073 A3 | 9/2002 |

OTHER PUBLICATIONS

A guideline to limit indoor airborne transmission of COVID-19; Bazant et al.; Department of Chemical Engineering, Massachusetts Institute of Technology, Edited by Renyi Zhang, Texas A&M University, and accepted by Editorial Board Member John H. Seinfeld Mar. 3, 2021; PNAS 2021 vol. 118 No. 17 e2018995118; https://doi.org/10.1073/pnas.2018995118.

https://www.engineersedge.com/fluid_flow/pressure_drop/pressure_drop.htm; Teaches Determining Fluid Pressure Drop Along Pipe Length of Uniform Diateter; Last Visited Jun. 4, 2021.

https://www.tri-anim.com/oxygen-flowmeters-chrome-body-group-33486-3708.aspx?search=715-D1MFA1006L; Tri-Anim; TEE Branch for Oxygen Flowmeters; Last Visited Jun. 4, 2021.

European Patent Office Communications Including Supplementary European Search Repor, Annex to the European Serach Report, and Invitation to Reply—Jun. 6, 2024.

* cited by examiner

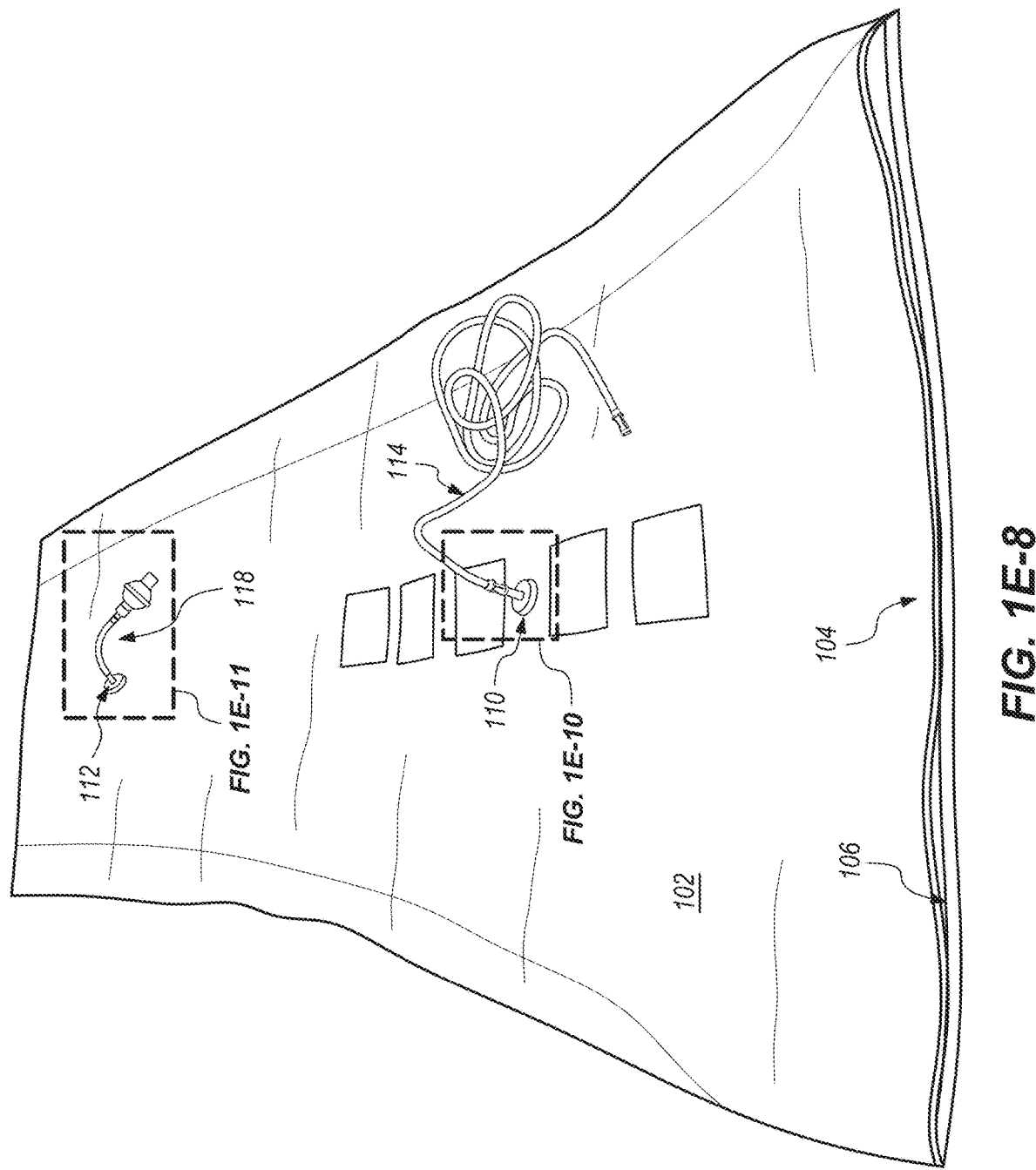

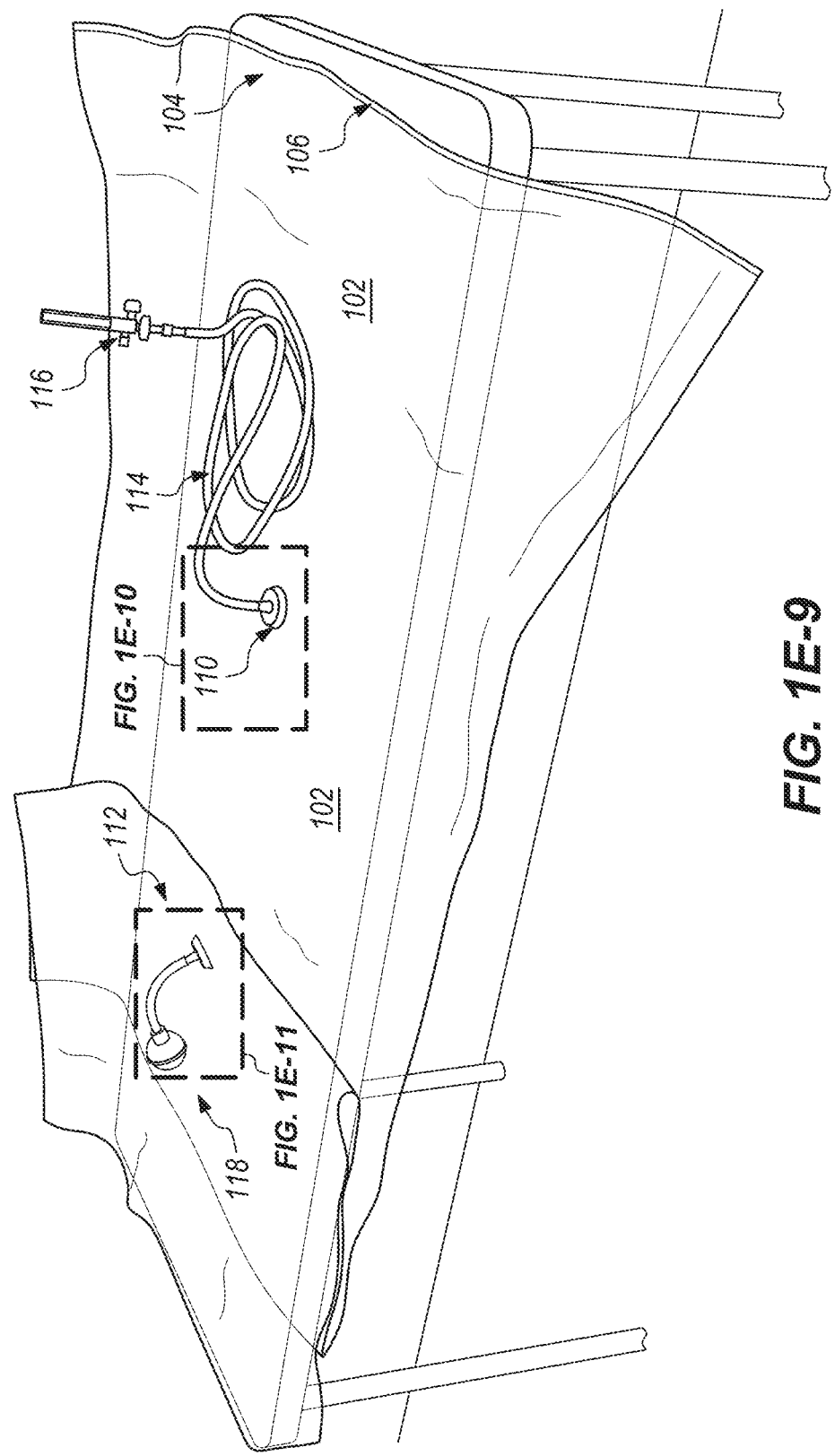

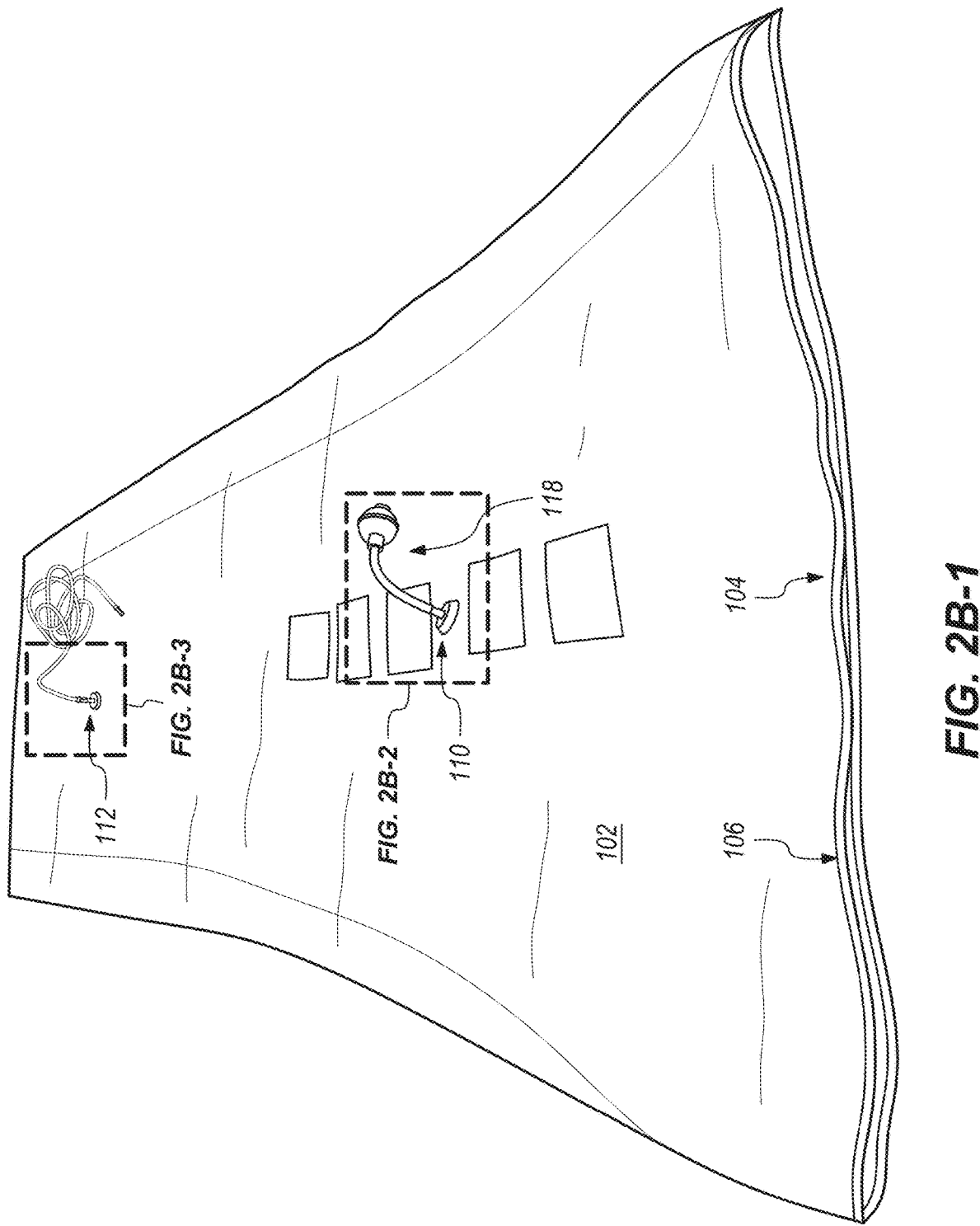

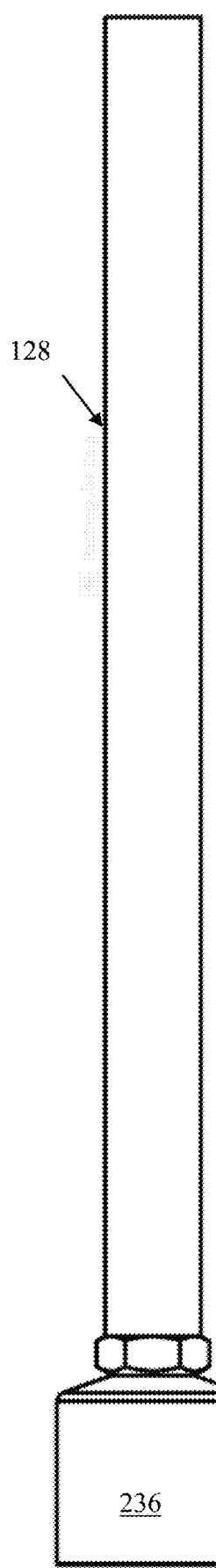
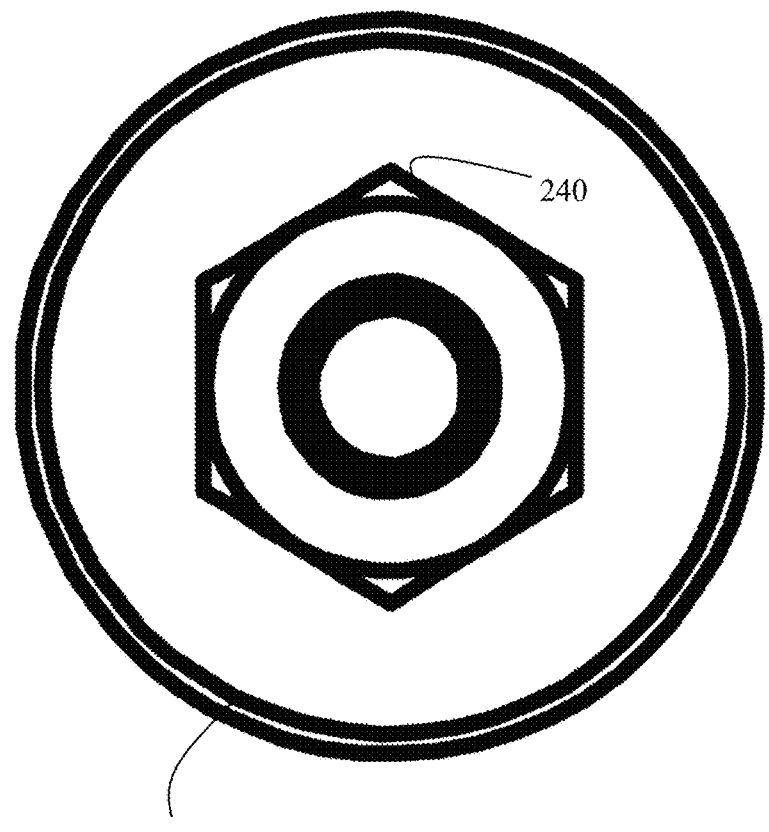
FIG. 5E
FIG. 5D

ISOLATION SYSTEM

CROSS-REFERENCE TO RELATED APPLICATIONS

This application claims the benefit of priority of co-pending U.S. Utility Provisional Patent Application 63/038,943, filed 15 Jun. 2020, the entire disclosure of which is expressly incorporated by reference in its entirety herein.

All documents mentioned in this specification are herein incorporated by reference to the same extent as if each individual document was specifically and individually indicated to be incorporated by reference.

It should be noted that throughout the disclosure, where a definition or use of a term in any incorporated document(s) is inconsistent or contrary to the definition of that term provided herein, the definition of that term provided herein applies and the definition of that term in the incorporated document(s) does not apply.

BACKGROUND OF THE INVENTION

Field of the Invention

One or more embodiments of the present invention relate to a positive pressure-based isolation system and more particularly, to an isolation system that is disposable and has compact form factor for storage and portability.

Description of Related Art

Conventional isolation apparatuses are well known and have been in use for a number of years. Regrettably, most conventional isolation apparatuses are not disposable and further, require complex rigid structures to maintain their form during use and hence, they are not self-supporting.

Additionally, most conventional isolation apparatuses that do use rigid members for support, do not have a small form factor when not used for a more efficient storage.

Still other conventional isolation apparatuses may not be compatible for applications that use medical grade oxygen, and most others are not considered as true isolation apparatuses since they do not fully encompass or encapsulate a subject.

As importantly, most other conventional isolation apparatuses use well-known ventilation systems that generate and maintain a negative pressure within a room or chamber for example, for isolation. Most such negative pressure systems require extremely complex and costly additional components to continuously generate and maintain the required negative pressure for isolation. In most instances, most isolation apparatuses using negative pressure systems are not disposable (i.e., one time use) due to their very high costs and types of non-disposable components used.

Accordingly, in light of the current state of the art and the drawbacks to current isolation apparatuses, a need exists for an isolation system that would be portable, disposable, have no rigid structural supports, have a small form-factor when not used and compatible for applications that use medical grade oxygen. Further, a need exists for an isolation system that would also not use, need, or require negative pressure for isolation.

BRIEF SUMMARY OF THE INVENTION

A non-limiting, exemplary aspect of an embodiment of the present invention provides an isolation system, comprising:

a flexible, portable, disposable membrane with no rigid structures comprised of a medical grade polymer;
the membrane expands from a contracted state having a small form-factor for storage to an expanded state for use;
the membrane has an opening on one side defining a chamber;
the opening has a sealing member that when closed, seals off the chamber;
the membrane includes:
an inlet port for ingress of oxygen, compressed air, or air enriched with oxygen into the chamber; and
an outlet port for egress of exhaust gases via an associated exhaust filter assembly, with the outlet port intrinsically functioning as a passive pressure regulator.

Another non-limiting, exemplary aspect of an embodiment of the present invention provides an isolation system, comprising:

a flexible, portable, disposable membrane with no rigid structures;
the membrane inflates from a contracted state having a small form-factor for storage to an inflated state for use;
the membrane has an opening on one side defining a chamber;
the opening has a sealing member that when closed, seals off the chamber;
the membrane includes:
a first port for ingress of gas into the chamber; and
a second port for egress of exhaust gases via an associated exhaust filter assembly.

Still, another non-limiting, exemplary aspect of an embodiment of the present invention provides A method for isolation, comprising:

providing a disposable isolation kit;
unfurling a membrane of the disposable isolation kit;
surrounding a subject within the membrane;
laying subject prone while within the membrane;
aligning a first port and a second port of the membrane to lie approximate on the frontal midplane of the subject;
connecting medical grade oxygen tubing to a first (or inlet) port of the membrane;
connecting exhaust filter assembly to a second port of the membrane;
delivering medical grade oxygen, air, or air enriched with oxygen into the membrane at a rate regulated to control internal pressure of the membrane to maintain the membrane in the expanded state;
sealing an open end of membrane;
maintaining visual observation to assure inflow of continuous unabated medical grade oxygen, air, or air enriched with oxygen.

These and other features and aspects of the invention will be apparent to those skilled in the art from the following detailed description of preferred non-limiting exemplary embodiments, taken together with the drawings and the claims that follow.

BRIEF DESCRIPTION OF THE DRAWINGS

It is to be understood that the drawings are to be used for the purposes of exemplary illustration only and not as a definition of the limits of the invention. Throughout the disclosure, the word "exemplary" may be used to mean "serving as an example, instance, or illustration," but the absence of the term "exemplary" does not denote a limiting embodiment. Any embodiment described as "exemplary" is not necessarily to be construed as preferred or advantageous over other embodiments. In the drawings, like reference character(s) present corresponding part(s) throughout.

FIG. 1A to 1E-11 are non-limiting, exemplary illustrations of an isolation system packaging, which progressively illustrate a non-limiting, exemplary method for unpacking the same in accordance with one or more embodiments of the present invention;

FIGS. 2A-1 to 2A-13 and 2B-1 to 2B-7, are non-limiting, exemplary illustrations of the isolation system shown in FIG. 1A to 1E-11, progressively illustrating a non-limiting, exemplary methods for fully sealing and isolating a patient in accordance with one or more embodiments of the present invention;

FIGS. 5A-1 to 5I-3 are non-limiting, exemplary illustrations of an exhaust filter assembly shown in FIGS. 1A to 4V in accordance with one or more embodiments of the present invention.

DETAILED DESCRIPTION OF THE INVENTION

Figure 1A:
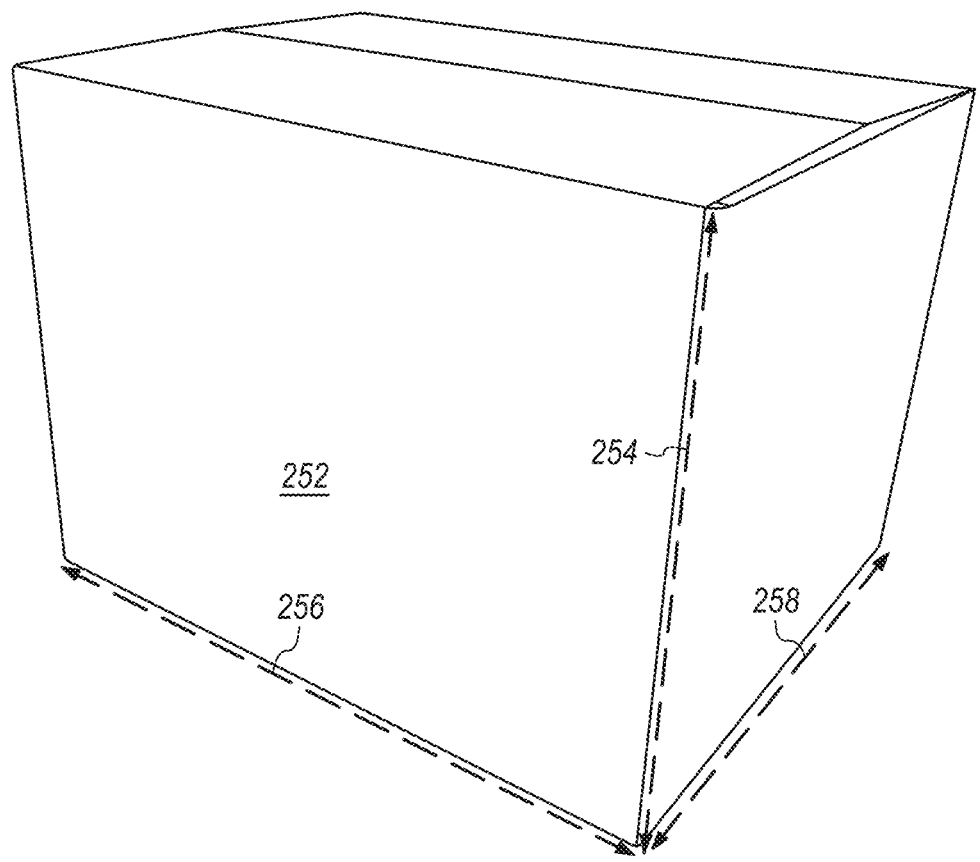

The detailed description set forth below in connection with the appended drawings is intended as a description of presently preferred embodiments of the invention and is not intended to represent the only forms in which the present invention may be constructed and or utilized.

It is to be appreciated that certain features of the invention, which are, for clarity, described in the context of separate embodiments, may also be provided in combination in a single embodiment. Conversely, various features of the invention that are, for brevity, described in the context of a single embodiment may also be provided separately or in any suitable sub-combination or as suitable in any other described embodiment of the invention. Stated otherwise, although the invention is described below in terms of various exemplary embodiments and implementations, it should be understood that the various features and aspects described in one or more of the individual embodiments are not limited in their applicability to the particular embodiment with which they are described, but instead can be applied, alone or in various combinations, to one or more of the other embodiments of the invention.

One or more embodiments of the present invention define the phrase "medical grade" in accordance with its ordinary meaning in the medical art. For example, a medical grade matter or material are those that are biocompatible to living systems.

One or more embodiments of the present invention may use the phrase "form factor" as the physical size and or shape of various members and or components of the one or more embodiments of the isolation system of the present invention.

Throughout the disclosure the term oxygen, medical grade oxygen, air, and or air enriched with oxygen may be used interchangeably or concurrently as the isolation system is fully compatible with all such sources for medical use.

One or more embodiments of the present invention provide an isolation system that is lightweight and portable.

One or more embodiments of the present invention provide an isolation system that has a small form-factor when not used for easy storage.

One or more embodiments of the present invention provide an isolation system that is disposable.

One or more embodiments of the present invention provide an isolation system that is self-supporting with no rigid structural supports.

One or more embodiments of the present invention provide an isolation system that is compatible for applications that use medical grade oxygen.

One or more embodiments of the present invention provide an isolation system that when in an expanded state, fully encompass or encapsulate a subject.

One or more embodiments of the present invention provide an isolation system that does not use, need, or require negative pressure for isolation, but instead, uses positive pressure for isolation of subjects.

Positive pressure systems in accordance with one or more embodiments of the present invention do not require extensive internal support structures, are low cost and disposable. That is, one or more embodiments of the positive pressure isolation system of the present invention are less expensive by at least a factor of ten, not accounting for the cost burden of thorough cleaning that is required for the non-disposable negative pressure systems.

Further, one or more embodiments of the positive pressure isolation system of the present invention may be flexible (as they require internal positive pressure to inflate) and hence, they may easily be slipped over patients, whereas negative pressure systems would require and in fact, need a rigid "tent" like structures to position a patient within the isolation "tent".

Stated simply, one or more embodiments of the present invention provide an isolation system that is low cost, portable, easily deployed, and single use disposable infectious disease containment system designed to minimize risk to patient and medical personnel while allowing patient monitoring, care, and transport (as further detailed below).

The isolation system of the present invention operates at a very low internal positive pressure (about 50 Pa) and high gas flow of about 10 to 15 liters per minute (either medical grade oxygen from a tank or ~90% oxygen from an oxygen concentrator, or air).

FIG. 1A to 1E-11 are non-limiting, exemplary illustrations of an isolation system packaging, which progressively illustrate a non-limiting, exemplary method for unpacking the same in accordance with one or more embodiments of the present invention.

Figure 1B:
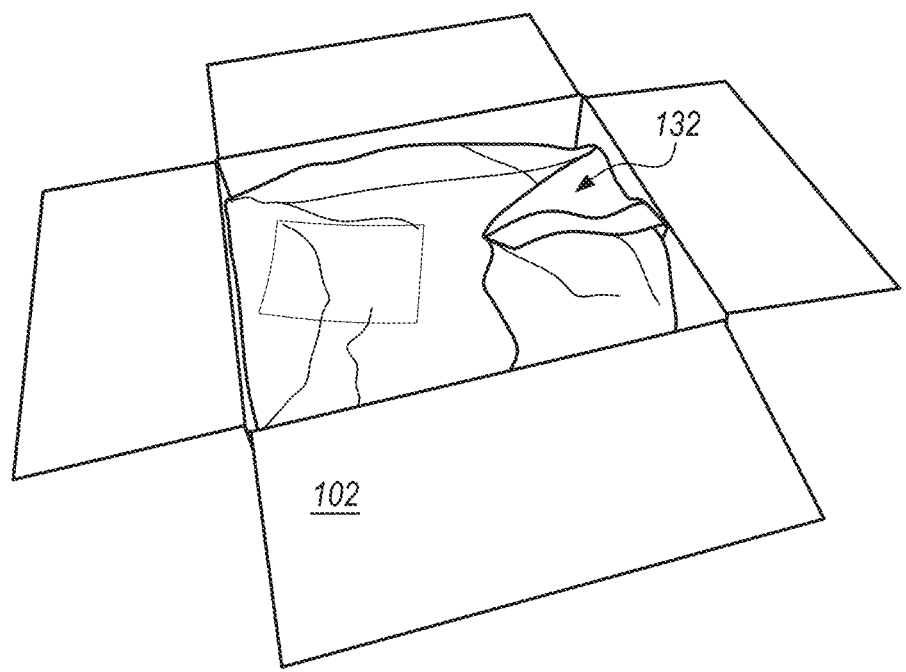
Figure 1C:
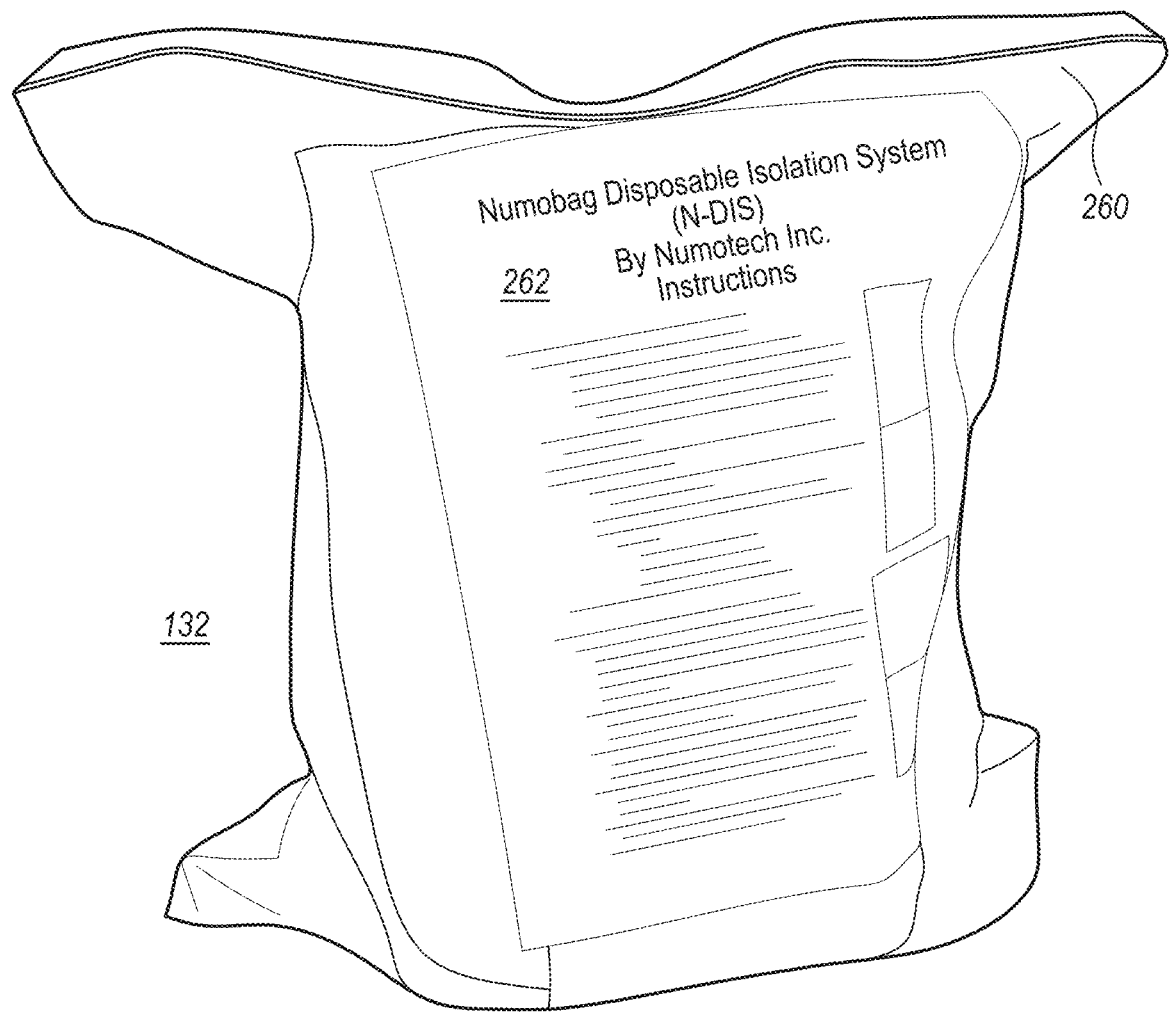

As illustrated in FIGS. 1A to 1C, the lightweight and portable isolation system 100 (FIG. 1D-1) of the present invention may be delivered for use to first responders in a small sized form factor in an isolation system package box 252 with an approximate weight of about 1815 g, having an approximate height 254 of about 23 mm, an approximate length 256 of about 30 mm, and an approximate width 258 of about 26 mm. Accordingly, due to their small sized form-factor, multiple isolation system packages 252 may be stored in vehicles for use for safe transportation of patients.

It should be noted that the use of isolation system package box 252 may be optional as isolation system 100 is already packaged inside as an isolation system kit 132 enclosed in a plastic bag (e.g., a Ziploc® bag) 260, as best shown in FIGS. 1B and 1C. However, use of an isolation system package box 252 is preferred as it provides rigidity for added protection for the internally stored isolation system kit 132.

As best illustrated in FIGS. 1B and 1C, the lightweight and portable isolation system 100 is further packaged as isolation system kit 132 inside a closed plastic bag (e.g., a Ziploc® bag) 260 with a readily visible instruction sheet 262 for simple and easy use.

The entire isolation system packaging is very low cost, providing immediate savings to medical facilities and further, meets jurisdictional quarantine protocols, including having an unattended storage life of about 5 years.

FIGS. 1D-1 to 1D-8 are non-limiting, exemplary illustrations of components of isolation system kit 132 opened and unpacked. It should be noted that isolation system kit 132 and all its components are medical grade cleaned (standard IEST-STD 1246D Level 100 clean), but not sterile.

As illustrated in FIGS. 1A to 1D-8, isolation system 100 within isolation system kit 132 includes a medical grate polymer (i.e., polyethylene) membrane 102, which is wrapped around a rolling member 266 (further detailed below). Further included is a conventional medical grade oxygen rated inflow tube 114 (approximately 1 m), an exhaust filter assembly 118, and a medical grate hose barb adapter 264.

As best shown in FIGS. 1D-6 to 1D-8, exhaust filter assembly 118 includes a medical grade oxygen rated outflow tubing 128 (approximately 0.2 m), a HEPA filter subassembly 134, including HEPA filter 228 and filter protective output plug 120 connected to output end 122.

FIGS. 1E-1 to 1E-11 are a non-limiting, exemplary illustration of a deflated polyethylene membrane 102 of the isolation system shown in FIGS. 1A and 1D-8 in accordance with one or more embodiments of the present invention. As illustrated, once removed from kit 132, medical grade polyethylene membrane 102 may be unfurled (FIGS. 1E-1 to 1E-4) and spread open (FIGS. 1E-5 and 1E-11).

As best shown in FIGS. 1E-1 to 1E-3, a rolling member 266 configured as a generally cylindrical foam is used to wrap membrane 102 to prevent seal member 106 from being kinked as membrane 102 is rolled into a small form-factor for packaging and storage.

Since rolling member 266 is a soft, cushiony "spongy" foam, it may be used as a head rest "pillow" or knee bolster, etc. during transport of a patient either with the patient inside membrane 102 or outside of membrane 102.

It should be noted that the use of rolling member 266 is preferred but is optional as the kinking would not damage seal membrane 106. However, it would generally make closure of seal member 106 more difficult to use. Accordingly, the entire membrane 102 may be folded around a smaller sized diameter rolling member 266 or simply folded flat (rather than rolled) into a much smaller and more compact form-factor, requiring a smaller kit and box packaging if rolling member is not used.

As further detailed below, a first port 110 of membrane 102 and a second port 112 of membrane 102 may be covered over by protective foam covers 268 (FIG. 1E-4) when packaged for delivery so that first and second ports 110 and 112 do not break or accidentally puncture membrane 102 as it is rolled into its small sized packaging.

FIG. 1E-5 illustrates first and second ports of membrane 102 with protective foam covers 268 and FIG. 1E-6 illustrates first and second ports of membrane 102 with protective foam covers 268 removed.

As further detailed below, depending on jurisdictional requirements a set of warning/instruction labels 270 may be positioned adjacent one or both first and or second ports 110 and 112. FIG. 1E-7 is an exemplary illustration of opening 104 of membrane 102, including sealing member 106, all of which are further detailed below.

As further illustrated in FIGS. 1E-8 to 1E-11, medical grade polyethylene membrane 102 has open end 104 that includes seal member 106 that enables access to its internal cavity or chamber and may be used to cover a patient over, surround, and seal off a patient.

It should be noted that medical grade oxygen rated inflow tube 114, medical grade oxygen rated outflow tube 128, and exhaust filter assembly 118 are not connected to the polyethylene membrane 102 while in isolation system kit 132.

As detailed below, the medical grade oxygen rated inflow tube 114, medical grade oxygen rated outflow tube 128, and exhaust filter assembly 118 may be connected after the polyethylene membrane 102 is removed from isolation system kit 132, unfurled and spread open (FIGS. 1E-5 to 1E-11). FIG. 1E-9 further illustrates connecting an end of medical grade oxygen rated inflow tube 114 to an oxygen sourced regulator valve 116 (may optionally use hose barb adapter 264).

FIGS. 1E-10 and 1E-11 are close up illustrations of connections of inflow tube 114 and outflow tube 128 to respective first and second ports 110 and 112. FIGS. 2A-1 to 2A-13 illustrate a preferred method in the order of connection of various components.

FIGS. 2A-1 to 2A-13 and 2B-1 to 2B-7, are non-limiting, exemplary illustrations of the isolation system shown in FIG. 1A to 1E-11, progressively illustrating a non-limiting, exemplary methods for fully sealing and isolating a patient in accordance with one or more embodiments of the present invention.

In particular, FIGS. 2A-1 to 2A-13 illustrate isolating a patient 108 within polyethylene membrane 102 with feet first whereas FIGS. 2B-1 to 2B-7 illustrate isolating patient 108 within polyethylene membrane 102 with head first. Various components of isolation system 100 are further described in relation to FIGS. 2A-1 to 2B-7.

As illustrated in FIG. 2A-1 to 2A-13, after unpacking isolation system 100 as detailed above, membrane 102 should be positioned flat with first and second ports 110 and 112 facing upward (as shown in FIGS. 1E-5 to 1E-9).

Figures 1, 1D:
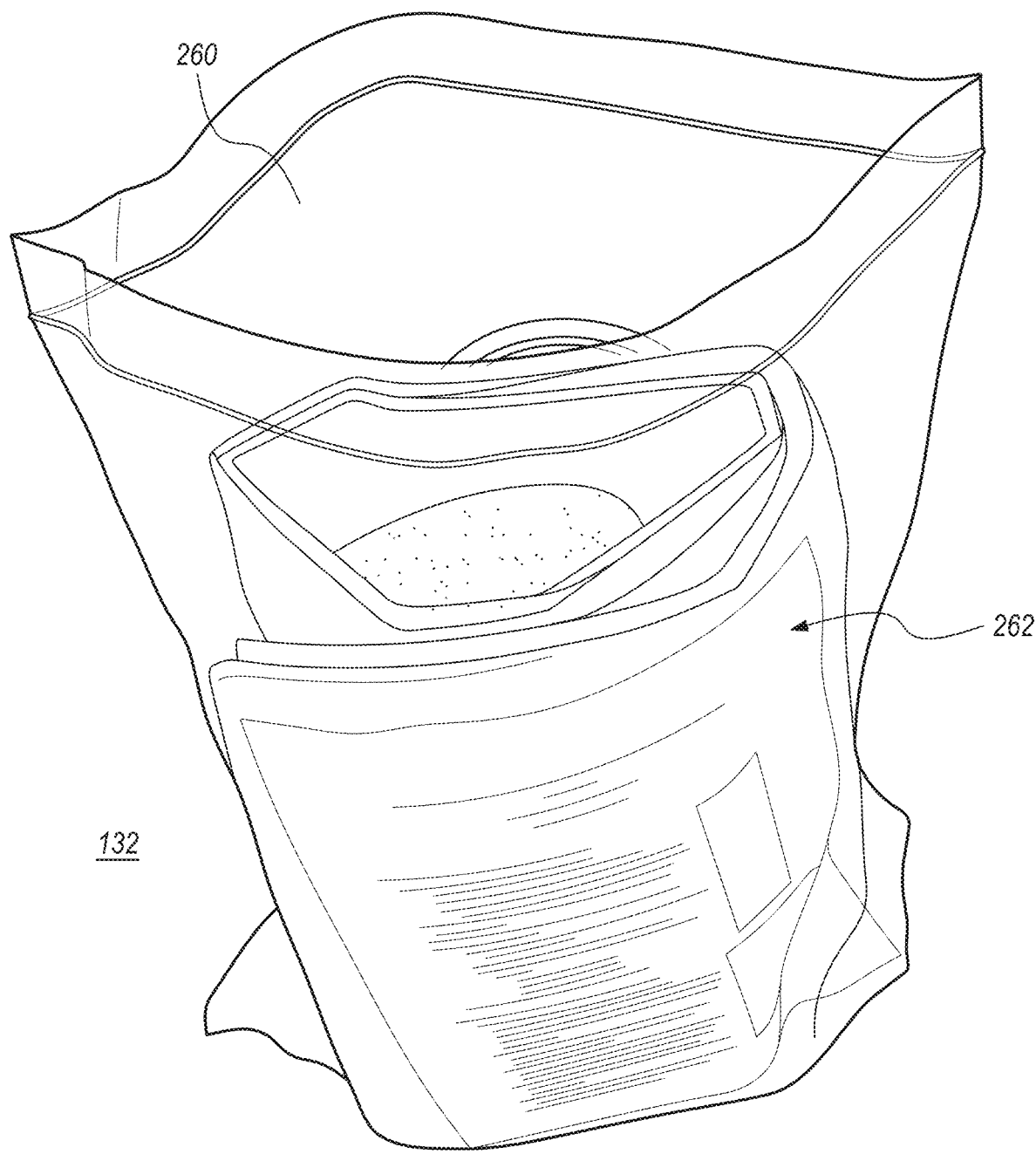
Figures 1, 2A:
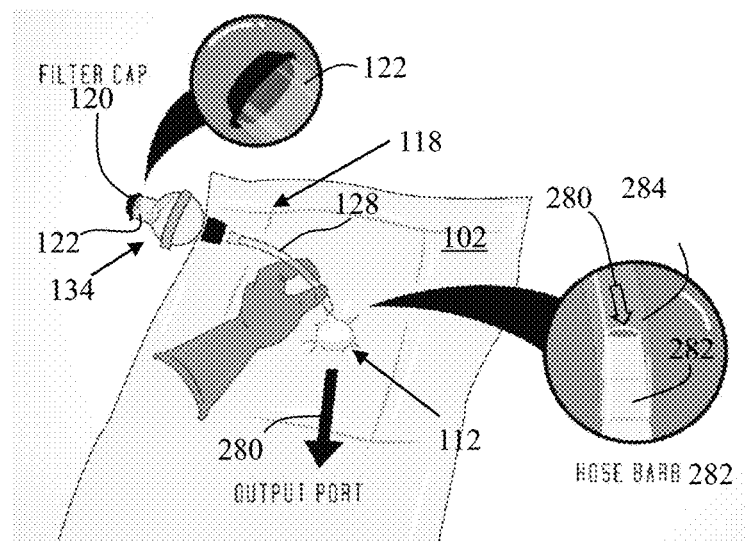
Figures 2, 2A:
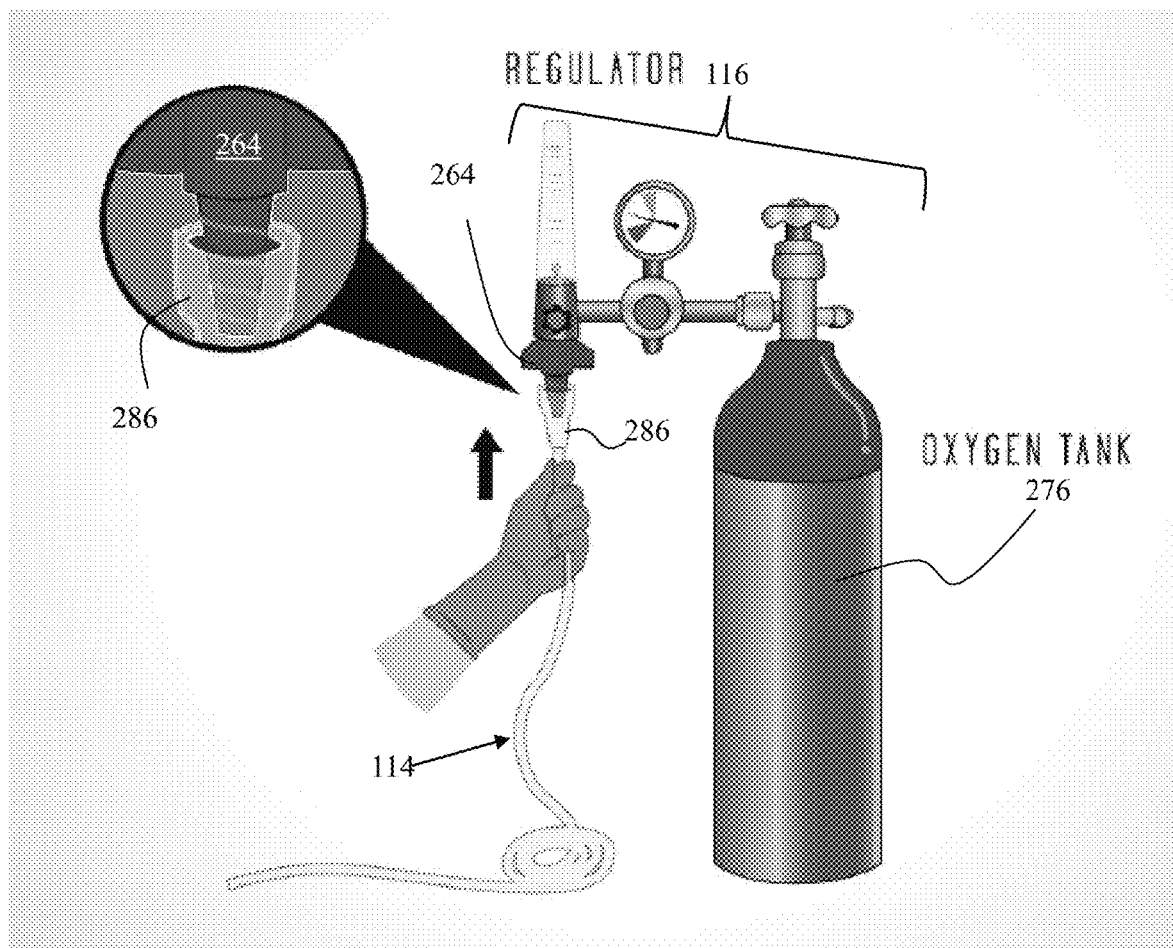
Figures 2, 2A, 3:
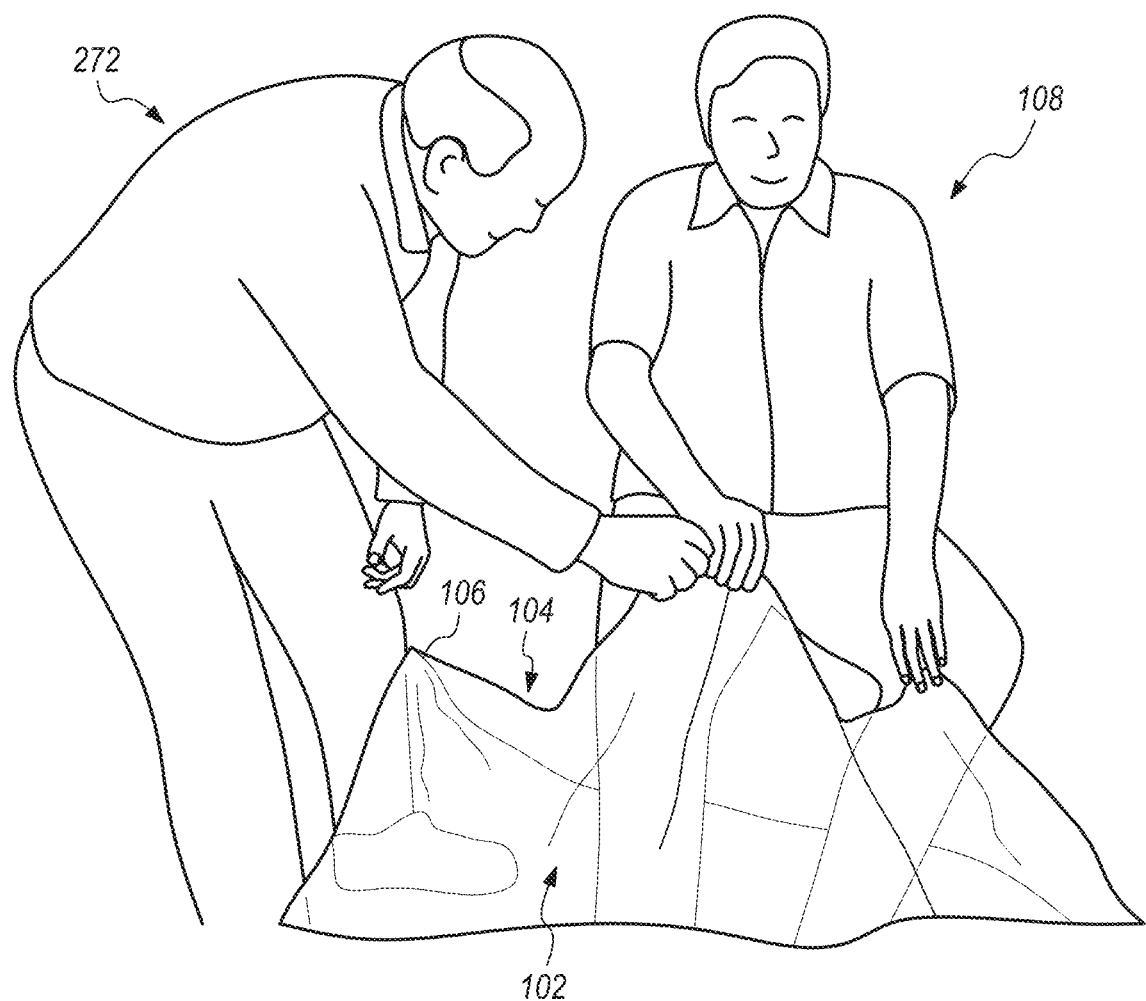
Figures 2, 2A, 3, 4:
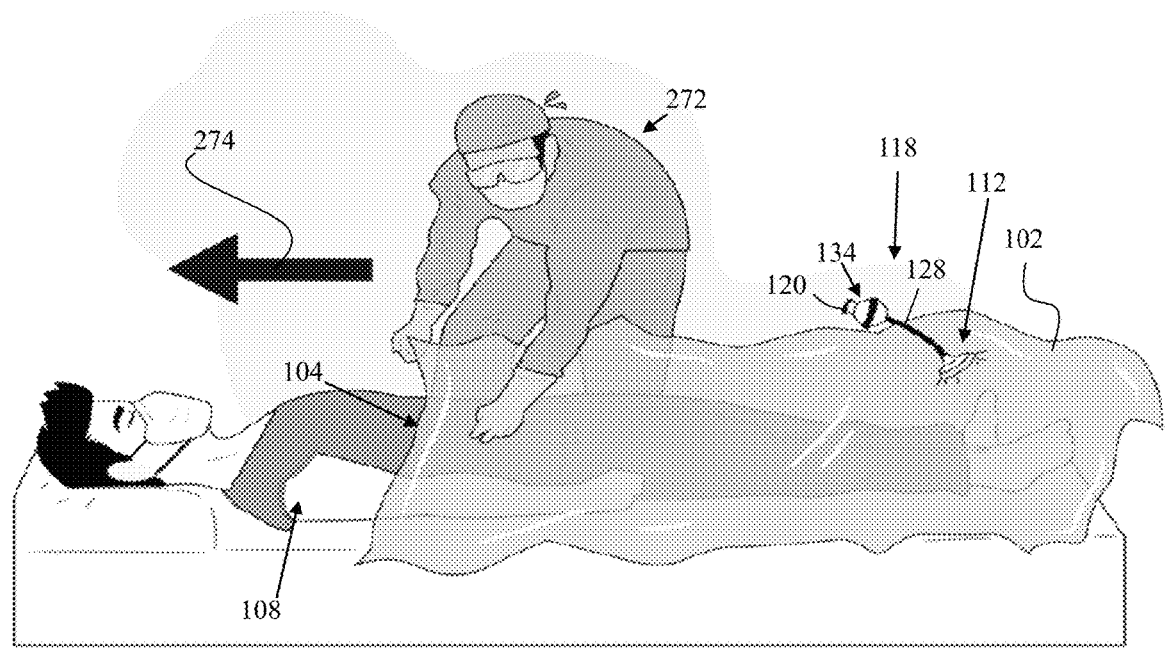
Figures 2, 2A, 3, 4, 5:
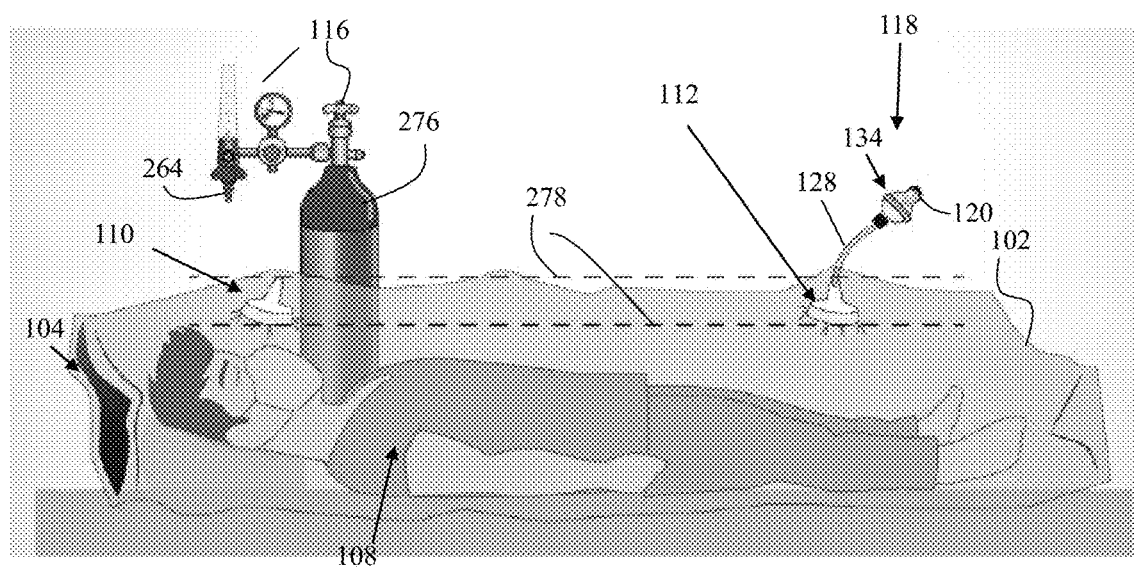
Figures 2, 2A, 3, 4, 5, 6:
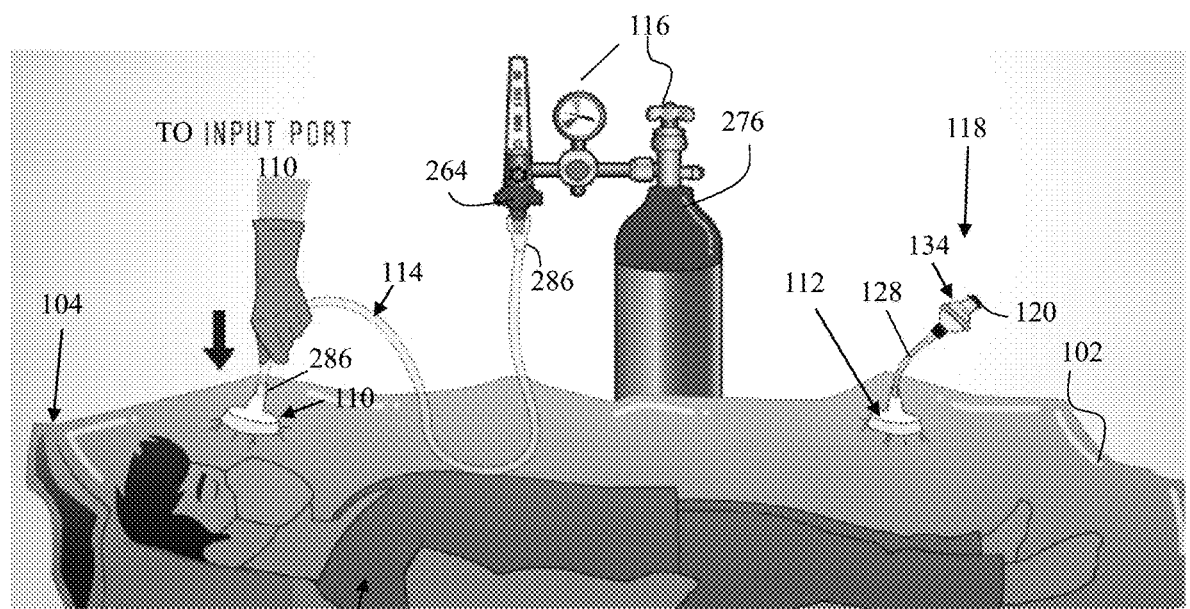
Figures 2, 2A, 3, 4, 5, 6, 7:
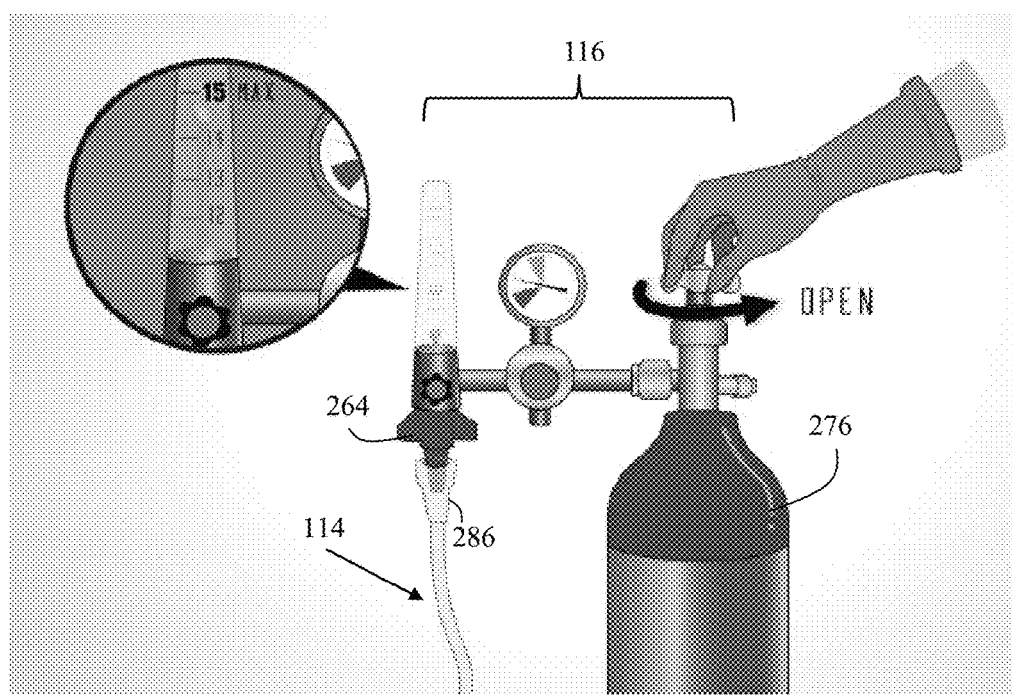
Figures 2, 2A, 3, 4, 5, 6, 7, 8:
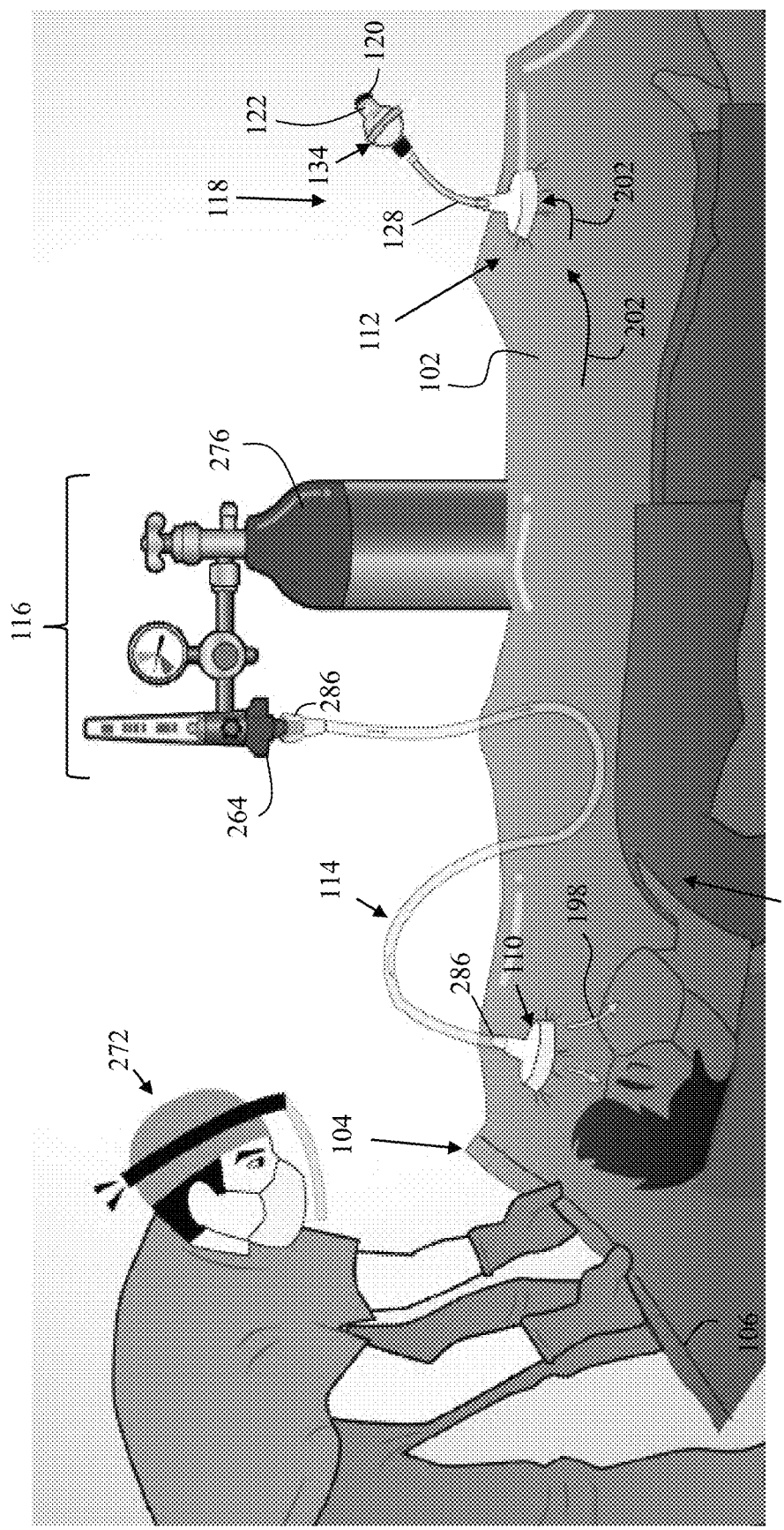
Figures 2, 2A, 3, 4, 5, 6, 7, 8, 9:
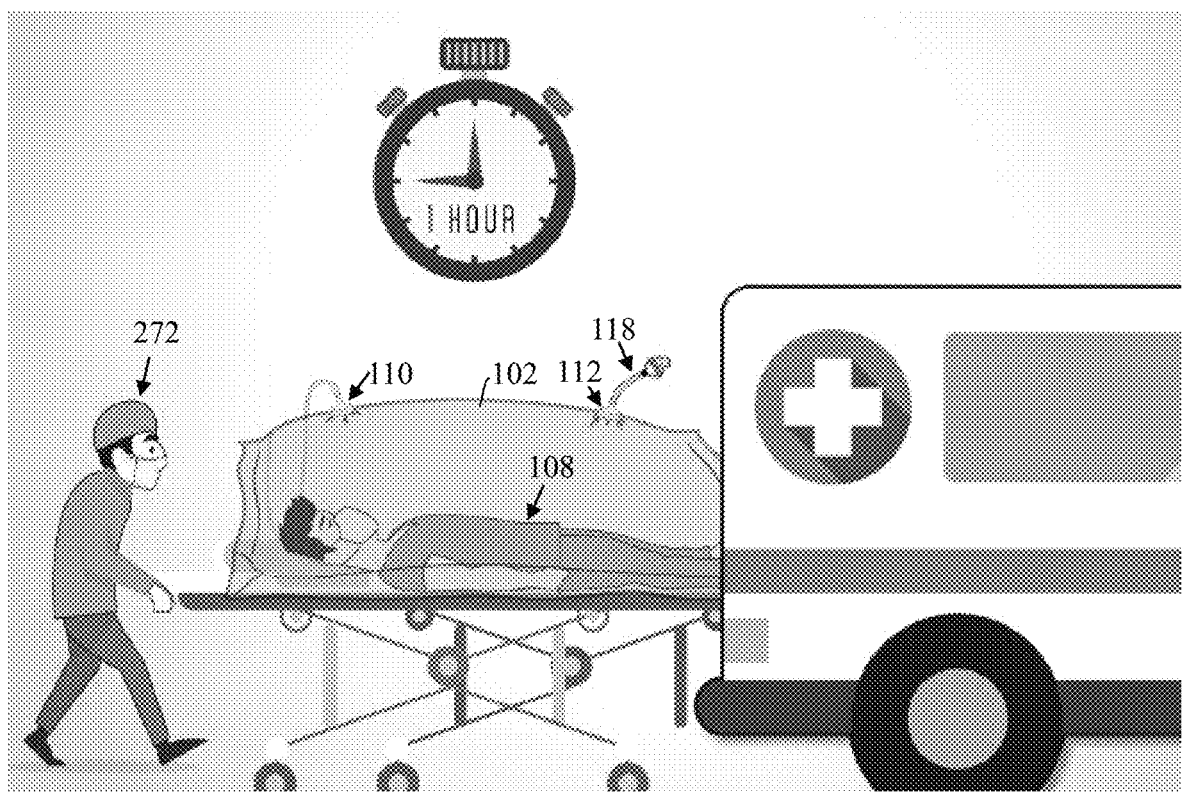
Figures 2, 2A, 3, 4, 5, 6, 7, 8, 9, 10:
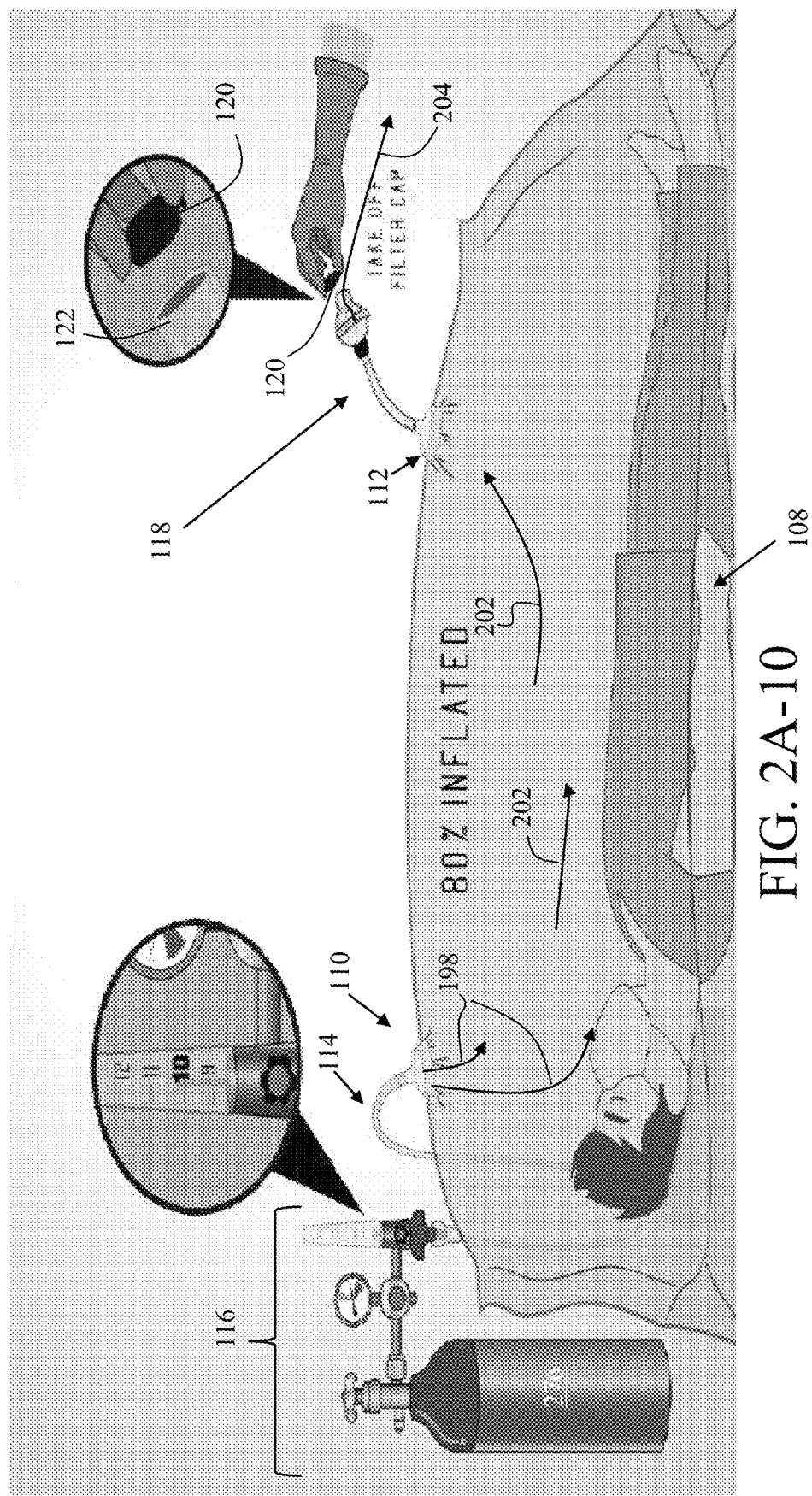
Figures 2, 2A, 3, 4, 5, 6, 7, 8, 9, 10, 11:
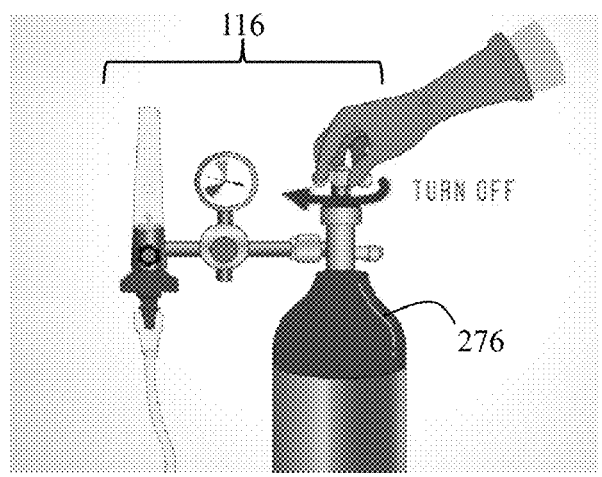
Figures 2, 2A, 3, 4, 5, 6, 7, 8, 9, 10, 11, 12:
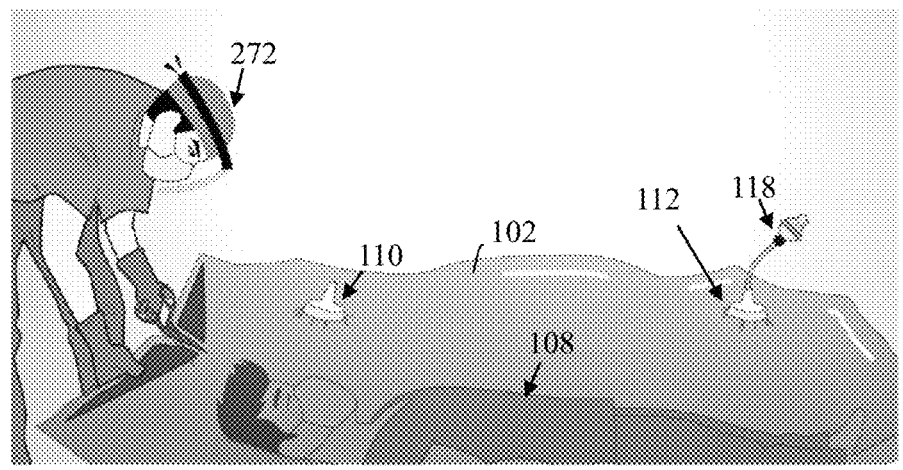
Figures 2, 2A, 3, 4, 5, 6, 7, 8, 9, 10, 11, 12, 13:
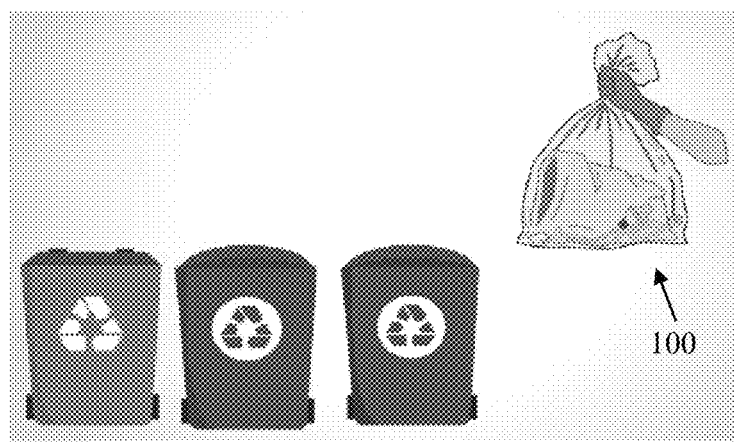
Figures 2, 2B:
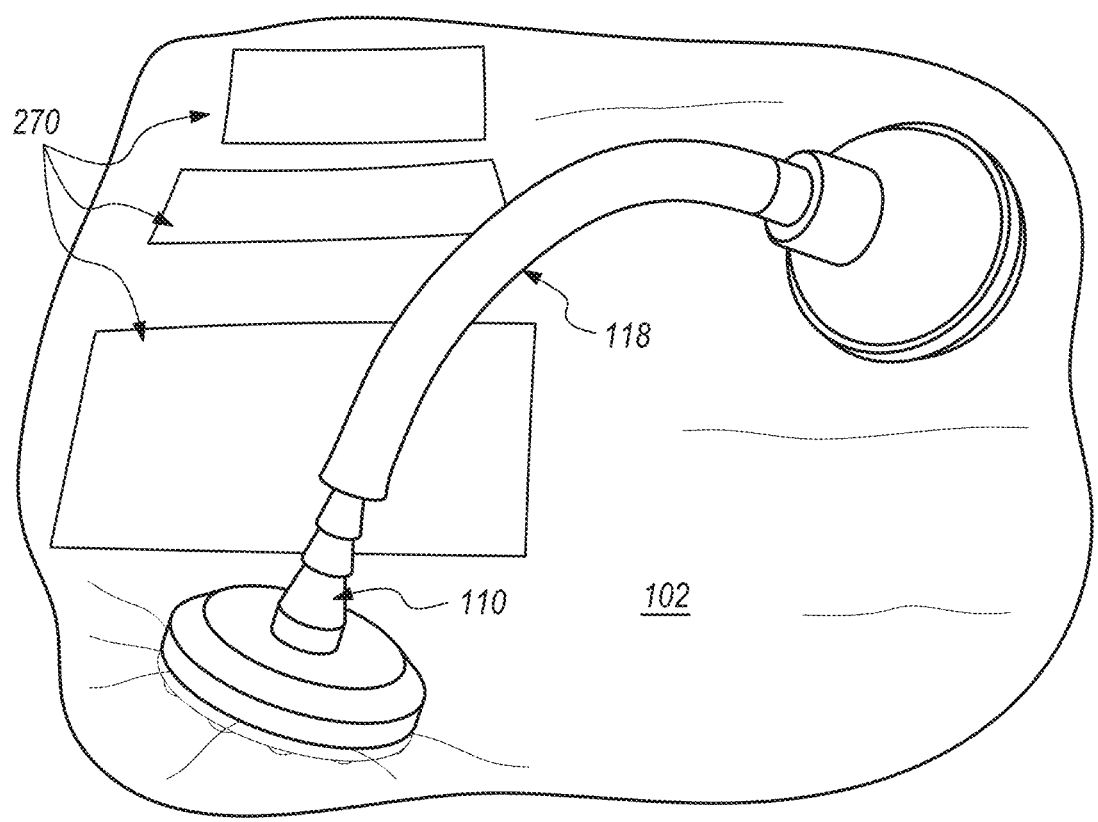
Figures 2, 2B, 3:
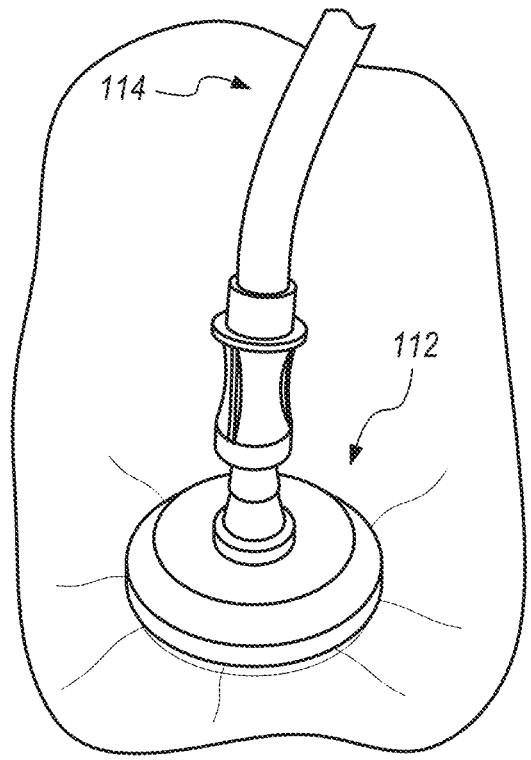
Figures 2, 2B, 3, 4:
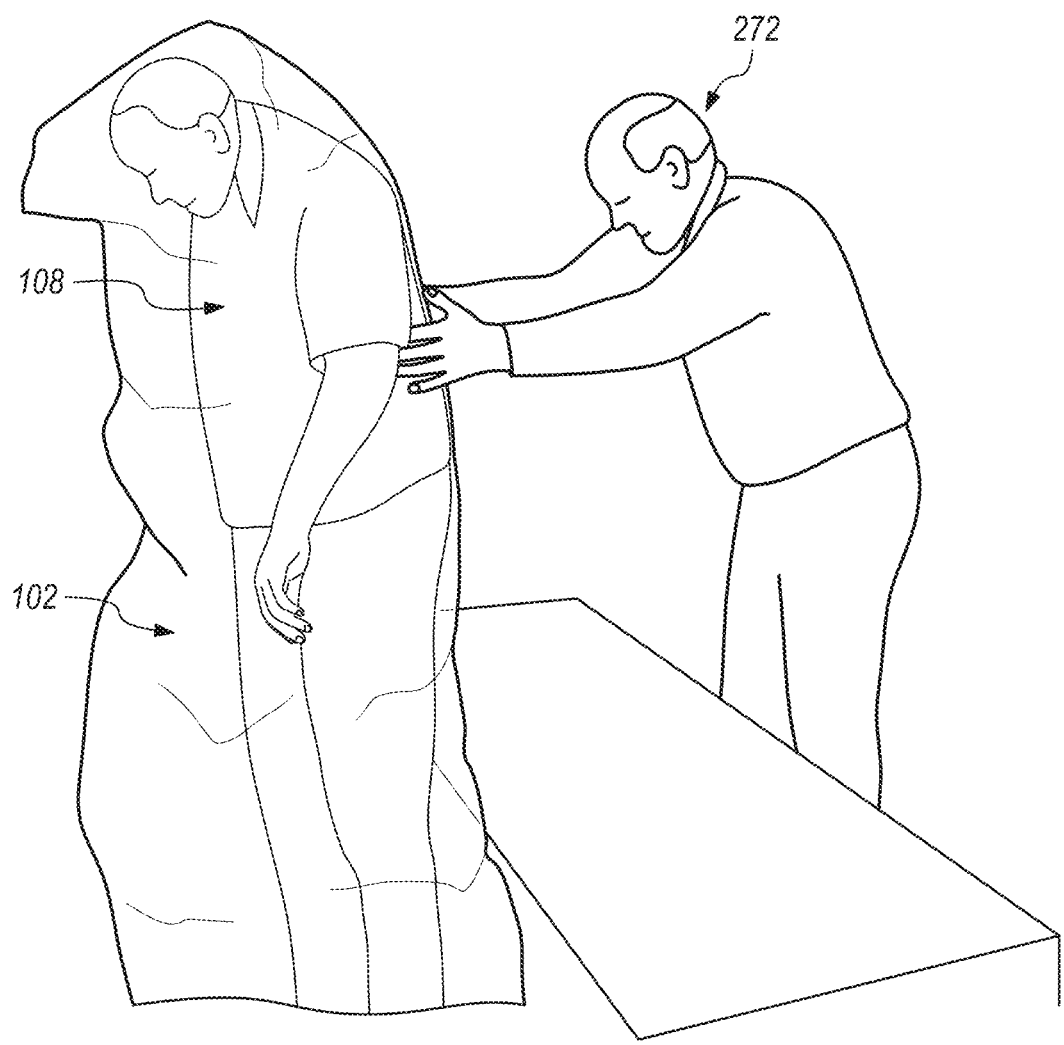
Figures 2, 2B, 3, 4, 5:
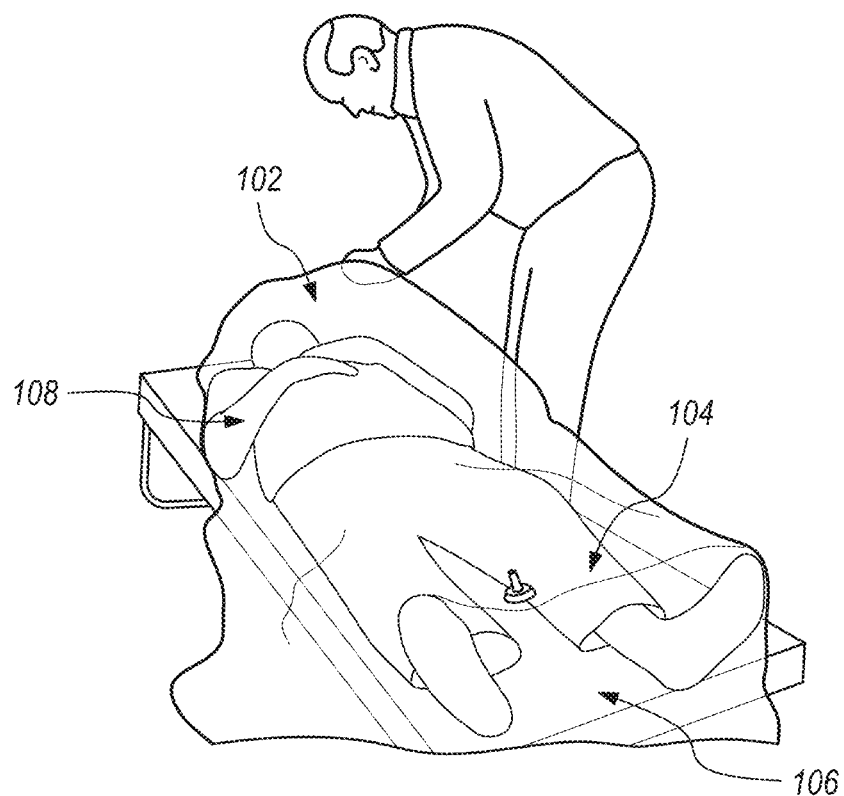
Figures 2, 2B, 3, 4, 5, 6:
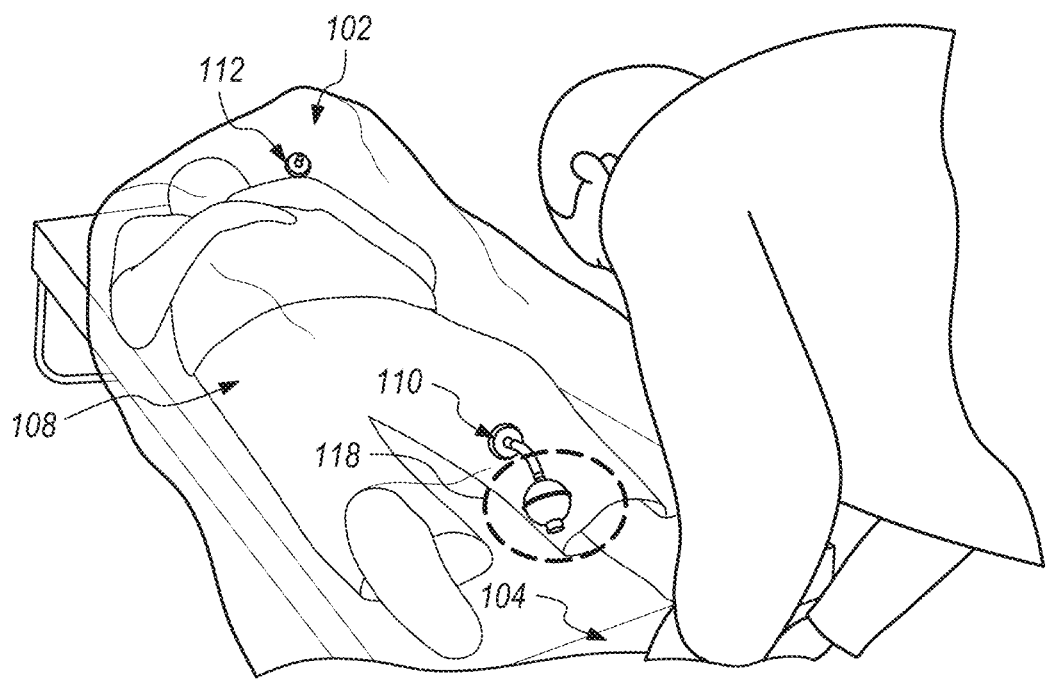
Figures 2, 2B, 3, 4, 5, 6, 7:
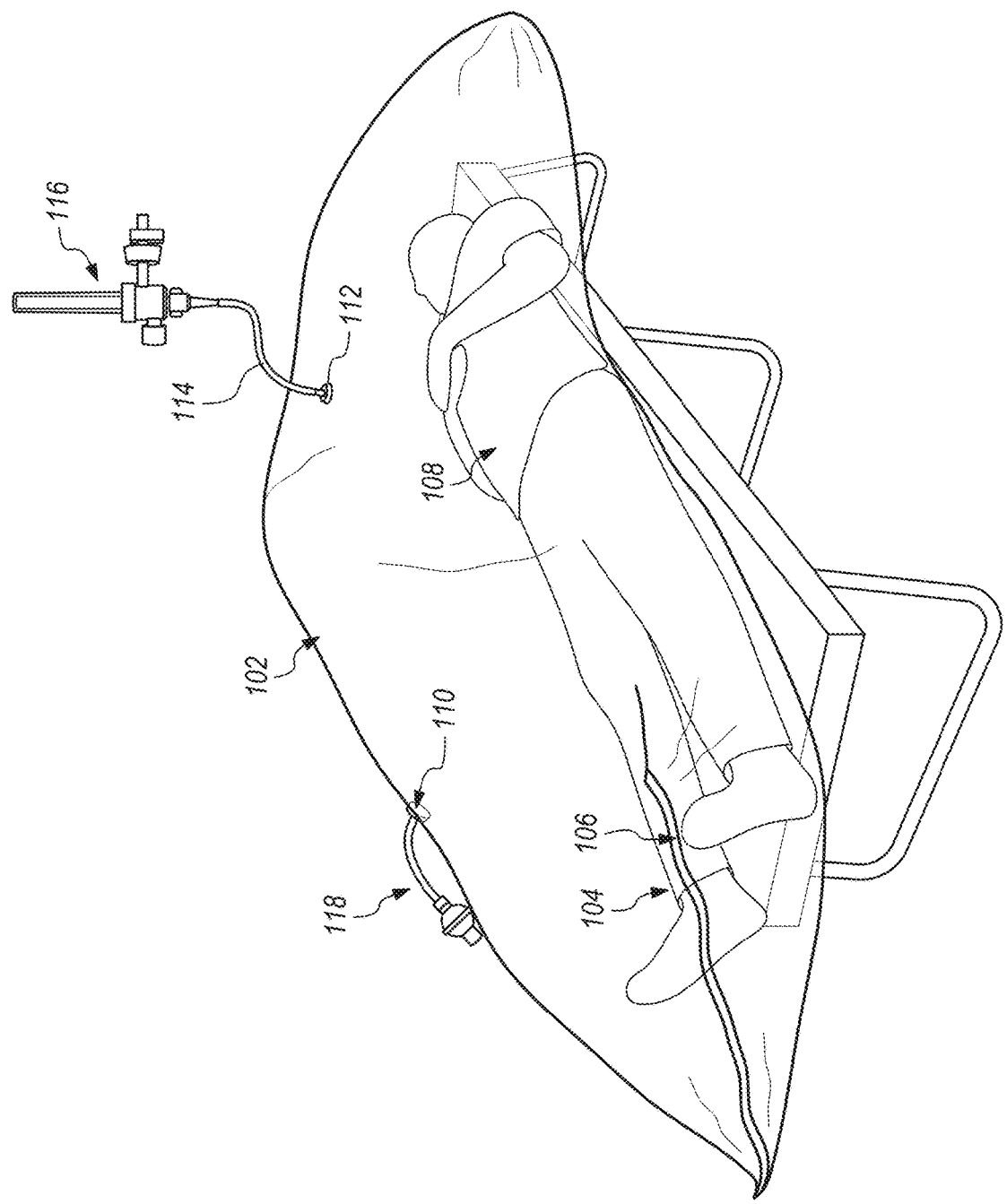

Next, exhaust filter assembly 118 may be attached to second port 112 as shown in FIG. 2A-1. That is, free end 284 of outflow tubing 128 of exhaust filter assembly 118 may be connected to the port (110 or 112) nearest the patient's feet.

In this non-limiting, exemplary instance, second port 112 is to be used as the "outlet" port of isolation system 100 as it is the closest port to the patient's feet and the patient head will be near the opening 106 of membrane 102. Free end 284 of outflow tubing 128 of exhaust filter assembly 118 may be connected to second port 112 by sliding free end 284 over hose barb 282 of second port 112 in the direction shown by arrows 280. As further detailed below, at this stage it is best-practice if filter protective output plug 120 is not removed to initially quickly inflate polyethylene membrane 102.

Figures 1, 1D, 2:
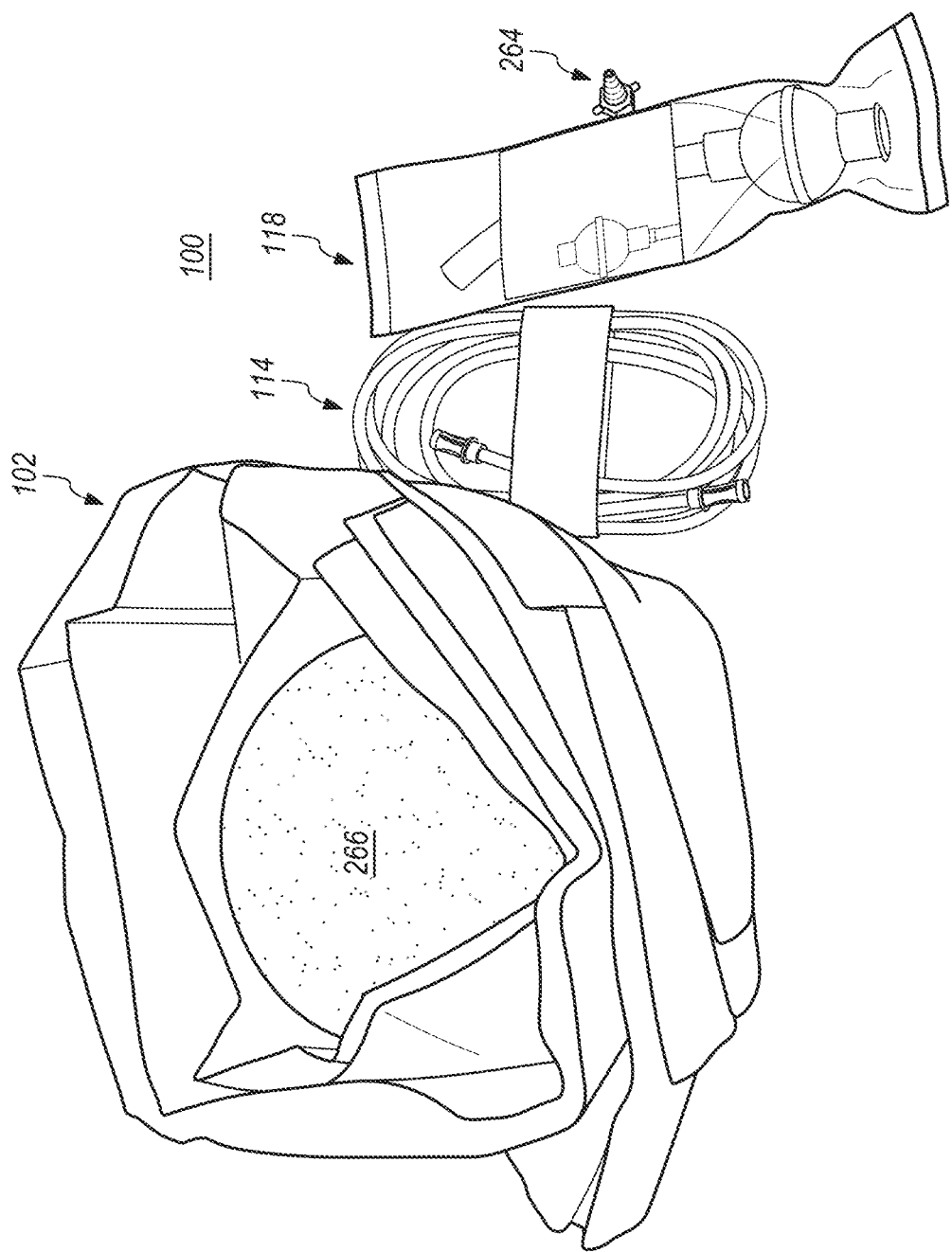
Figures 1, 1D, 2, 3:
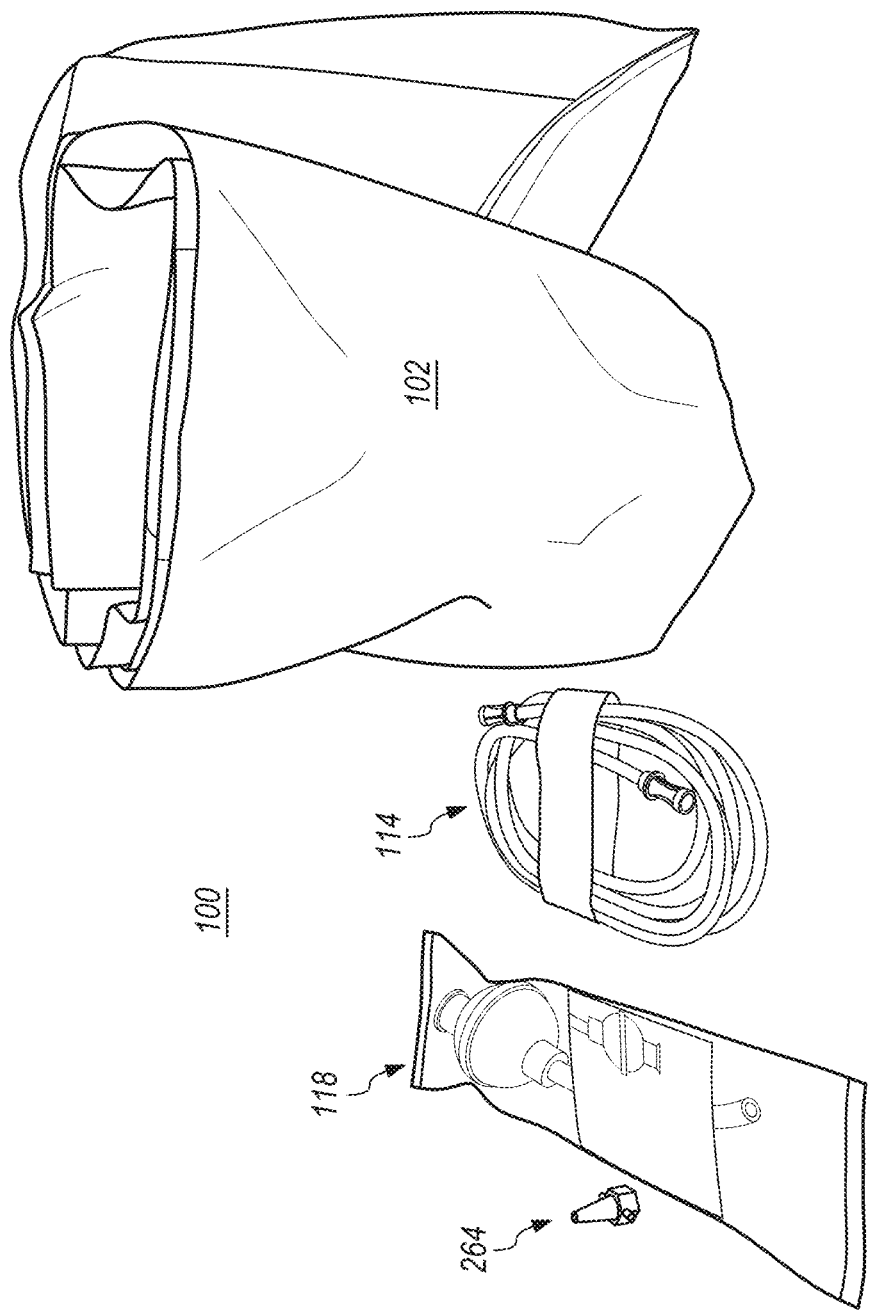

As best illustrated in FIG. 2A-2, one of the ends 286 of inflow tube 114 may be attached to regulator valve 116 of a source 276 of oxygen (or oxygen concentrator) or air, etc. via hose barb adapter 264.

As best shown in FIGS. 2A-3 and 2A-4, membrane 102 may be maneuvered by a first responder 272 at its open end 106 to encapsulate a patient 108. Patient 108 may be sitting upright in a chair (FIG. 2A-1) or in a prone or supine position (FIG. 2A-2), with polyethylene membrane 102 maneuvered (shown by arrow 274 in FIG. 2A-2) by first responder 272 to cover the patient to commence isolation from the feet first to the head to complete the covering of patient 108 with polyethylene membrane 102 (FIG. 2A-5).

As best illustrated in FIG. 2A-5, both first and second ports 110 and 112 must be aligned (as shown by the illustrated phantom alignment lines 278) on the front middle plane of patient 108. It should be noted that in FIG. 2A-5, the connection of inflow tube 114 to oxygen or air source 276 is intentionally not shown for clarity.

As shown in FIG. 2A-6, prior to sealing membrane 102 the other end 286 of inflow tube 114 is connected to first port (in this instance, inlet port) 110. As detailed in FIG. 2A-2, the other end (upstream end) 286 of inflow tube 114 is already connected source 276 of oxygen or air. Accordingly, prior to closing off sealing member 106 to seal off and isolate patient 108, a second or downstream end of a medical grade oxygen rated fill tubing 114 that is included in the kit is used and connected to one of a first port 110 and a second port 112, depending on head position of patient 108 inside the polyethylene membrane 102.

As detailed below, polyethylene membrane 102 includes first port 110 and second port 112, either one of which may be used as the "inlet" or the "outlet" port depending on the position of the head of patient 108 in relation to the nearest port. In the non-limiting, exemplary instance shown in FIGS. 2A-1 to 2A-13, first port 110 is to be used as the "inlet" port as it is the closest port to the patient's head and hence, second or downstream end of medical grade oxygen rated fill tubing 114 is connected to hose barb 282 of first port 110.

Thereafter, as best shown in FIG. 2A-7 oxygen or air regulator valve 116 may be opened to commence inflating membrane 102. As further detailed below, the initial flow rate may preferably be set at about 15 liters per minute (l/m) into membrane 102 cavity or chamber.

As shown in FIG. 2A-8, a first responder may than simply seal off membrane 102 using sealing member 106 as shown. That is, as a final step for isolating patient 108 within polyethylene membrane 102, sealing member 106 may be closed off to seal off and isolate patient 108 while medical grade oxygen continues to fill the polyethylene membrane 102 via regulator valve 116.

At this stage, polyethylene membrane 102 expands to inflate from a contracted state having a small form-factor to an expanded (inflated) state, defining an internal chamber that may be used to encapsulate and wholly encompass the entire body of patient 108. As illustrated throughout the disclosure, polyethylene membrane 102 has no rigid structures to maintain it in its expanded state and hence, it operates based on internal positive pressure, is simple to manufacture, is stored in a compact, small form-factor inside kit 132, and very simple to use.

As further illustrated in FIG. 2A-9, patient's transfer (of duration of no more than an hour or so) may commence while membrane 102 continues to inflate (as shown in FIG. 2A-9).

As shown in FIG. 2A-10, once membrane 102 is sufficiently inflated to an internal positive pressure $P_{Mem}$ of about 50 Pa, filter protective output plug 120 should be removed from output end 122. The removal of filter protective output plug 120 would allow for exhaust of gases 202 from within membrane 102 via exhaust filter assembly 118. At this stage, it is preferred if the input flow rate of the medical grade oxygen or air is readjusted and regulated to about 10 liters per minute to 15 liters per minute, sufficient to prevent excessive water vapor and carbon dioxide build up within membrane 102.

In FIG. 2A-10 illustrates patient 108 as fully isolated in the inflation process, at approximately 80% inflation, with oxygen or air inflows shown by arrows 198, exhaust outflows shown by arrows 202, and safe to breathe, uncontaminated air flowing out of exhaust filter assembly 118 shown by arrows 204.

FIGS. 2A-11 to 2A-13, are non-limiting, exemplary illustrations of procedures for extraction of the patient from membrane 102 in accordance with one or more embodiments of the present invention. As illustrated, once the final destination is reached (e.g., a medical facility such as a hospital), the flow of oxygen or air may be stopped (FIG. 2A-11), with inflow tube 114 disconnected from first (e.g., inlet) port 110.

Thereafter, membrane 102 may be unsealed by unfastening sealing member 106 or by slicing membrane 102 using scissors to remove patient (FIG. 2A-12). Thereafter, prior to removal of patient 108, it is best practice to allow a few seconds (e.g., approximately 15 to 30 seconds) for gas currents (if any) within membrane 102 to dissipate. Once the patient 108 is removed, the entire isolation system 100 may be disposed of as shown in FIG. 2A-13.

These simple, quick, and easy steps taken by first responders 272 shown in FIGS. 2A-1 to 2A-13 quickly and easily isolate patients 108 while enabling first responders 272 to continue maintaining visual observation of the patient (via the clear, thin, transparent polyethylene membrane 102) to assure comfort and management of patient, including making sure that the inflow of medical grade oxygen continues unabated into the polyethylene membrane 102. It should be noted that patients 108 and first responders 272 may also easily communicate with one another while patient 108 is fully isolated inside membrane 102.

FIGS. 2B-1 to 2B-7 are non-limiting, exemplary illustrations of encapsulating a patient within polyethylene membrane 102 with head first in accordance with one or more embodiments of the present invention. The method steps or operations illustrated in FIGS. 2B-1 to 2B-7 are similar to those shown in FIGS. 1A to 2A-13, and described above. Therefore, for the sake of brevity, clarity, convenience, and to avoid duplication, the general description of FIGS. 2B-1 to 2B-7 will not repeat every corresponding or equivalent component, interconnections, functional, operational, and or cooperative relationships that has already been described above in relation to FIGS. 1A to 2A-13 but instead, all are incorporated by reference herein.

As illustrated in FIGS. 2B-1 to 2B-7, in this non-limiting, exemplary instance, actions are taken to surround patient 108 with polyethylene membrane 102 when applied from the head to the feet. In this instance, a patient 108 may be standing upright next to a bed for example, where the polyethylene membrane 102 may be used to seal patient 108 from the head first to the feet to complete the covering of patient 108 with polyethylene membrane 102.

As shown in FIGS. 2B-1 to 2B-3, in this non-limiting, exemplary instance, one end 286 of the medical grade oxygen rated fill tubing 114 is connected to second port 112, which is to be used as the "inlet" port as it is the closest port to the patient's head. Exhaust filter assembly 118 is connect to first port 110. In this non-limiting, exemplary instance first port 110 is to be used as the "outlet" port as it is the closest port to the patient's feet.

As further illustrated in FIGS. 2B-4 to 2B-6, membrane 102 may be maneuvered by a first responder 272 at its open end 106 to encapsulate a patient 108. Patient 108 may be sitting or standing upright (FIG. 2B-4) or in a supine or prone position (FIGS. 2B-5 and 2B-6), with polyethylene membrane 102 maneuvered by first responder 272 to fully cover patient 108 to commence isolation from the head first to the feet to complete the covering of patient 108 with polyethylene membrane 102 (FIG. 2B-7).

Once patient 108 is moved into polyethylene membrane 102, first and second ports 110 and 112 are aligned to lie approximately on the frontal mid-plane of patient 108 as indicated above.

In this non-limiting, exemplary instance, seal member 106 is at the feet of patient 108 instead of adjacent the head. The remaining steps are identical to those described above in relation to 1A to 2A-13, with FIG. 2B-7 showing a non-limiting, exemplary illustration of a fully operational isolation system with an isolated patient 108.

As detailed, one or more embodiments of the present invention provide an isolation system that supports the protection of public health by ensuring that the first responders and medical staff are not exposed unnecessarily to infectious or contagious disease or other infectious matter while a patient is being transported to a final destination.

Further, the isolation system of the present invention protects vulnerable patients from the environment around them. Burn victims, patients recovering from cancer treatment, or others with severely compromised immune systems for example are particularly susceptible to airborne pathogens. The present invention may be used to fully isolate and protect such patients.

The present invention focuses on critical operational constraint to easily, rapidly, and assuredly encase patients within the isolation system to reduce or eliminate contaminations due to pathogens exposure.

Along with rapid isolation of the patient, another critical operational consideration is patient safety. The emplacement of the isolation system of the present invention does not cause undue physical discomfort for the patient, which would impede rapid and effective isolation.

Additionally, the ability to introduce medical grade oxygen into the isolation system and filtering out contaminated exhaust from the isolation system enhances the internal chamber environment for the patient while allowing the patient to be transported safely while isolated in the polyethylene membrane.

As indicated above, one of the key features of the isolation system of the present invention is that it is highly portable, one-time use and disposable. The medical grade oxygen, provided from a portable oxygen canister, may be flowing into the disposable containment polyethylene membrane in the range of 10 to 15 liters per minute during use, including transport, provided from a portable oxygen canister. The medical grade oxygen source can be facility piped-in oxygen or oxygen tanks. Nonetheless, the level of flow indicated above aids to ameliorate buildup of water vapor and carbon dioxide in the enclosure from exhalation of the patient.

Use of the isolation system of the present invention allows for management, control, and reduction of immediate threats to both patient and public health and safety. In addition, the isolation system in accordance with one or more embodiments of the present invention provide for a temporary isolation and containment of patients in scenarios such as, for example:

Non-deferrable medical treatment of infected persons in a shelter or temporary medical facility
Related medical facility services and supplies
Medical facilities and/or enhanced medical/hospital capacity (for treatment when existing facilities are reasonably forecasted to become overloaded in the near term and cannot accommodate patient capacity or to quarantine infected patients) thus protecting first responders and medical personnel.

Medical sheltering (e.g. when existing facilities are reasonably forecasted to become overloaded soon and cannot accommodate needs)

Sheltering conducted in accordance with standards and/or guidance approved by jurisdictional authorities such as, for example, HHS or CDC;

Supports Non-congregate medical sheltering.

Use of specialized medical equipment with isolation system

Emergency medical transport

Biohazard waste disposal

Figure 3A:
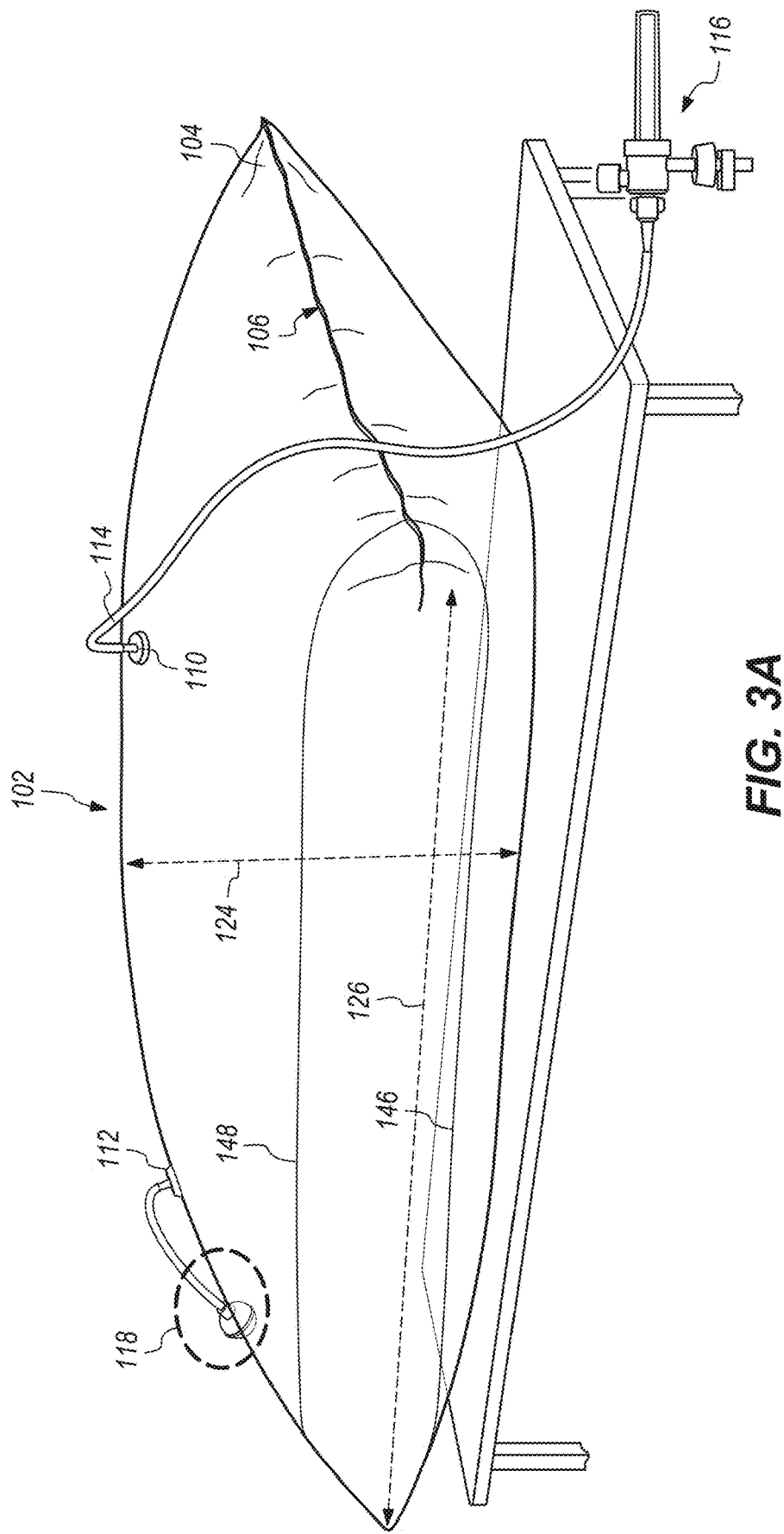
FIGS. 3A and 3B are non-limiting, exemplary illustrations of a fully assembled and functioning isolation system shown in FIG. 1A to 2B-7, but without an isolated patient sealed within in accordance with one or more embodiments of the present invention.
Figure 3B:
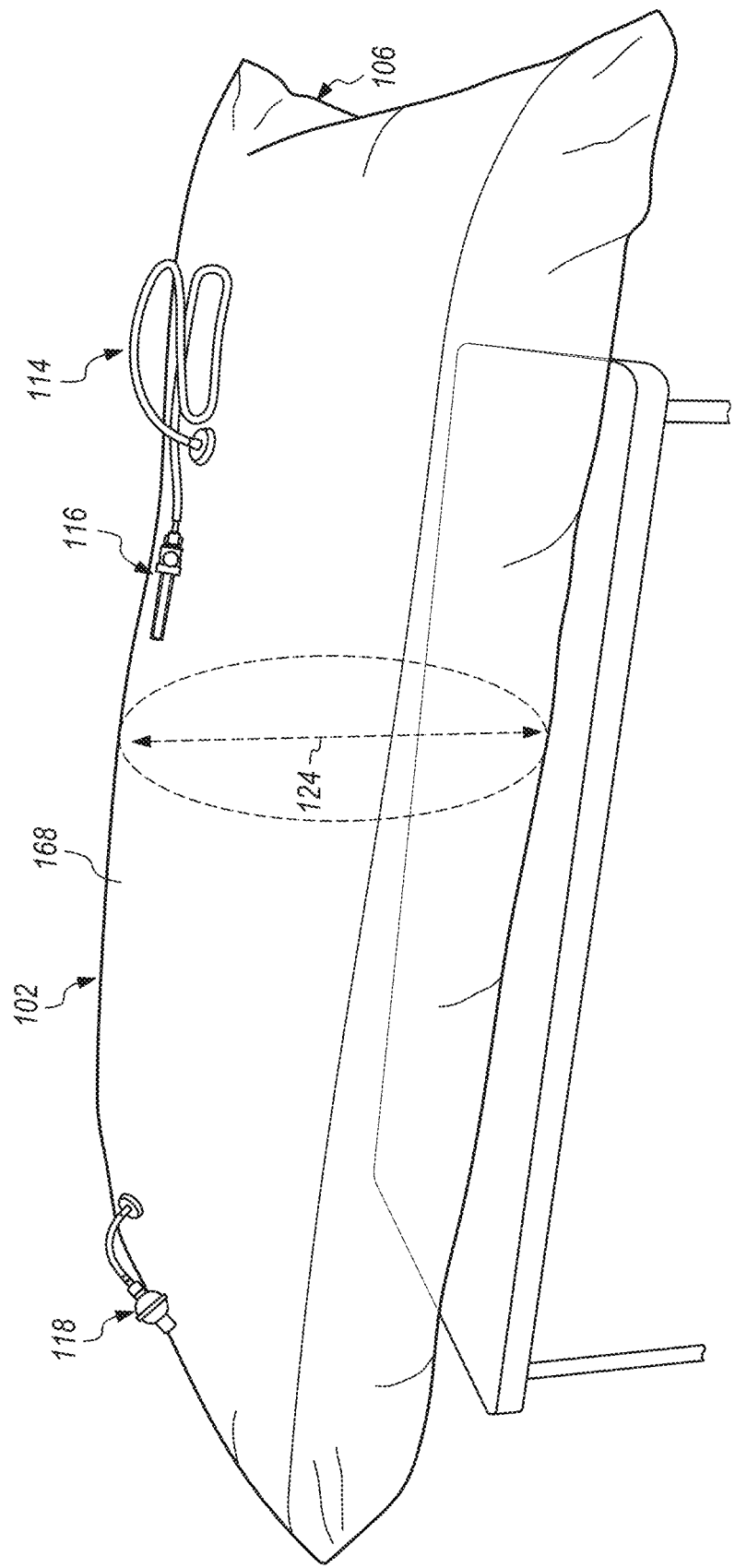

FIGS. 3A and 3B are non-limiting, exemplary illustrations of a fully assembled and functioning isolation system shown in FIG. 1A to 2B-7, but without an isolated patient sealed within in accordance with one or more embodiments of the present invention. Polyethylene membrane 102 may be filled with medical grade oxygen or air between 5 to 10 minutes while filter protective output plug 120 is removed.

As shown in FIGS. 3A and 3B, interior diameter 124 of an inflated polyethylene membrane 102 (about 80% inflated) is about 0.78 m, with an inflated length 126 of about 2.34 m providing a volume of about 1103 liters when inflated to about 80%. Polyethylene membrane 102 may be inflated for use from as low as 60% to fully inflated.

Below is a non-limiting, non-exhaustive, exemplary table of listing of some of the parameters of isolation system 100, including non-limiting, exemplary nominal preferred values when isolation system 100 is inflated to about 80% and non-limiting, exemplary preferred operational range values:

TABLE

| Variable | Approximate Nominal (or preferred) Values | Approximate Range Values |
|---|---|---|
| Internal Positive pressure | 50 Pa | 50 to 150 Pa (tested to ~1000 Pa for burst with no issues) |
| Oxygen or air flow | 10 liters per minute | 10-30 liters per minute |
| Membrane material | Polyethylene (IEST-STD 1246D Level 100) | Any clear plastic film compatible with $O_2$ |
| Membrane diameter | 0.78 meter | .5 to 1 meter |
| Membrane length (inflated) | 2.34 meter | 1.5 (pediatric) to 2.5 meter |
| Membrane thickness | 0.1 mm | 0.1 to 0.3 mm |
| First or second port tube section internal diameter | 3.81 mm | 3 to 4 mm as needed |
| First or second port tube section length | 5 cm | 4 to 6 cm |
| Exhaust Filter | HEPA (be & ve > 99.99%, flow efficiency 32 lpm) | HEPA of compatible size |

As further detailed below, the internal positive pressure is regulated by the pneumatic resistance to flow of the outlet hose barb 282 passage diameter and length. This pneumatic resistance to flow provides a nominal 50 Pa back pressure within membrane 102. This pressure level of about 50 Pa is sufficient to support membrane 102 in an inflated state while minimizing leakage flow (if any).

Various tests conducted on one or more embodiments of isolation system 100 of the present invention positively confirm the following:

The nominal oxygen or air inflow rate of about 10 liters per minute is sufficient to dilute Carbon Dioxide (CO2) and water vapor exhaled by the isolated patient, while limiting oxygen usage to preserve oxygen during the transport of the patient. Nominal oxygen or air inflow rate of about 10 liters per minute was determined based on a typical exhalation rates of an average individual. It should be noted that air may flow from a constant displacement air pump (which may require additional power source) at a rate of 20 to 30 liters per minute. Use of air is less preferred as it is the least effective (medically) because the patient does not receive oxygen enriched air. The flow rate of air is generally higher at about 20 to 30 liters per minute as compared with oxygen, which is at a flow rate of about 10 to 15 liters per minute. The higher flow rate of air is to lower the levels of exhaled carbon dioxide and water vapor that may accumulate inside membrane 102. The water vapor removal in maintaining low humidity inside membrane 102 is important when using air (rather than oxygen) because the air is simply the ambient outside air and hence, is not dry.

Temperature within membrane 102 of isolation system 100 stayed to within 5° C. of the surrounding environment after an hour.

The relative humidity within membrane 102 of isolation system 100 continued to exhibit increasing transient behavior after an hour of isolation of a subject, well below an extreme level of 98% humidity.

The subject within membrane 102 of isolation system 100 remained in a generally comfortable condition as exhibited by a generally slightly decreasing core body temperature during one-hour of isolation.

The subject in isolation within membrane 102 of isolation system 100 was able to clearly and easily communicate with people in the immediate surroundings as demonstrated by verbally providing data to an outside observer.

Extraction of patients from within membrane 102 of isolation system 100 (as detailed above) provided no observable aerosolization or expulsions of contaminants from membrane 102 of isolation system 100.

In general, expanded (inflated) state of the polyethylene membrane 102 is stabilized (e.g., volume remains fairly constant) at non-limiting, exemplary internal positive pressure measurements of approximately 100 Pa, 74 Pa, and 50 Pa at non-limiting exemplary flow rates of about 1:5 liters per minute, 10 liters per minute, and 5 liters per minute; respectively. The structural integrity of the polyethylene membrane 102 and seal member 106 closed remain unchallenged at any of the above-mentioned exemplary flow ratings.

Polyethylene membrane 102 remains sufficiently inflated (at a non-limiting, exemplary volume of about 1100 liters at about 5 to 15 liters per minute with flow unimpeded through exhaust filter assembly 118, but without polyethylene membrane 102 being excessively taut.

A flow of 10 to 15 liters per minute is a non-limiting, exemplary preferred setting for operation in accordance with one or more embodiments of the present invention. Polyethylene membrane 102 pressure is 50 Pa at the non-limiting, exemplary 10 liters per minute with the filter flow unimpeded. (Note; if the operator wishes polyethylene membrane 102 to be tauter, they can slightly impede the flow from exhaust filter assembly 118 by closing the outflow end 122 with filter protective output plug 120.)

Polyethylene membrane 102 may be filled with medical grade oxygen or air at the correct differential pressure to the atmosphere to shape membrane 102 for operational use. High inflows of oxygen (>15 liters per minute) may be used to shape (inflate) the polyethylene membrane 102 enclosure, but then can be reduced to very moderate rates (about 10 to 15 liters per minute) for sustained containment of patient 108 without excess use of oxygen gas.

Polyethylene membrane 102 may be easily inflated and moderately taut at 10 liters per minute of inflow. At 10 liters per minute flow rate polyethylene membrane 102 pressure is approximately 50 Pa, and at 15 liters per minute pressure would be about 115 Pa.

It should be noted that polyethylene membrane 102 pressure at 15 liters per minute is less than about 115 Pa, which is still a very low pressure. Previously conducted pressure tests have resulted in isolation system 100 to withstand non-limiting, exemplary test pressures of about 1000 Pa, with isolation system 100 able to tolerate higher operating pressures with no issues.

Those skilled in the art would appreciate that because there is low pressure, there is no risk of systemic absorption of oxygen and, thus, the risk of pulmonary or central nervous system toxicity that can result from breathing high-pressure oxygen is not a problem. The increased oxygen helps oxidize disease-causing organisms. Oxygen toxicity does not occur using isolation system 100 because of shorten length of use (about 1 hour or so) within the polyethylene membrane 102 with patient 108.

Figure 4A:
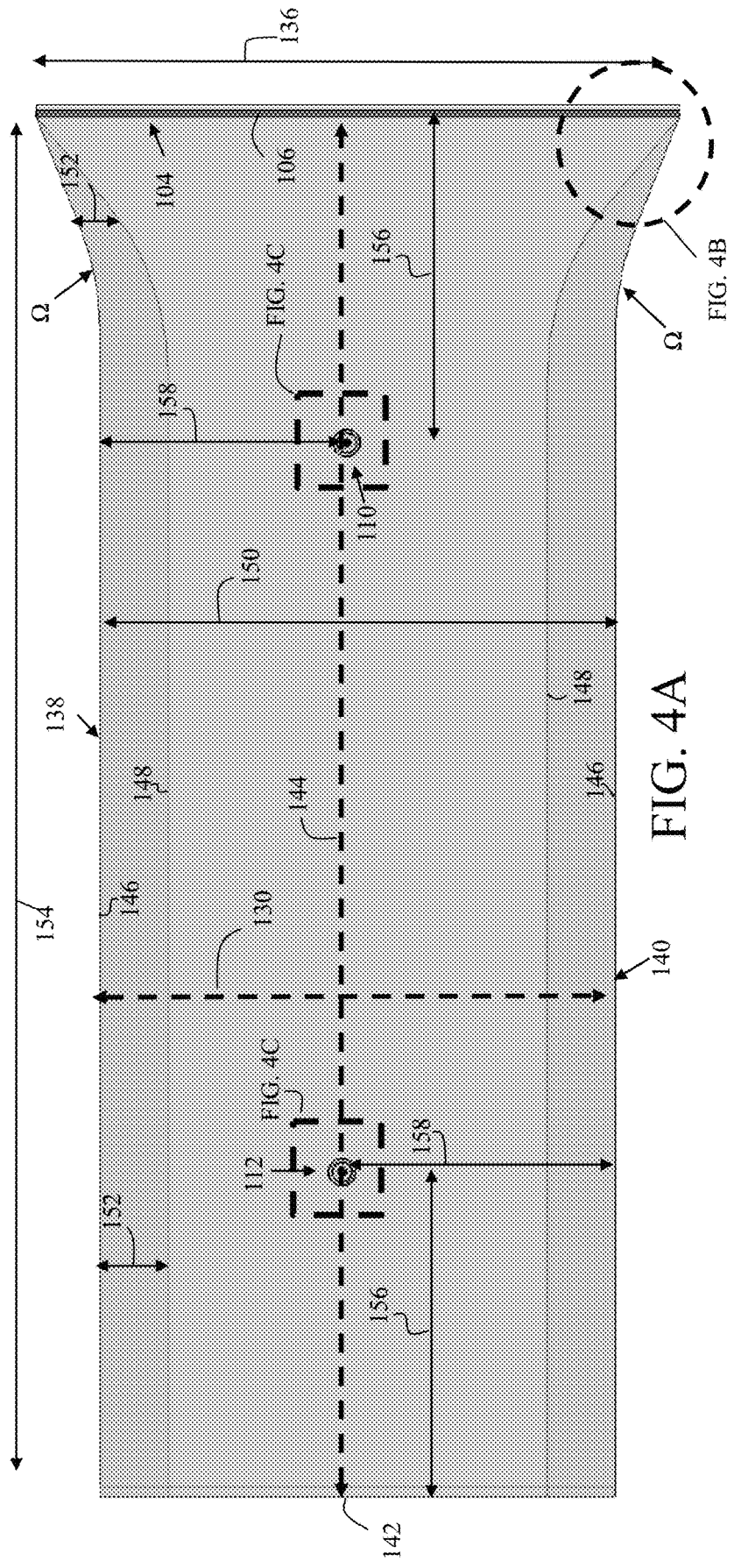
FIGS. 4A to 4V are a non-limiting, exemplary illustration of the isolation system of FIGS. 1A to 3B, with deflated (but unfurled) polyethylene membrane, including individual associated components in accordance with one or more embodiments of the present invention.
Figures 1, 4B:
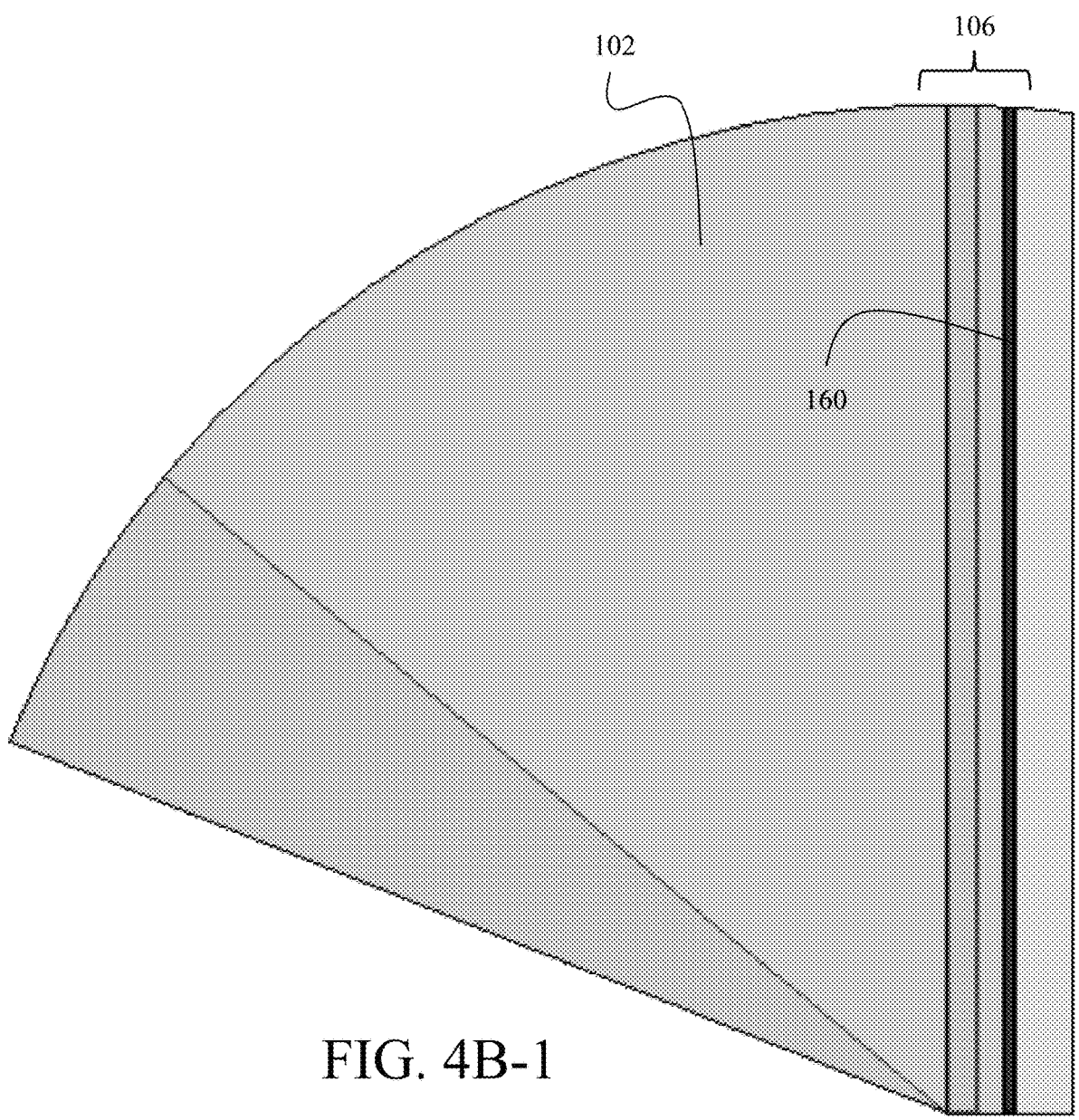
Figures 2, 4B:
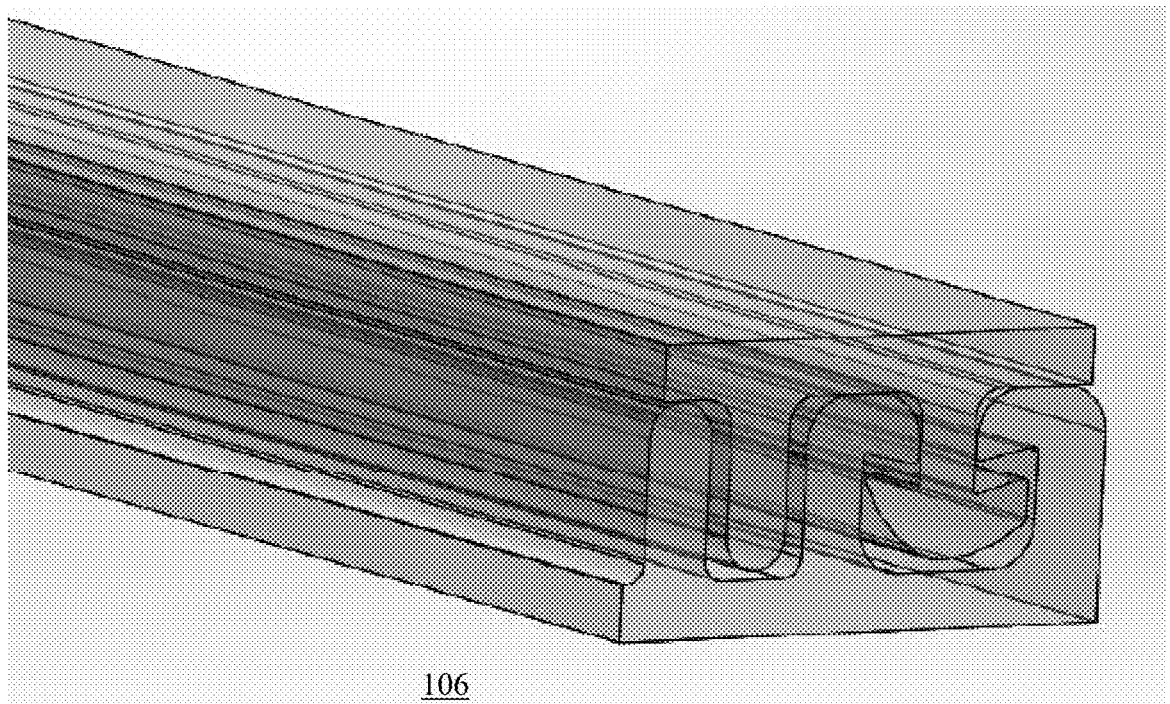
Figures 3, 4B:
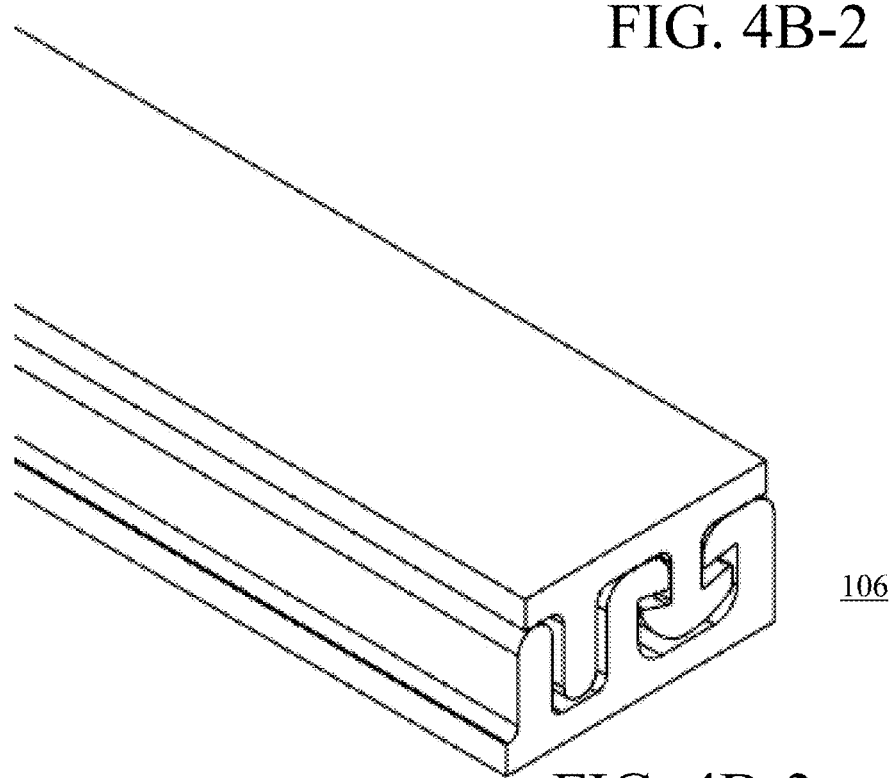
Figures 4, 4B:
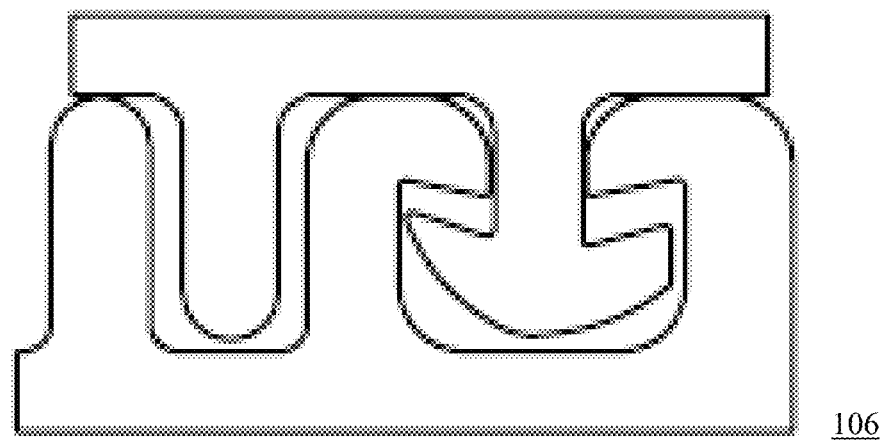
Figures 4, 4B, 5:
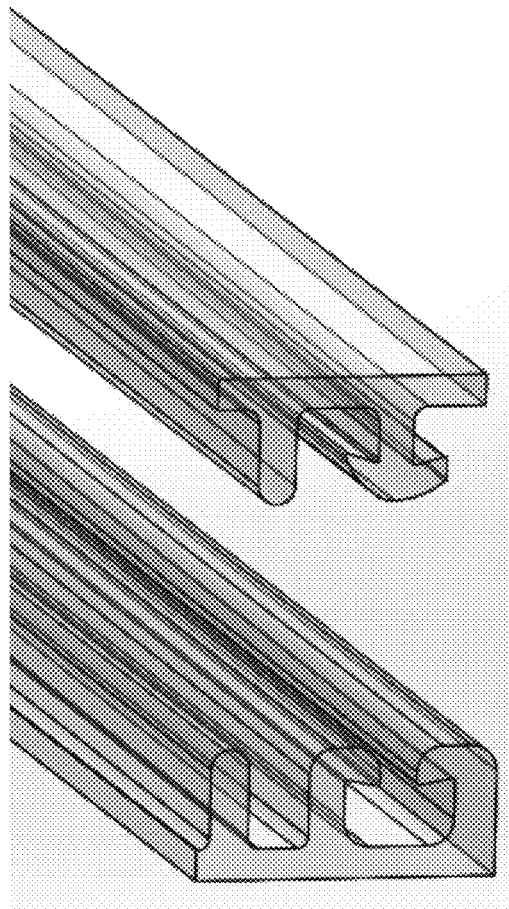
Figure 4C:
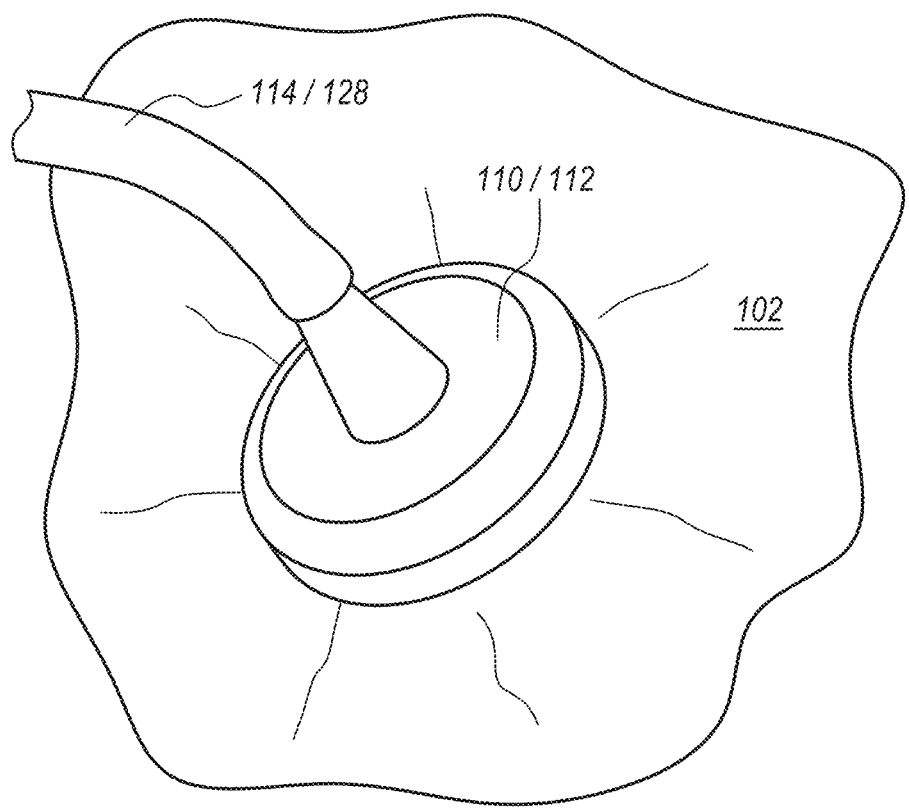
Figure 4D:
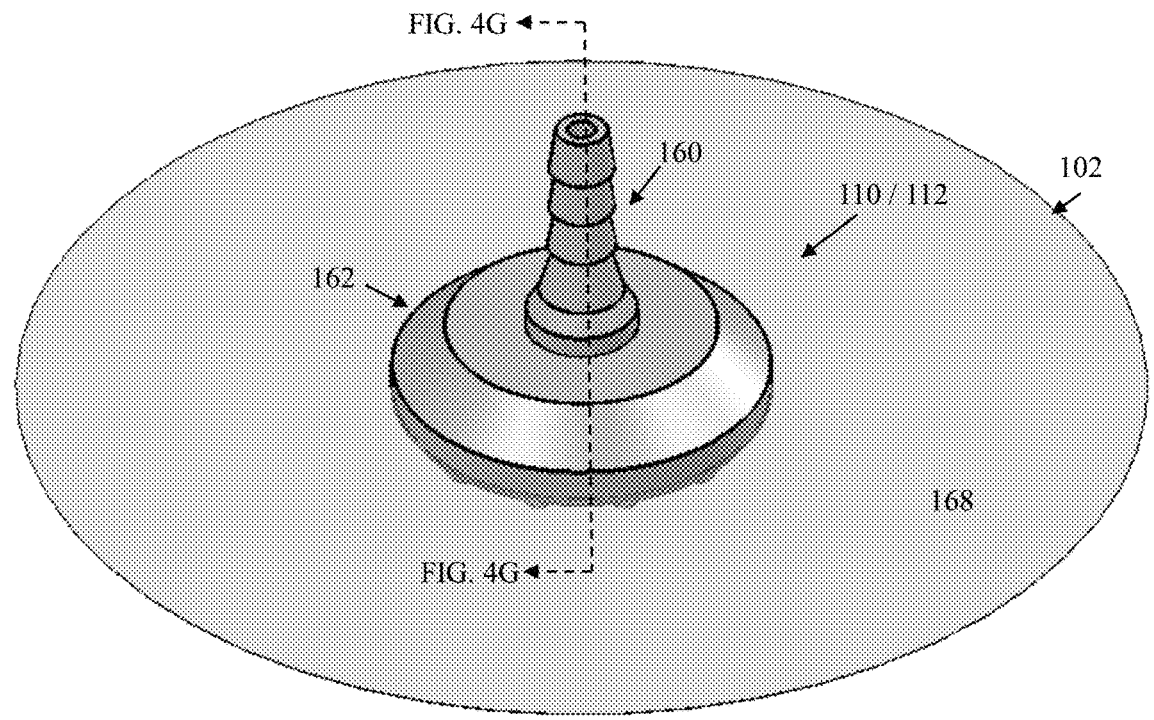
Figure 4E:
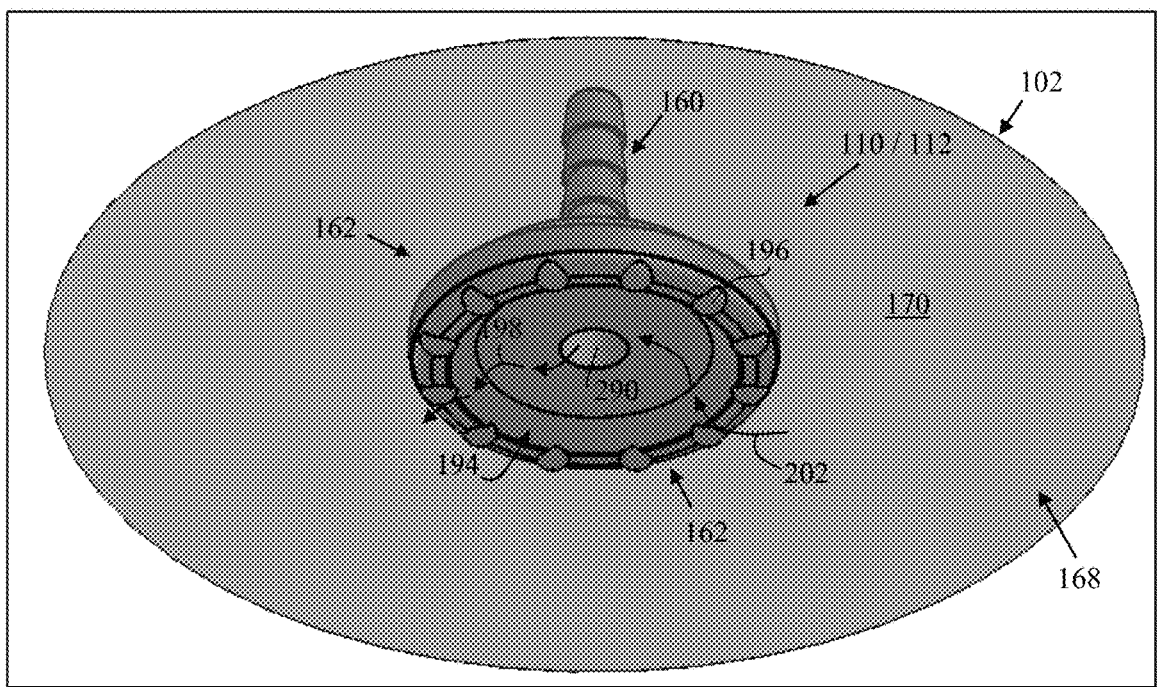
Figure 4F:
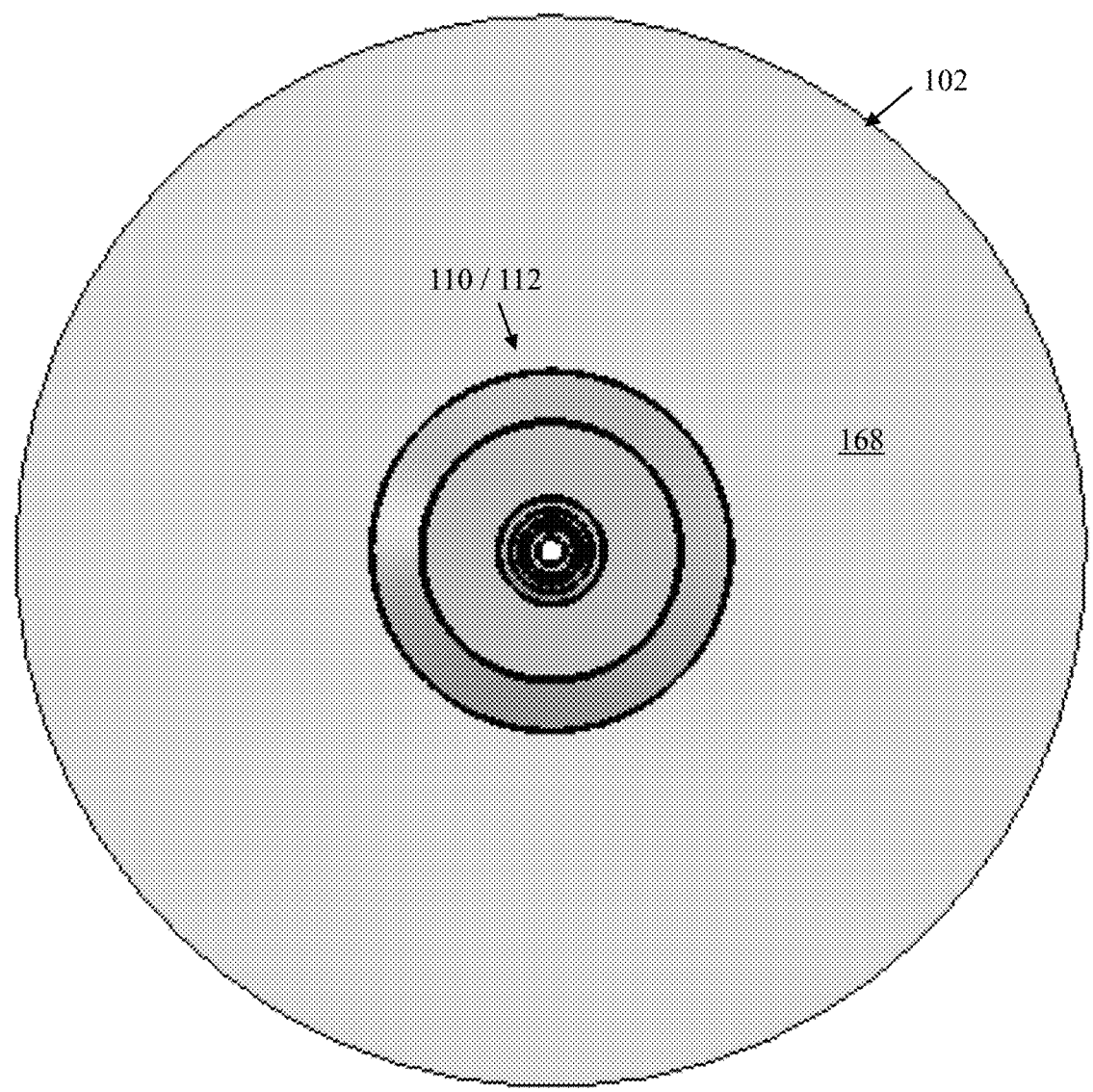
Figure 4G:
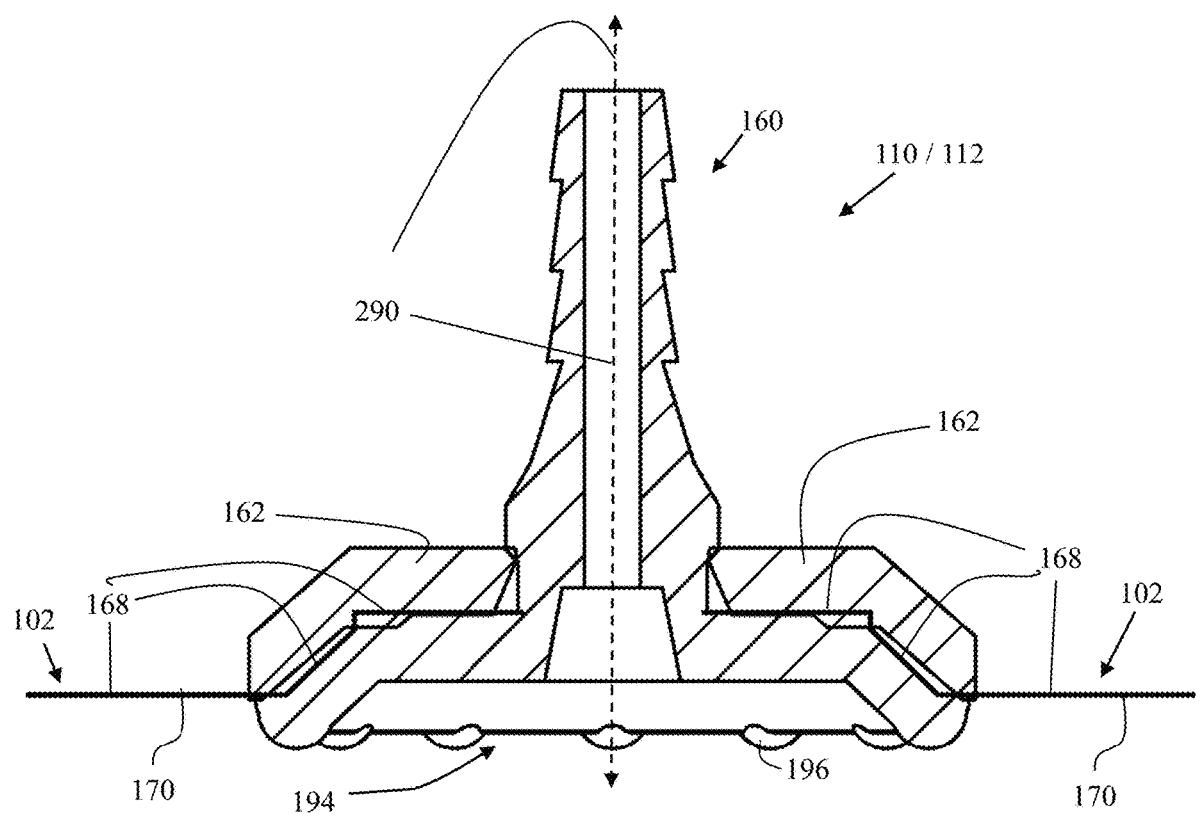
Figure 4H:
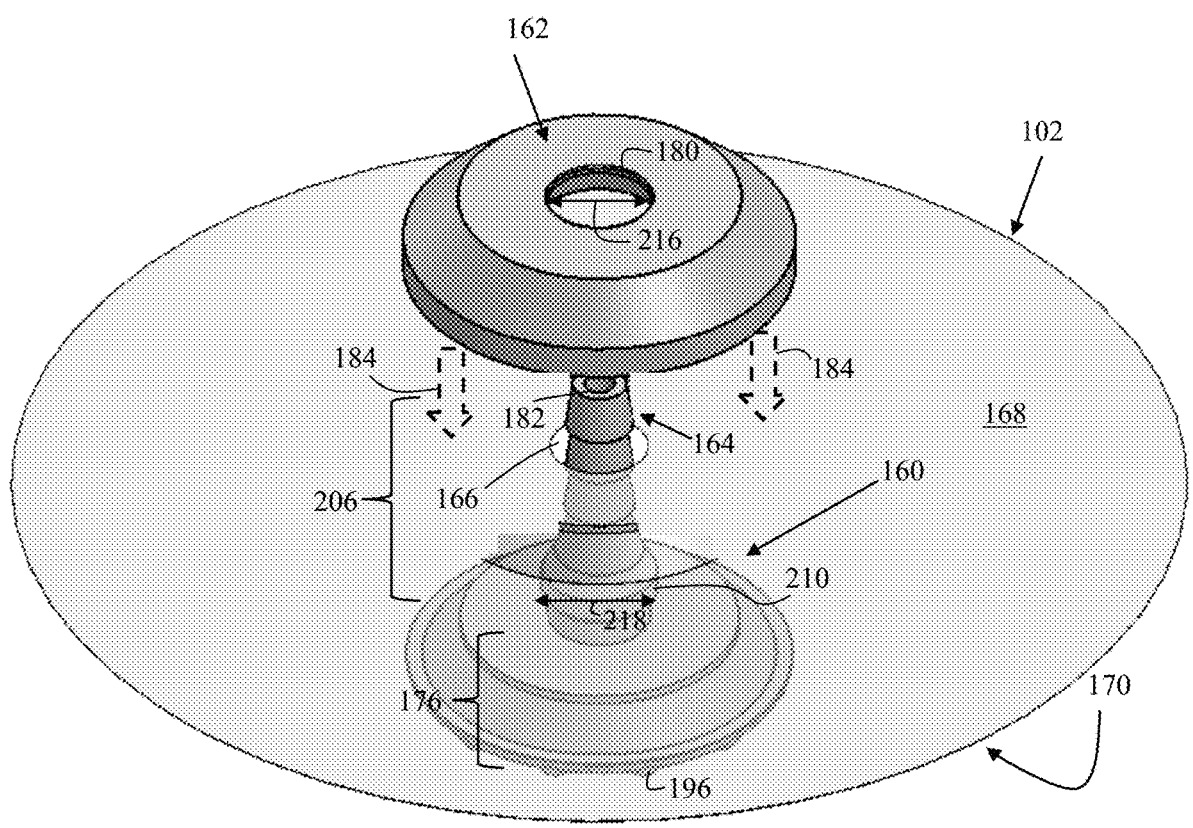
Figure 4I:
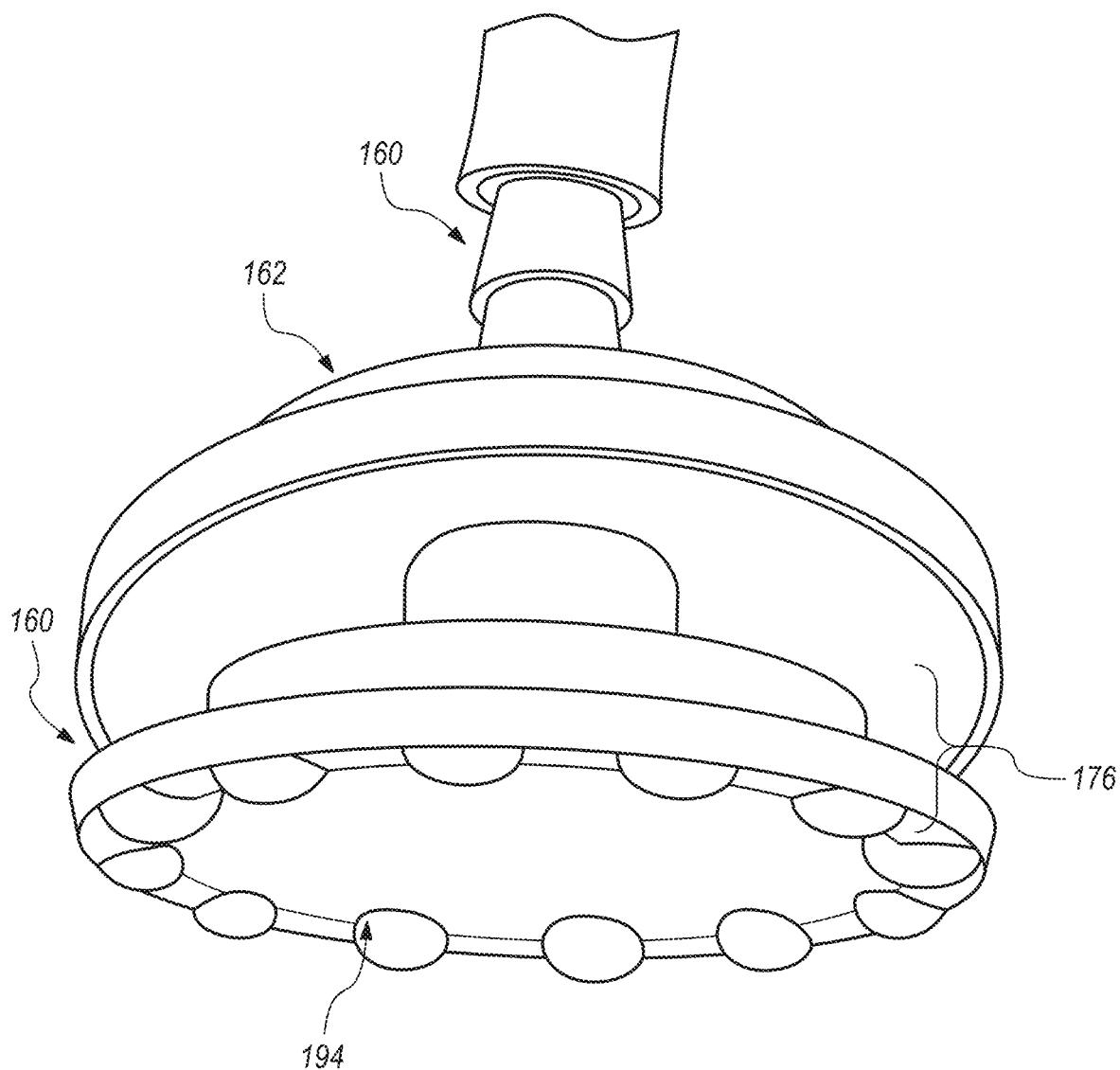
Figure 4J:
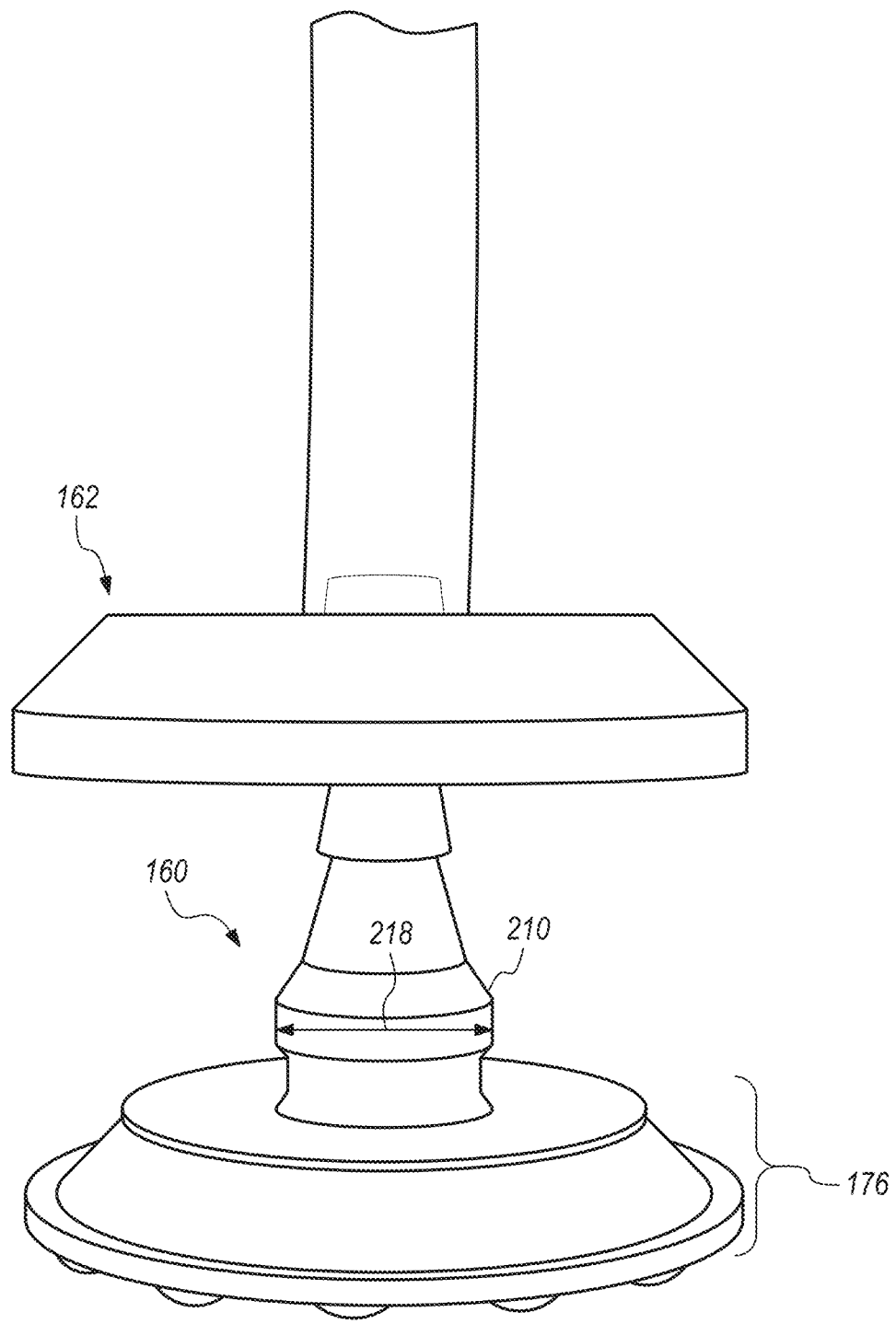
Figure 4K:
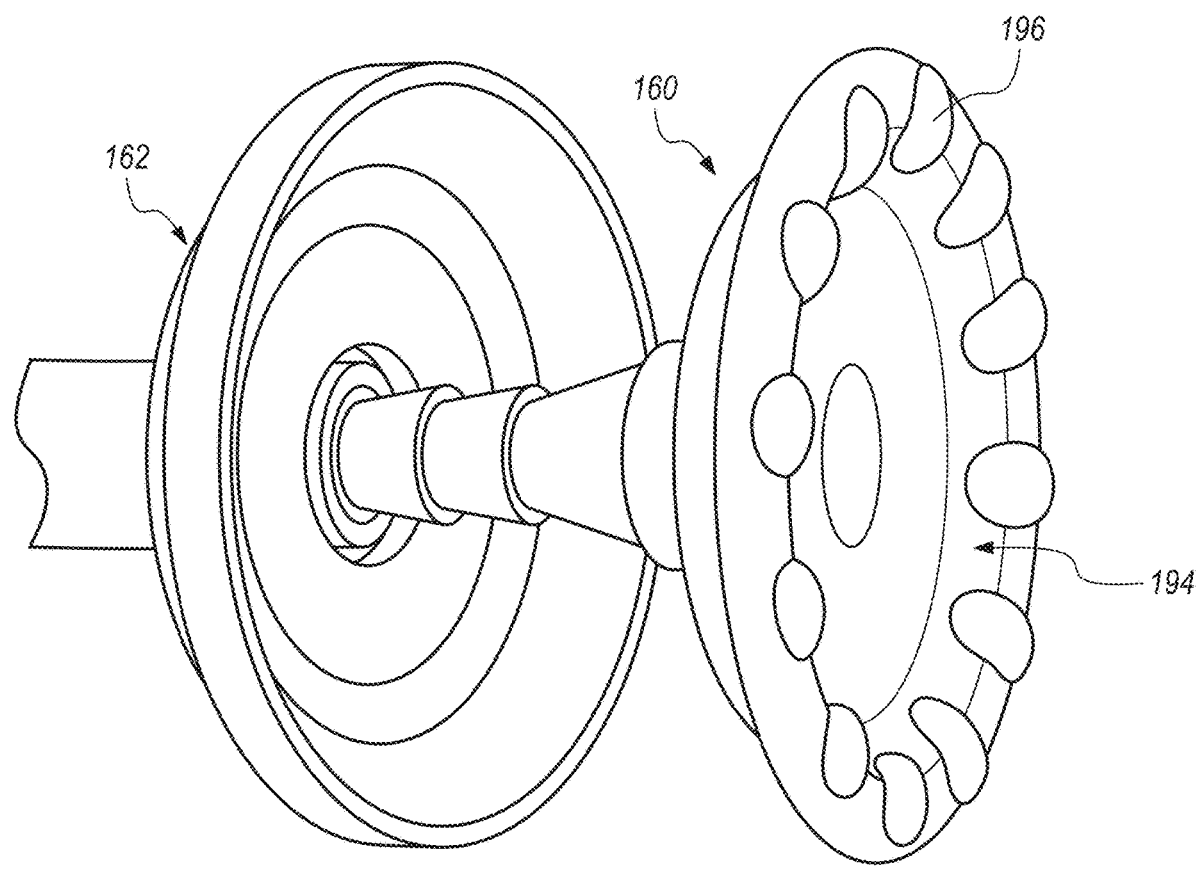
Figure 4L:
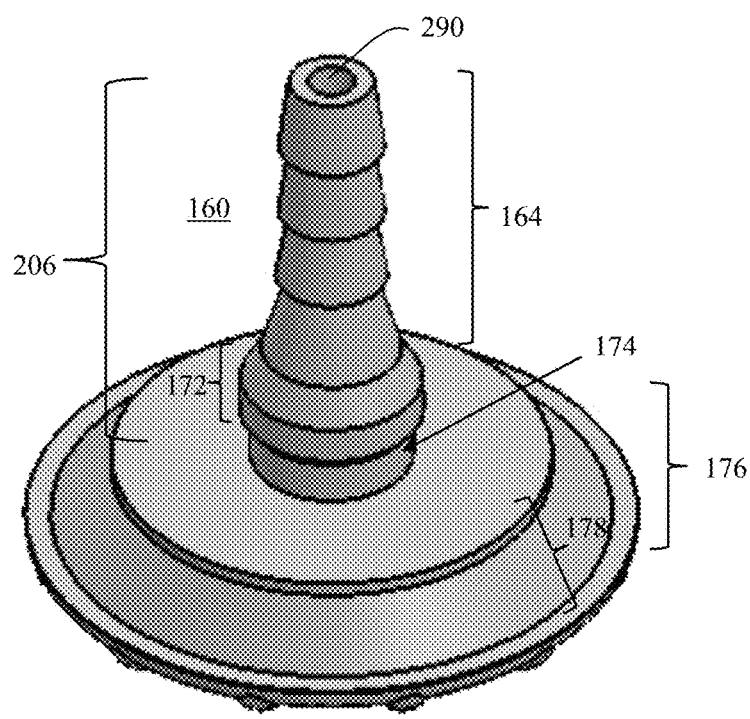
Figure 4M:
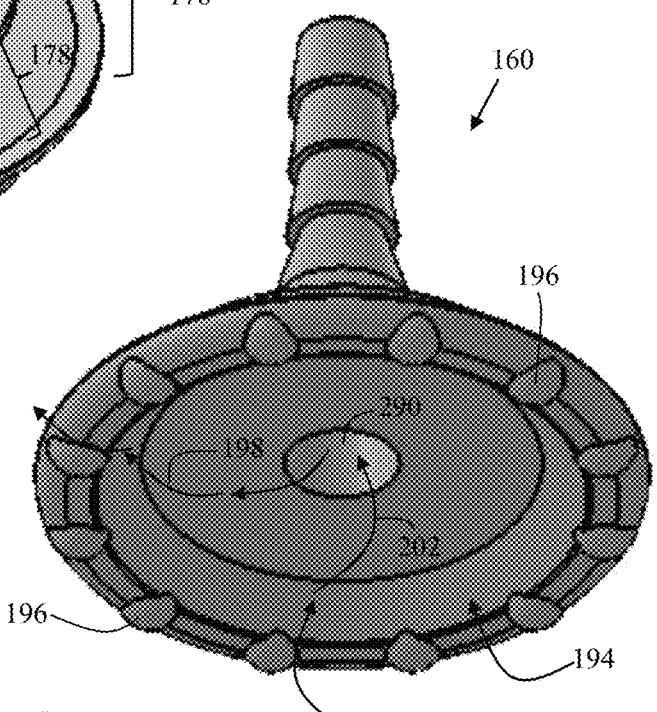
Figure 4N:
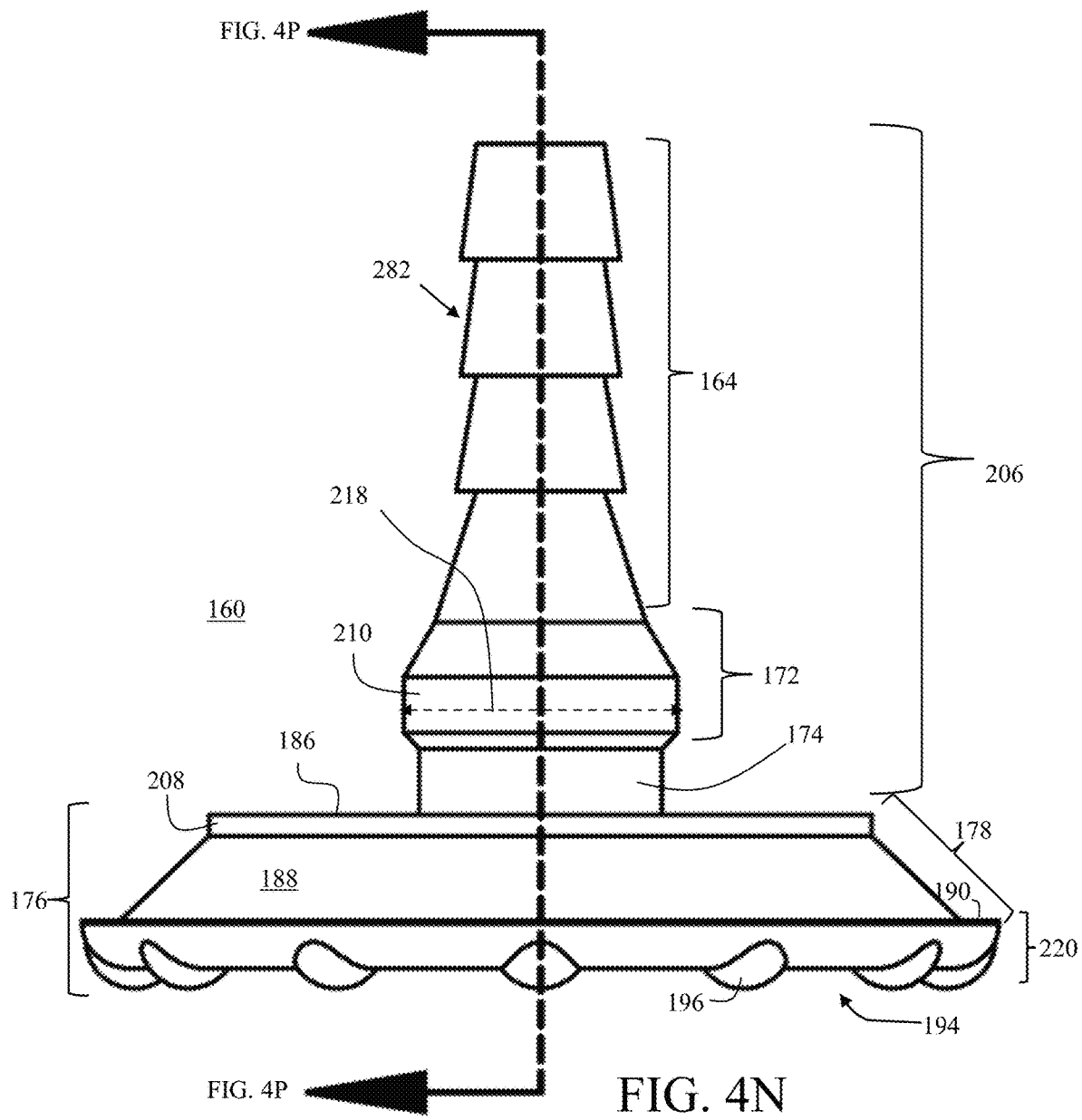
Figure 4O:
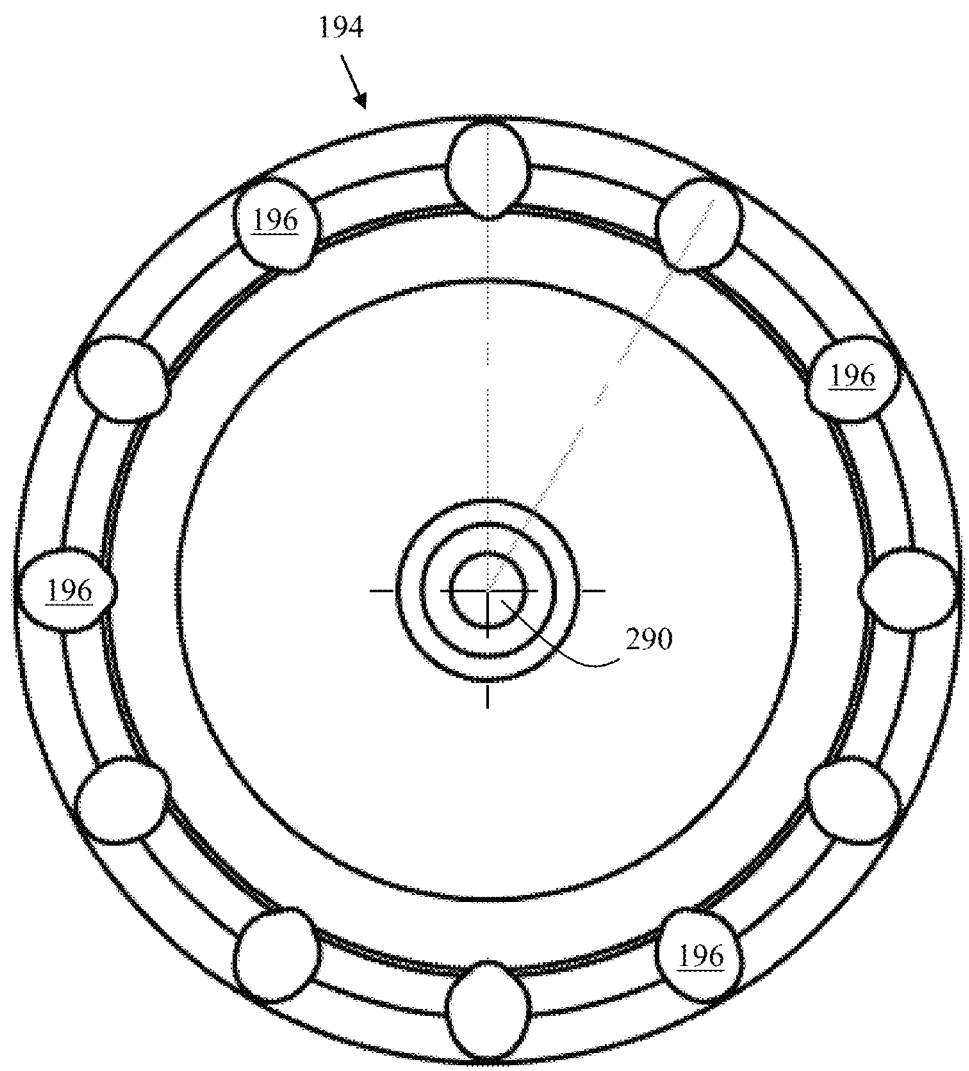
Figure 4P:
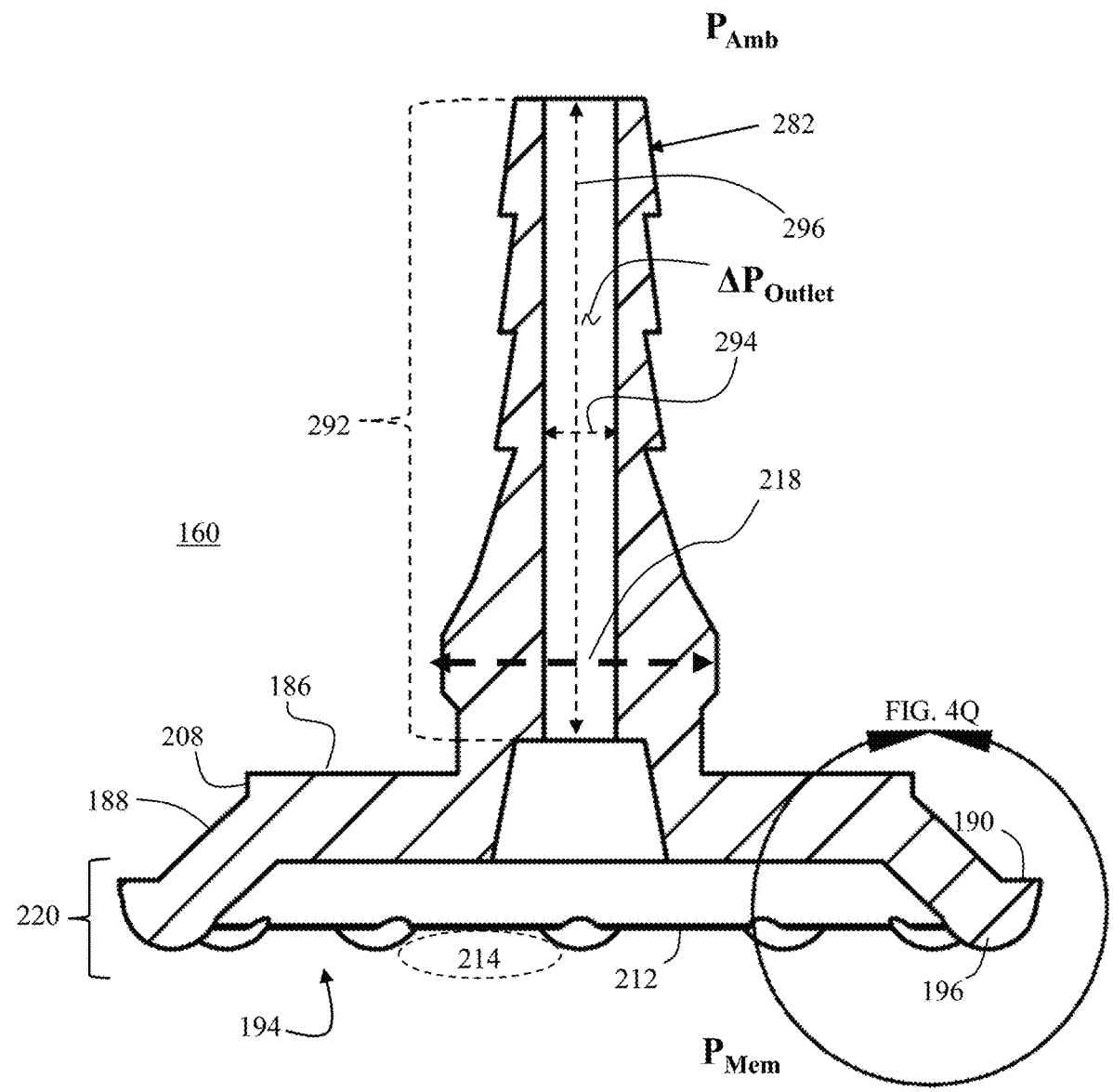
Figure 4Q:
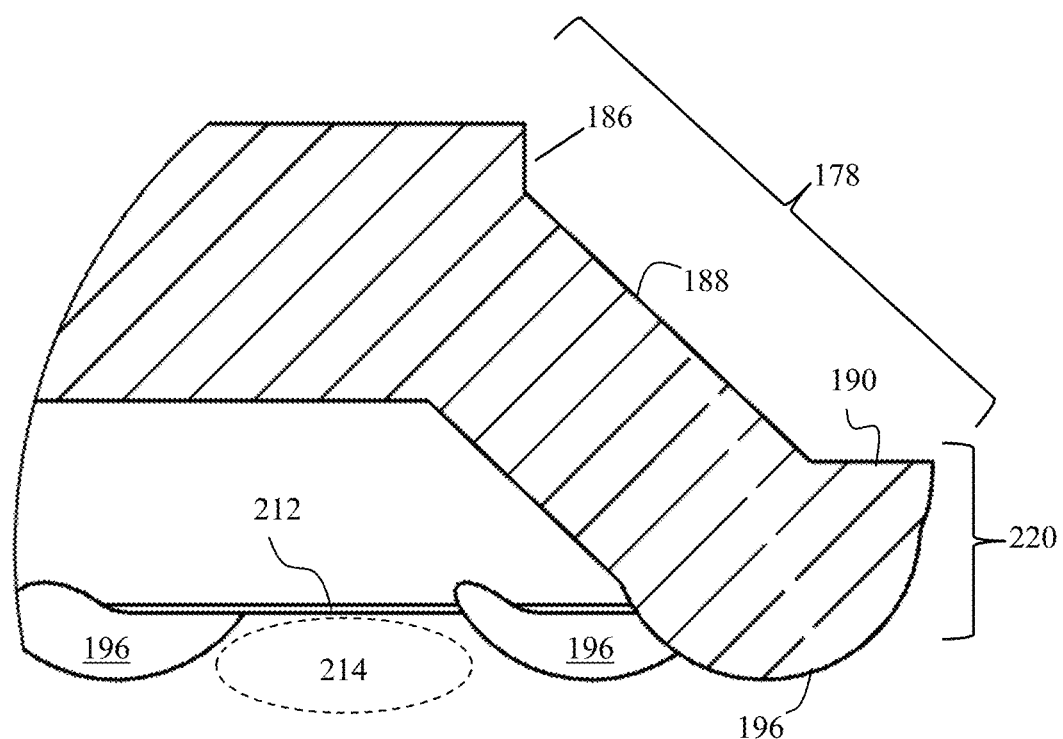
Figure 4T:
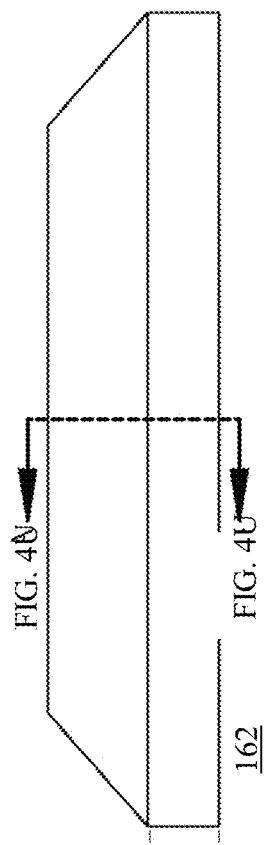
Figure 4U:
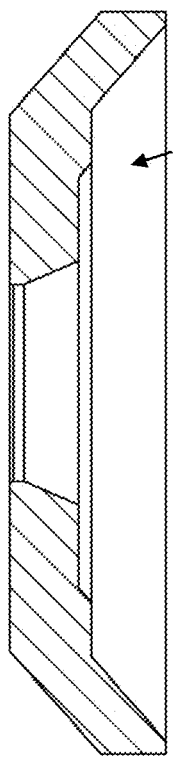
Figure 4R:
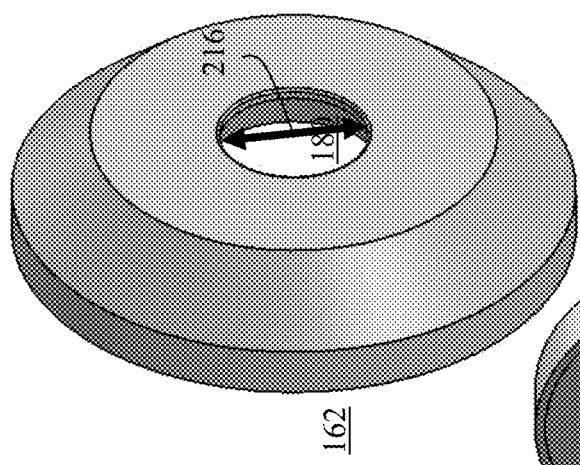
Figure 4S:
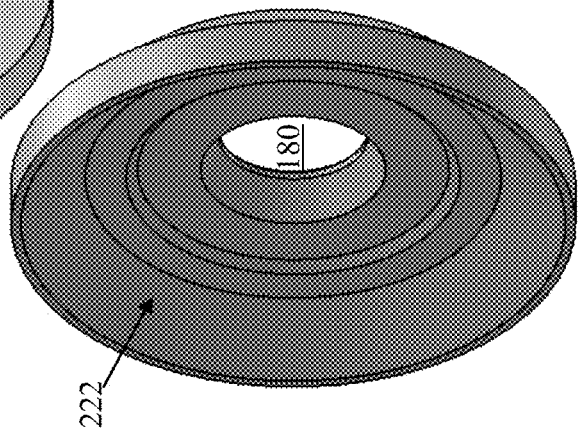
Figure 4V:
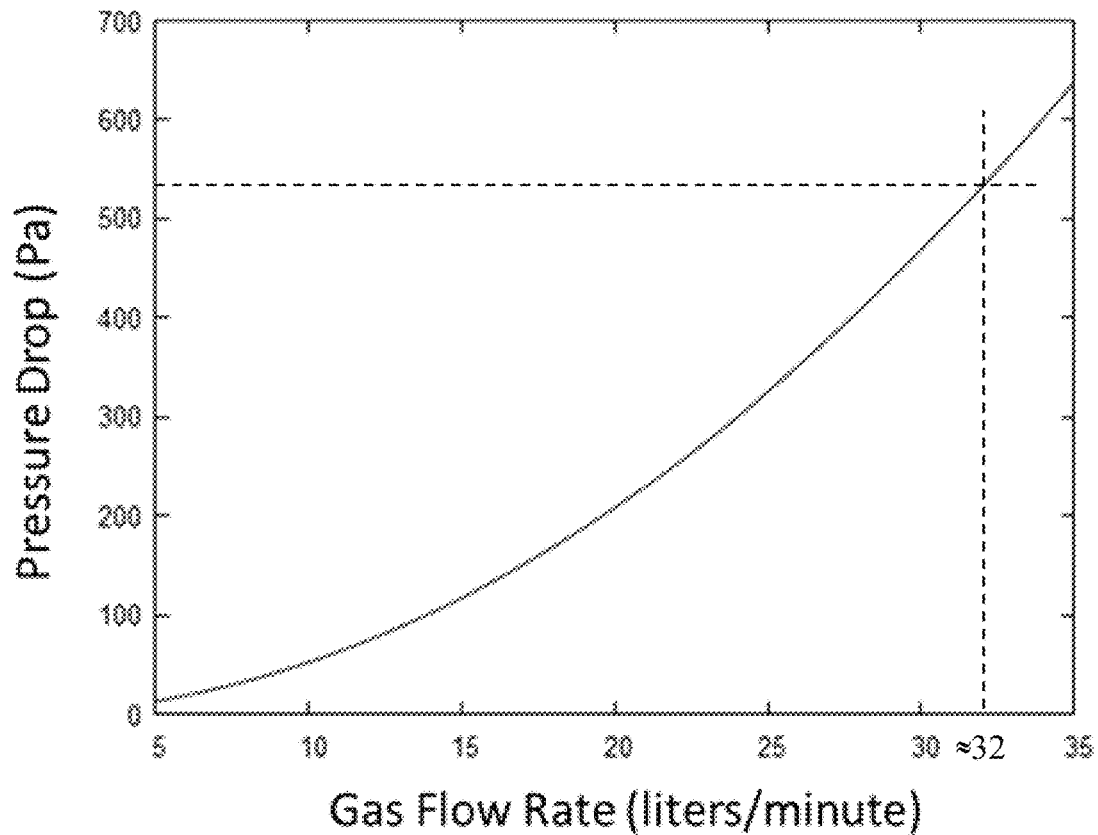
Figures 1, 5A:
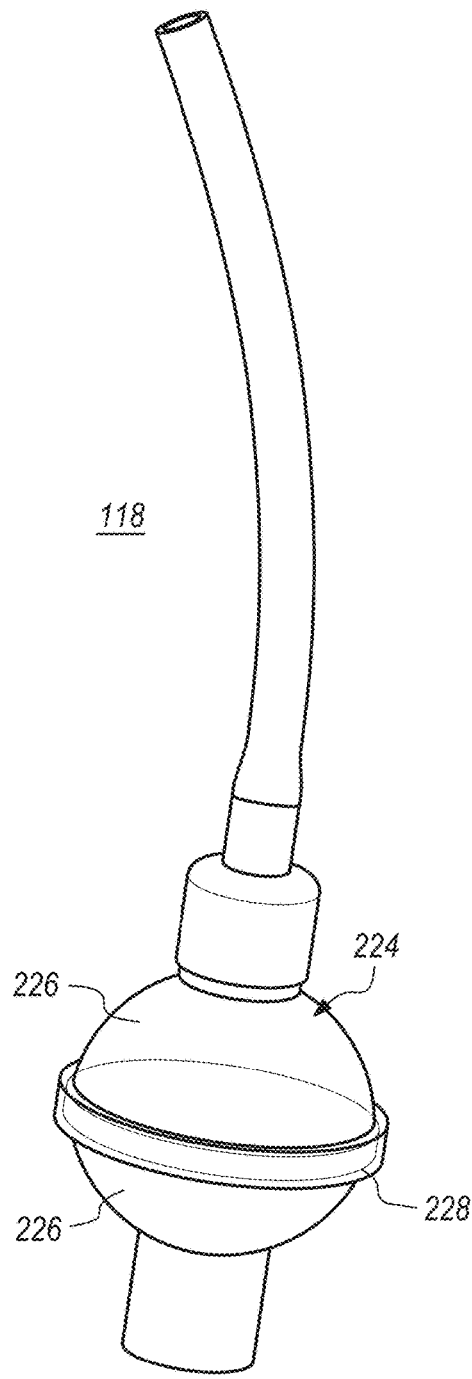
Figures 2, 5A:
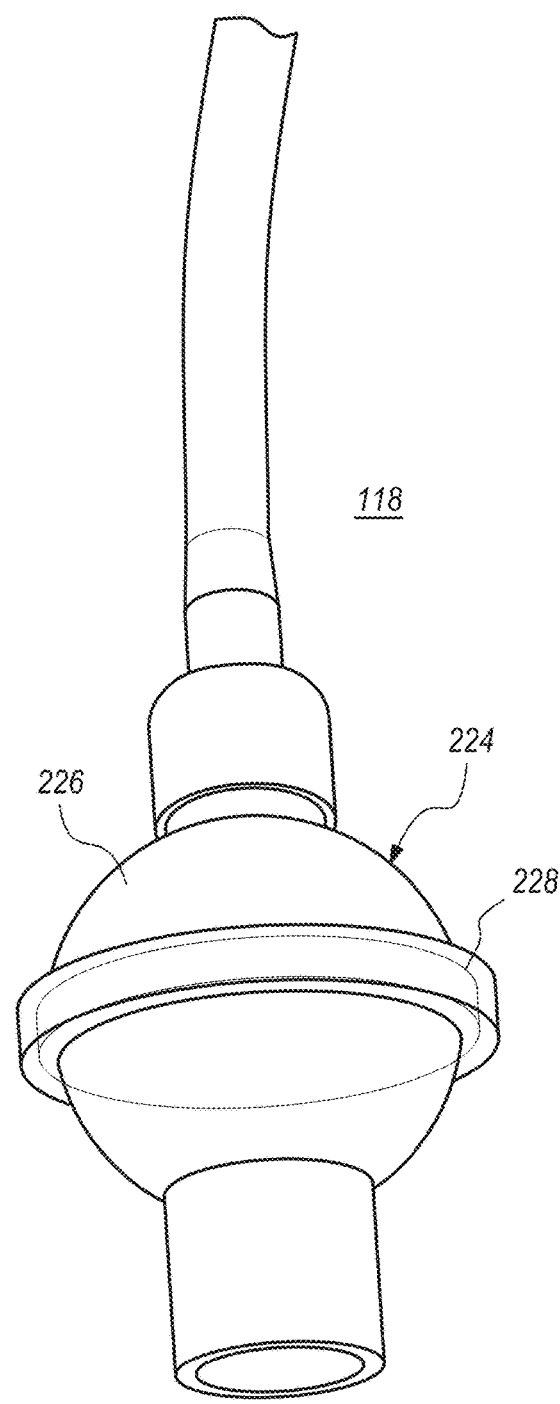
Figure 5B:
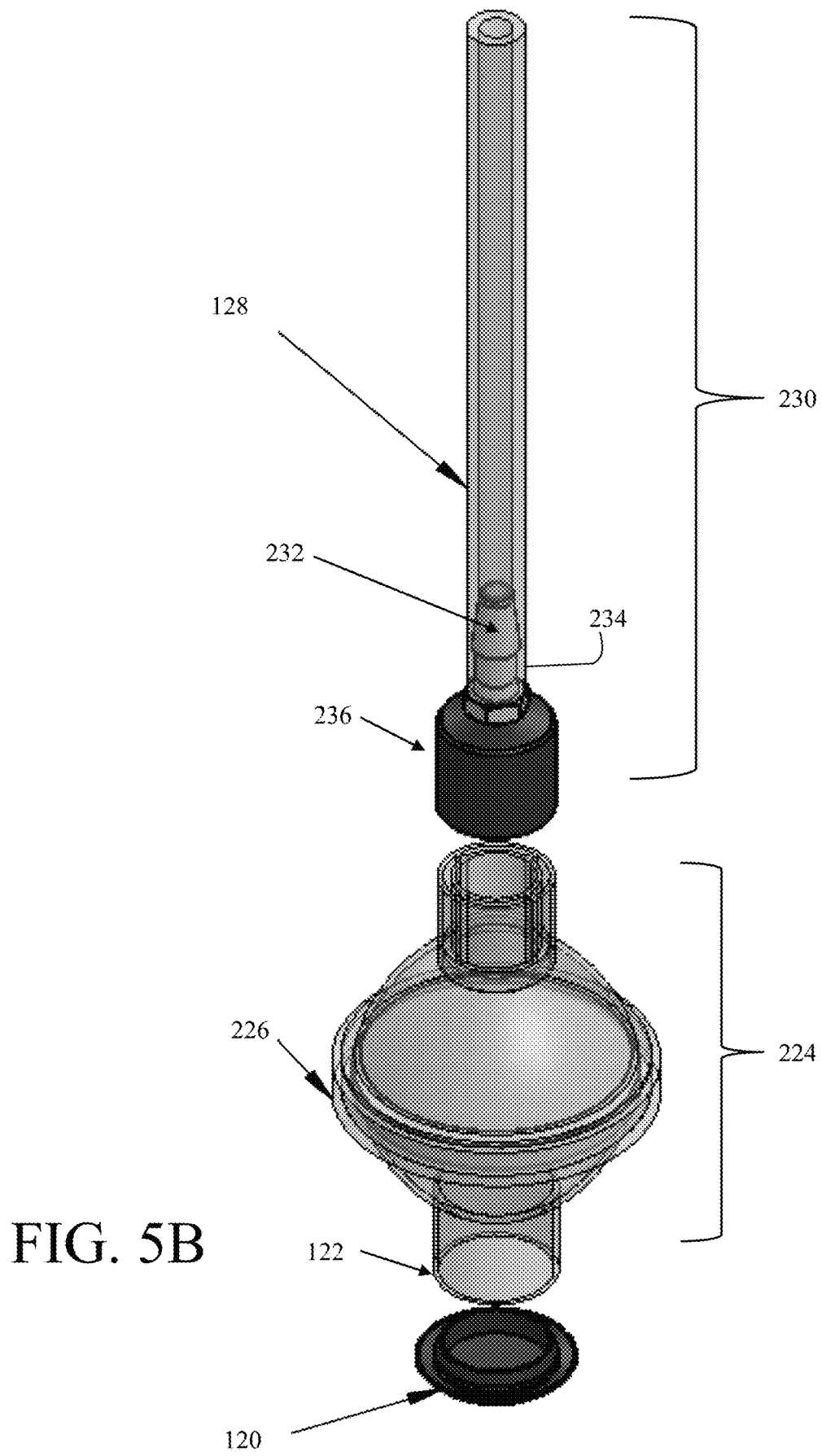
Figures 3, 5C:
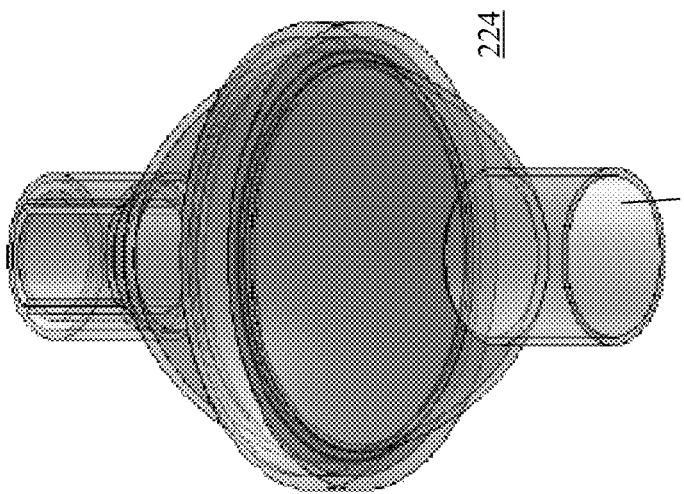
Figures 2, 5C:
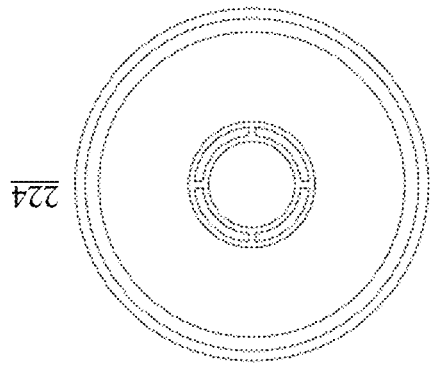
Figures 1, 5C:
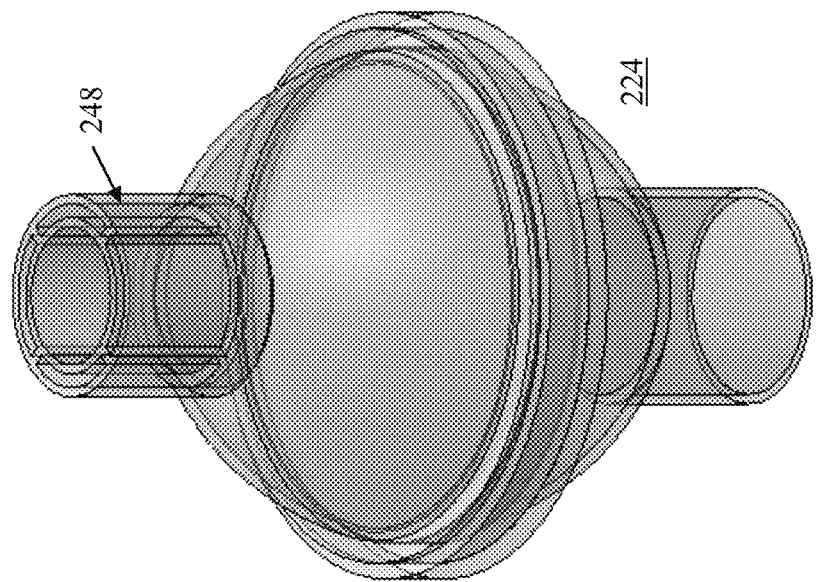
Figures 5, 5C, 6:
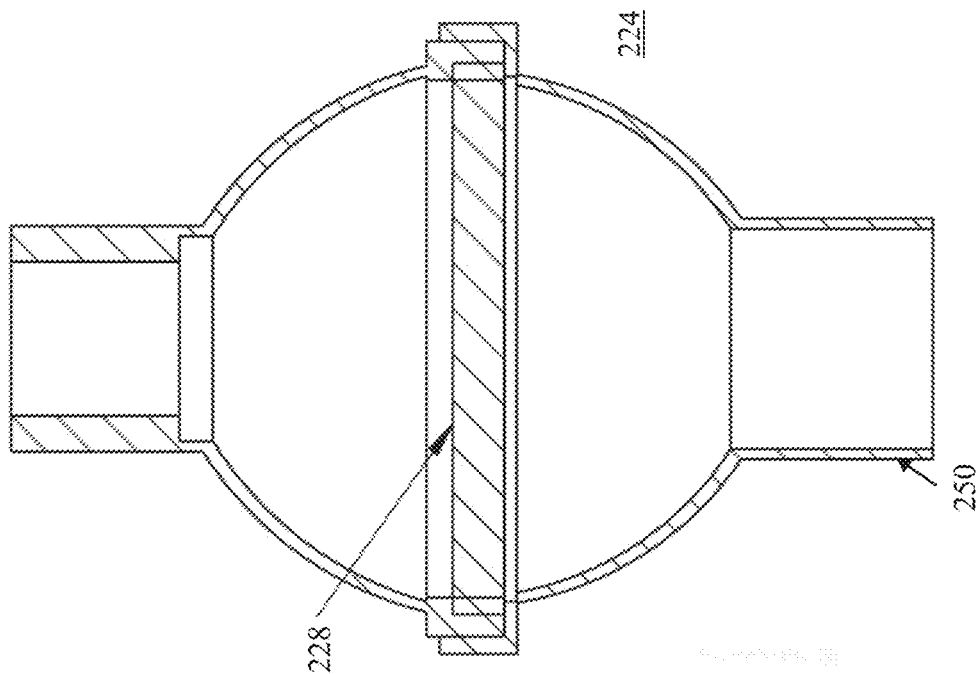
Figures 5, 5C:
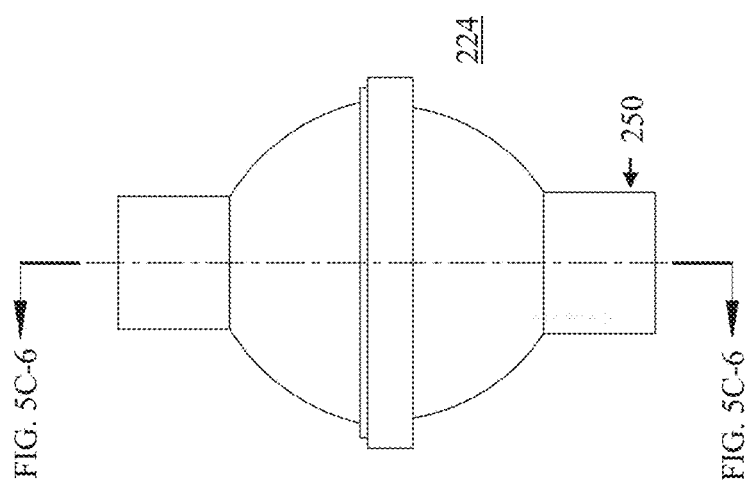
Figures 4, 5C:
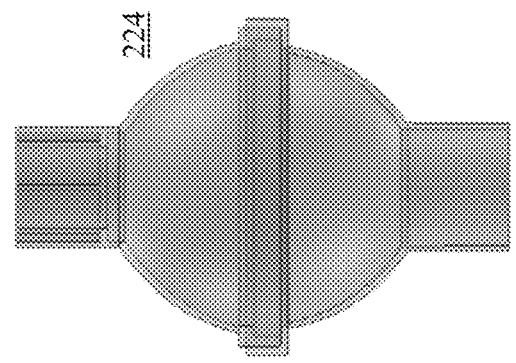
Figure 5F:
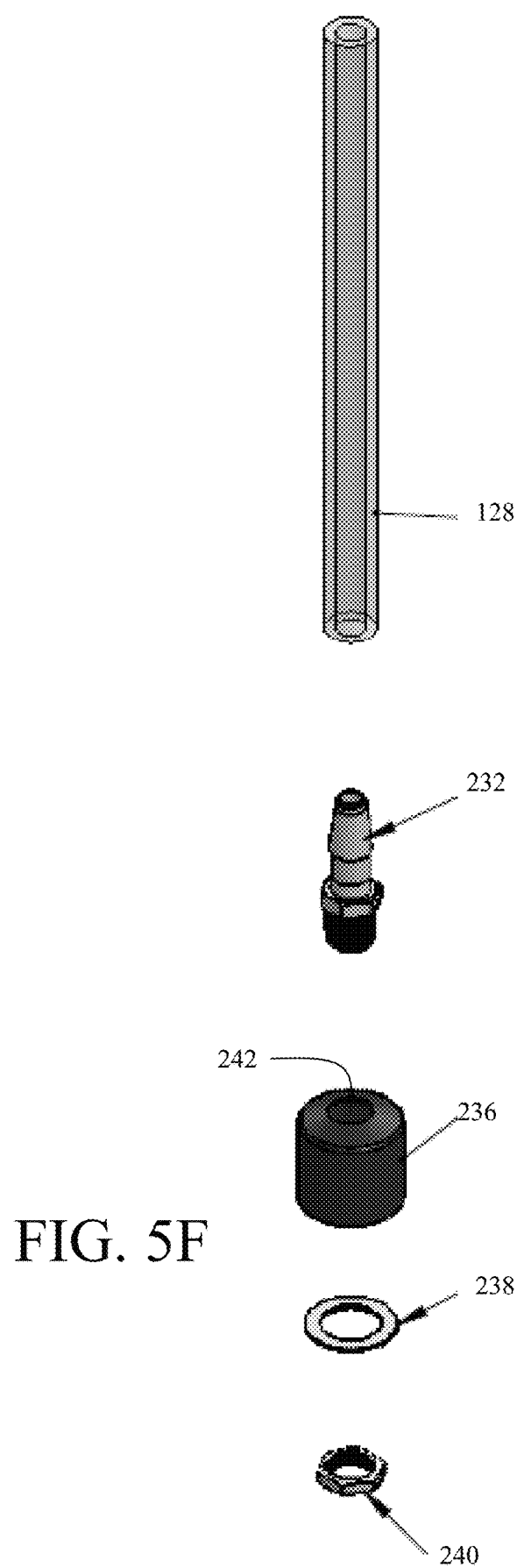
Figures 1, 5G:
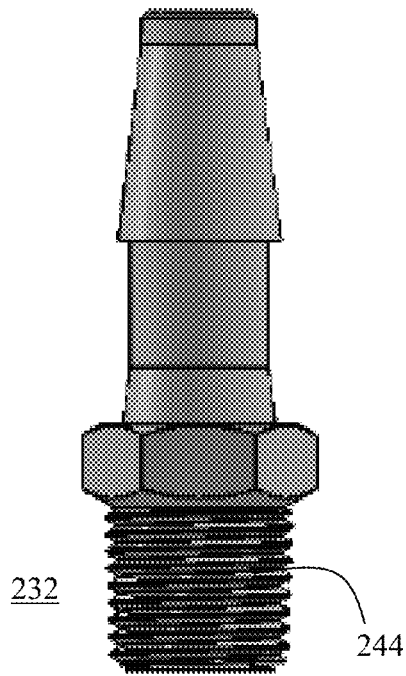
Figures 2, 5G:
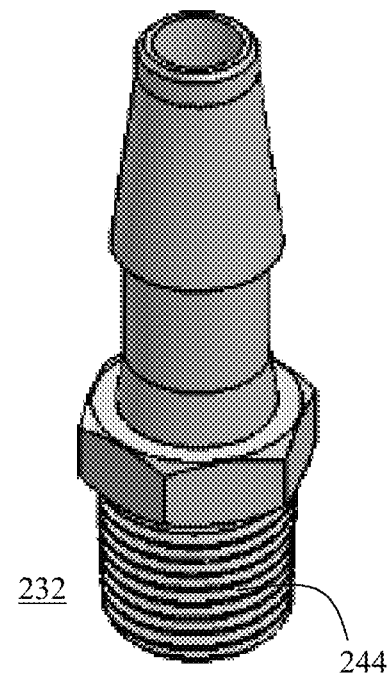
Figures 3, 5G:
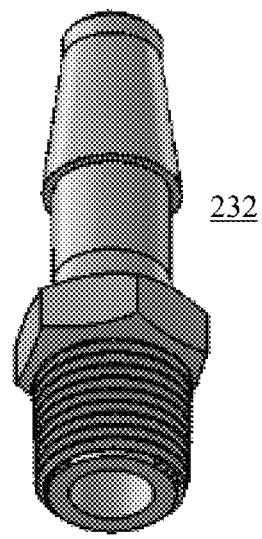
Figures 4, 5G:
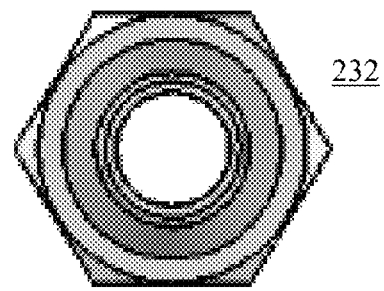
Figures 3, 5H:
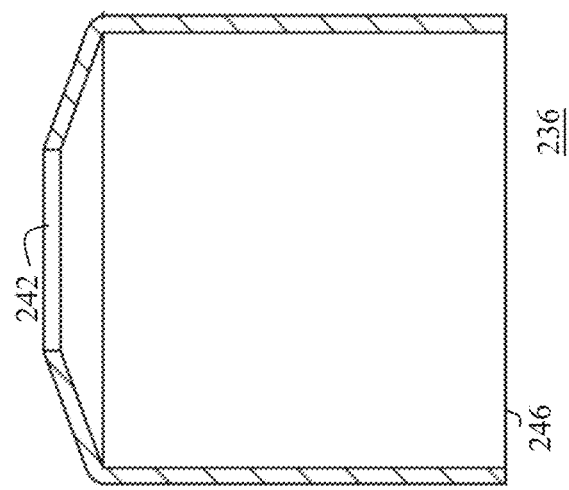
Figures 2, 5H:
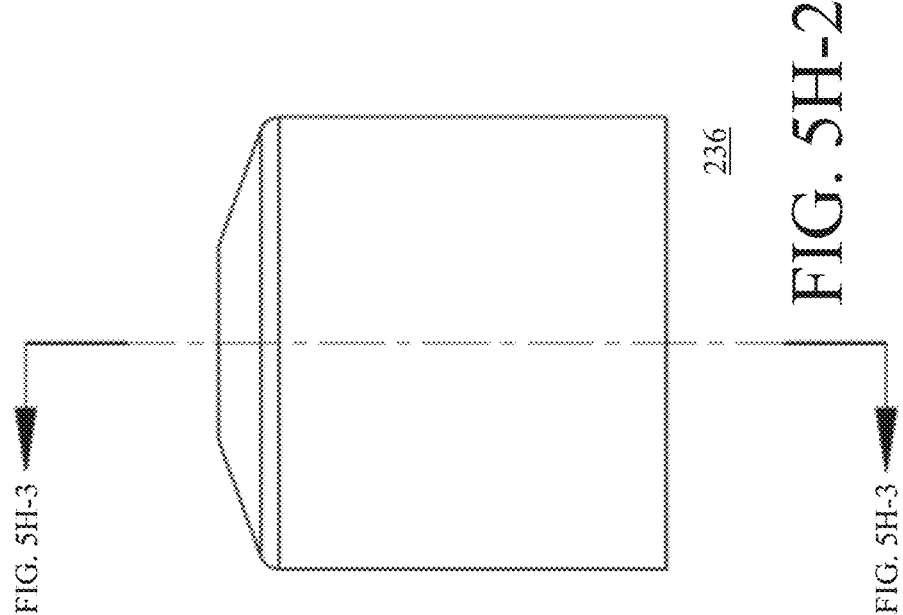
Figures 1, 5H:
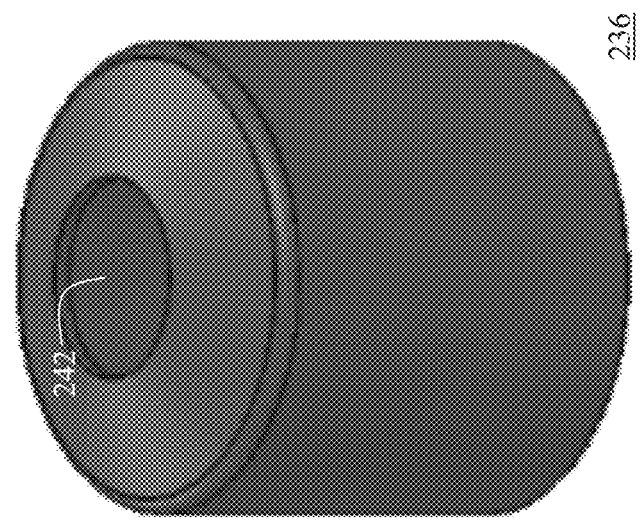
Figures 1, 5I:
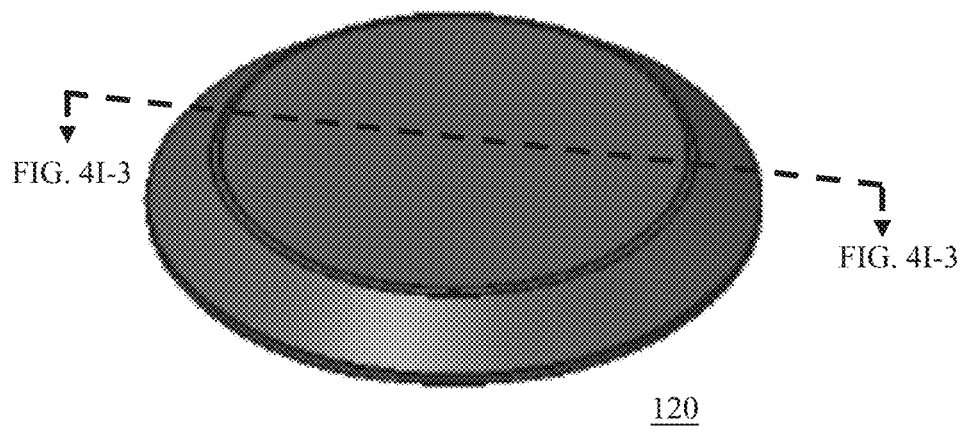
Figures 2, 5I:
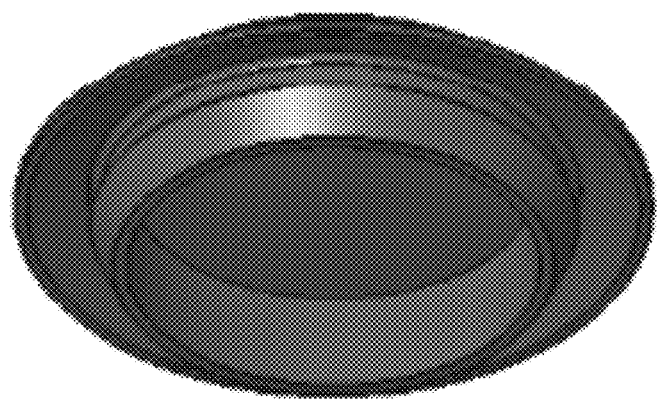
Figures 3, 5I:
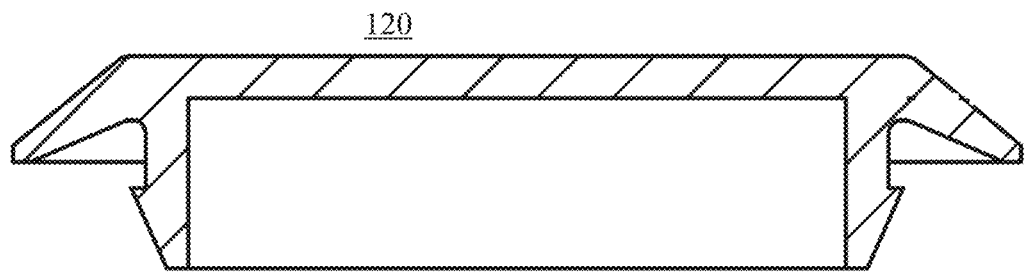

FIGS. 4A to 4V are a non-limiting, exemplary illustration of the isolation system of FIGS. 1A to 3B, with deflated (but unfurled) polyethylene membrane, including individual associated components in accordance with one or more embodiments of the present invention.

As illustrated in FIGS. 1A to 4V, membrane 102 is a transparent, flexible, portable, disposable sheet material comprised of polyethylene with an average thickness of about 0.102 mm.

The polyethylene membrane 102 is comprised of a thermally sealed sheet material with a single access opening 104, forming an enlarged sheet material plastic (medical grade polyethylene) bag. Single access opening 104 has a length 136 oriented along a transverse axis 130 of the polyethylene membrane 102. Membrane 102 meets or exceed requirements of IEST-STD 1246D Level 100 and is FDA approved.

Membrane 102 further includes thermally sealed lateral sides 138 and 140 that extend longitudinally from a thermally sealed end 142 to single access opening 104, along a central longitudinal axis 144 of membrane 102, with central longitudinal axis 144 defining overall length 154 of the polyethylene membrane 102.

Thermally sealed lateral sides 138 and 140 diverge away from central longitudinal axis 144 near single access opening 104 at a divergent angle Ω, defining a wider span opening length 136, with the span of length 136 of single access opening 104 greater than a span of a width 150 (defined along transverse axis 130) of the polyethylene membrane 102. Accordingly, width 150 of the polyethylene membrane 102 is substantially constant along central longitudinal axis 144 of the polyethylene membrane 102 starting from thermally sealed end 142 but increases near single access opening 104. Wider access opening 106 facilitates for ease of entry of a patient 108 into isolation membrane 102.

Thermally sealed lateral sides 138 and 140 may be identical, mirror images, and may include identical, longitudinally extending pleats 146 and 148 for facilitating an expansion of the polyethylene membrane 102 when inflated. It should be noted that the number of pleats may be increased to more than the two shown.

Pleats 146 and 148 have a transversely oriented separation distance 152 that decrease in span from thermally sealed end 142, with both pleats 146 and 148 converging at single access open side 104. Non-limiting example of separation distance 152 of pleats 146 and 148 at or near thermally seal end 142 is about 12.7 cm. Non-limiting example of length 154 of the polyethylene membrane 102 is about 259 cm, with width 150 of about 96.5 cm, with opening 104 having length 136 of about 123 cm.

Figures 1, 1D, 2, 3, 4:
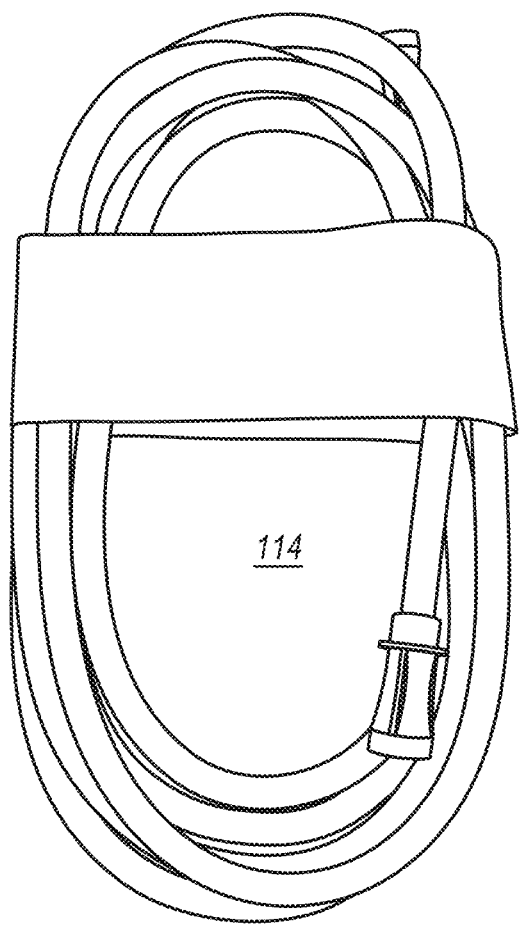
Figures 1, 1D, 2, 3, 4, 5:
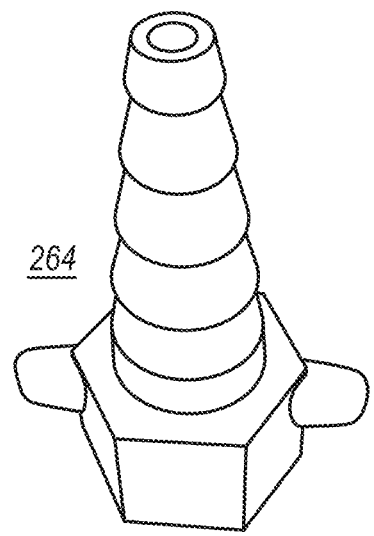
Figures 1, 1D, 2, 3, 4, 5, 6:
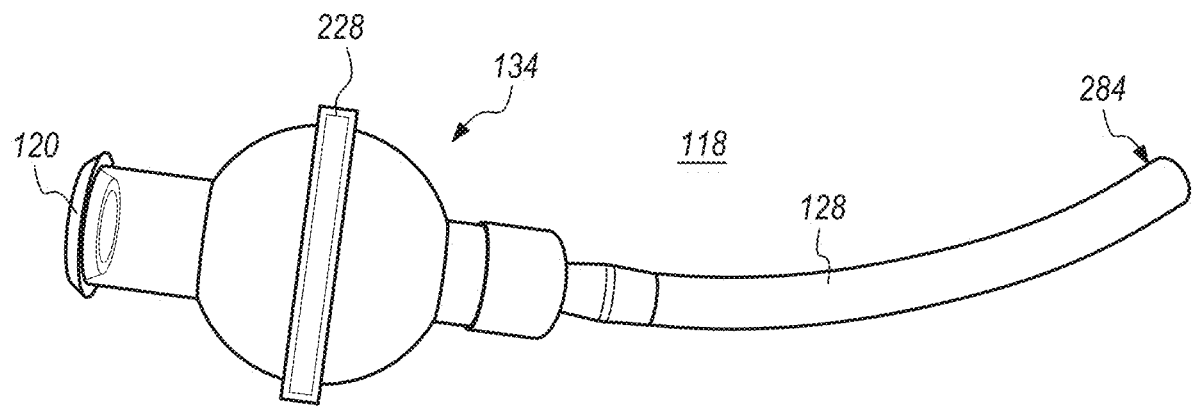
Figures 1, 1D, 2, 3, 4, 5, 6, 7:
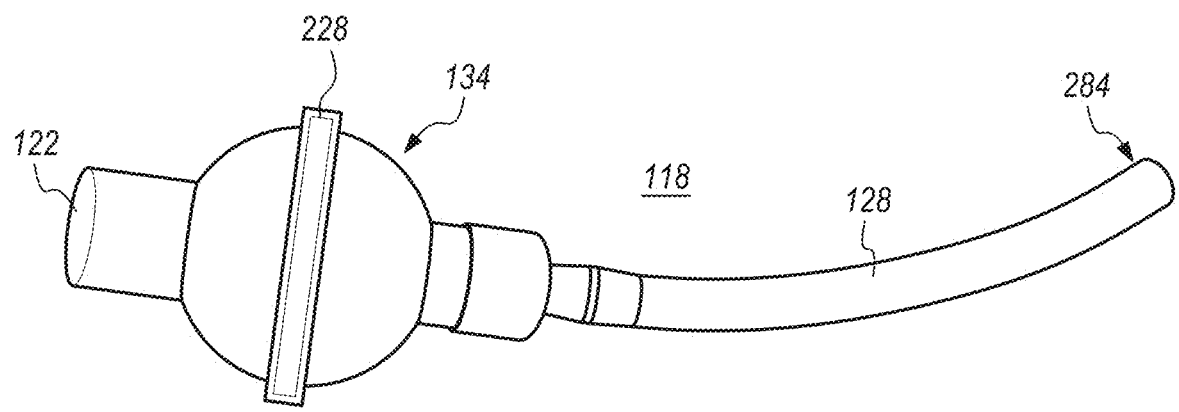
Figures 1, 1D, 2, 3, 4, 5, 6, 7, 8:
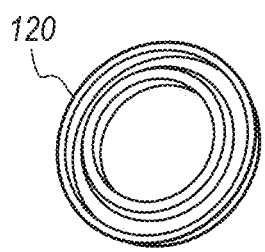
Figures 1, 1E:
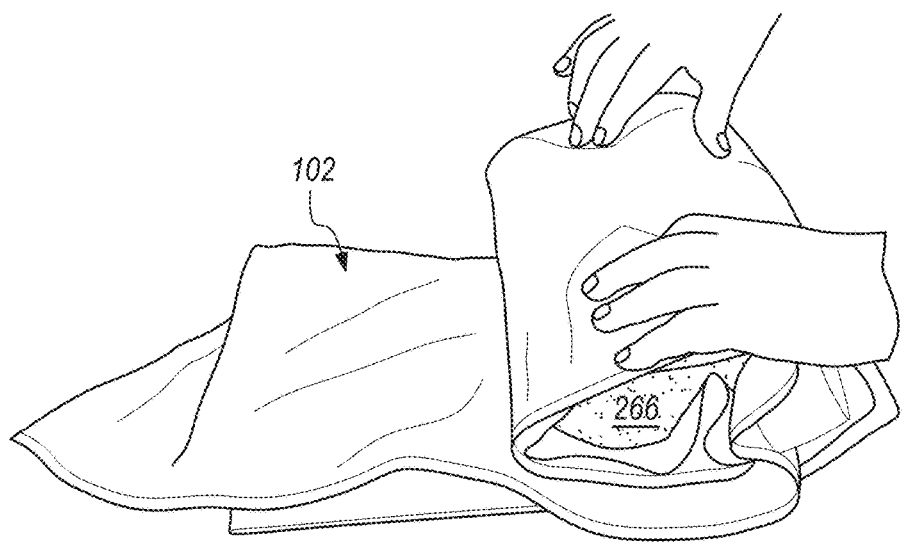
Figures 1, 1E, 2:
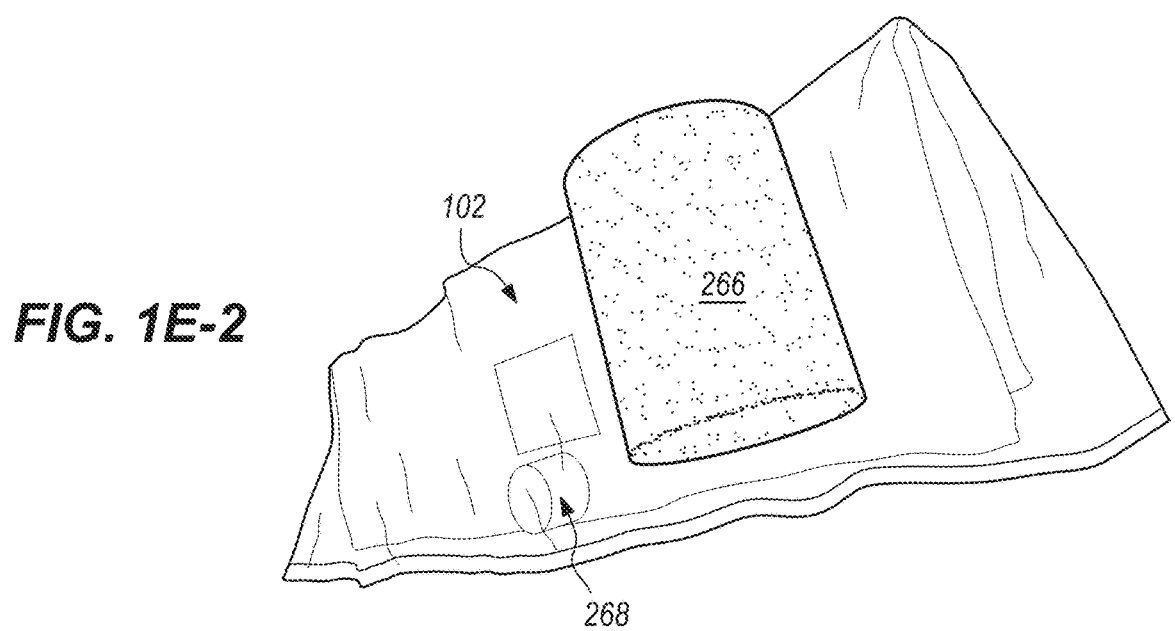
Figures 1, 1E, 2, 3:
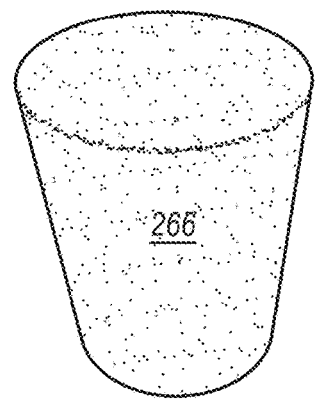
Figures 1, 1E, 2, 3, 4:
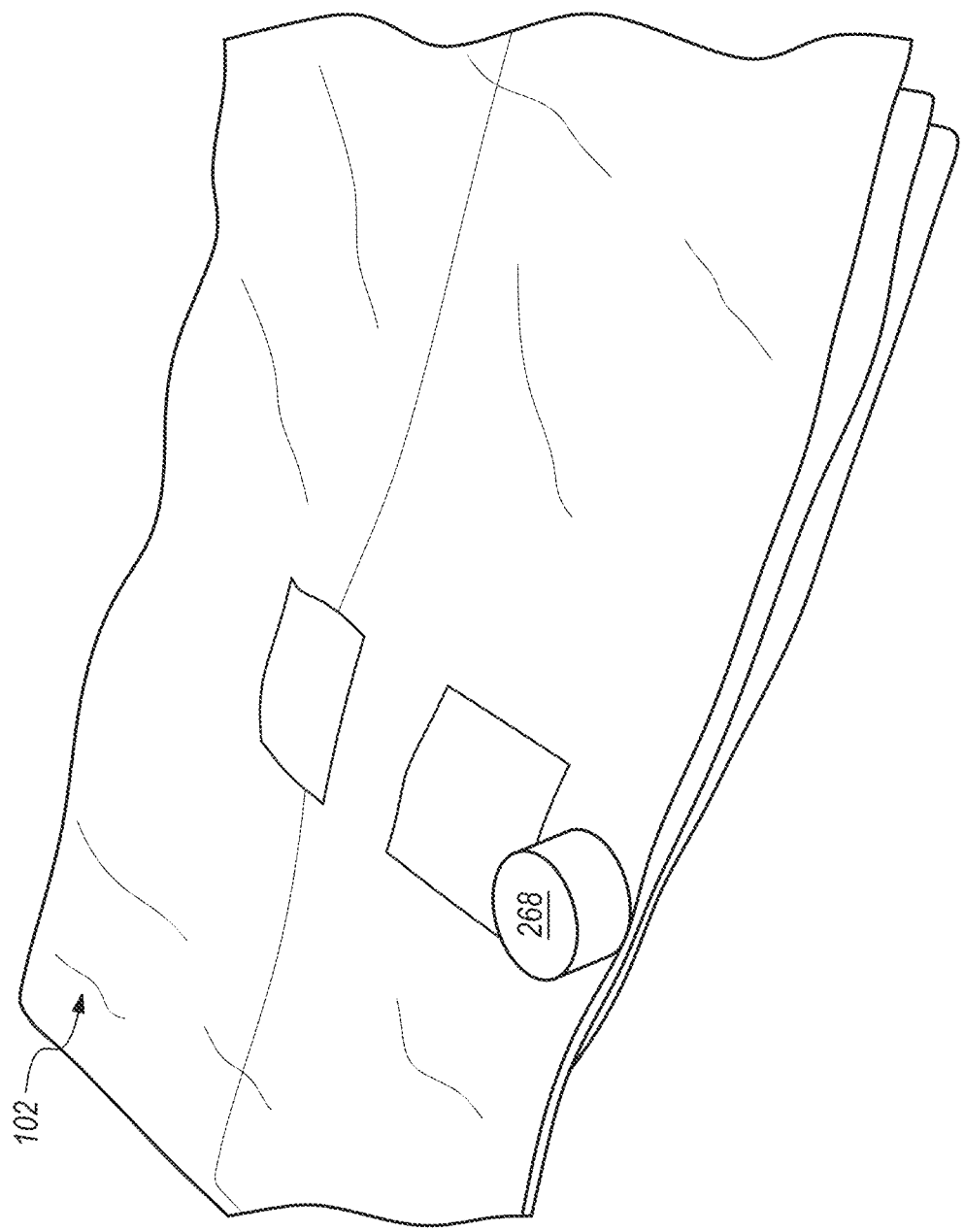
Figures 1, 1E, 2, 3, 4, 5:
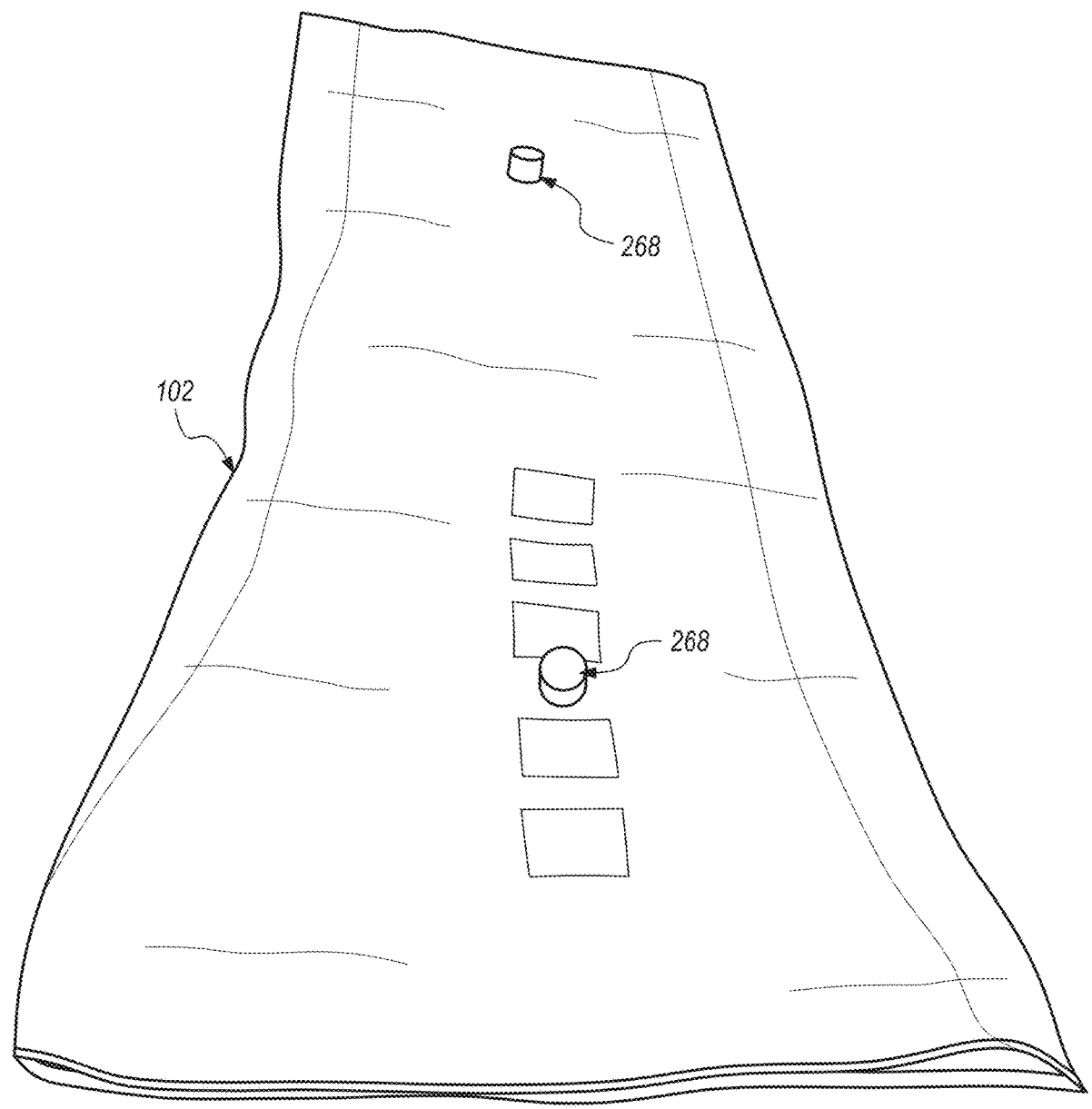
Figures 1, 1E, 2, 3, 4, 5, 6:
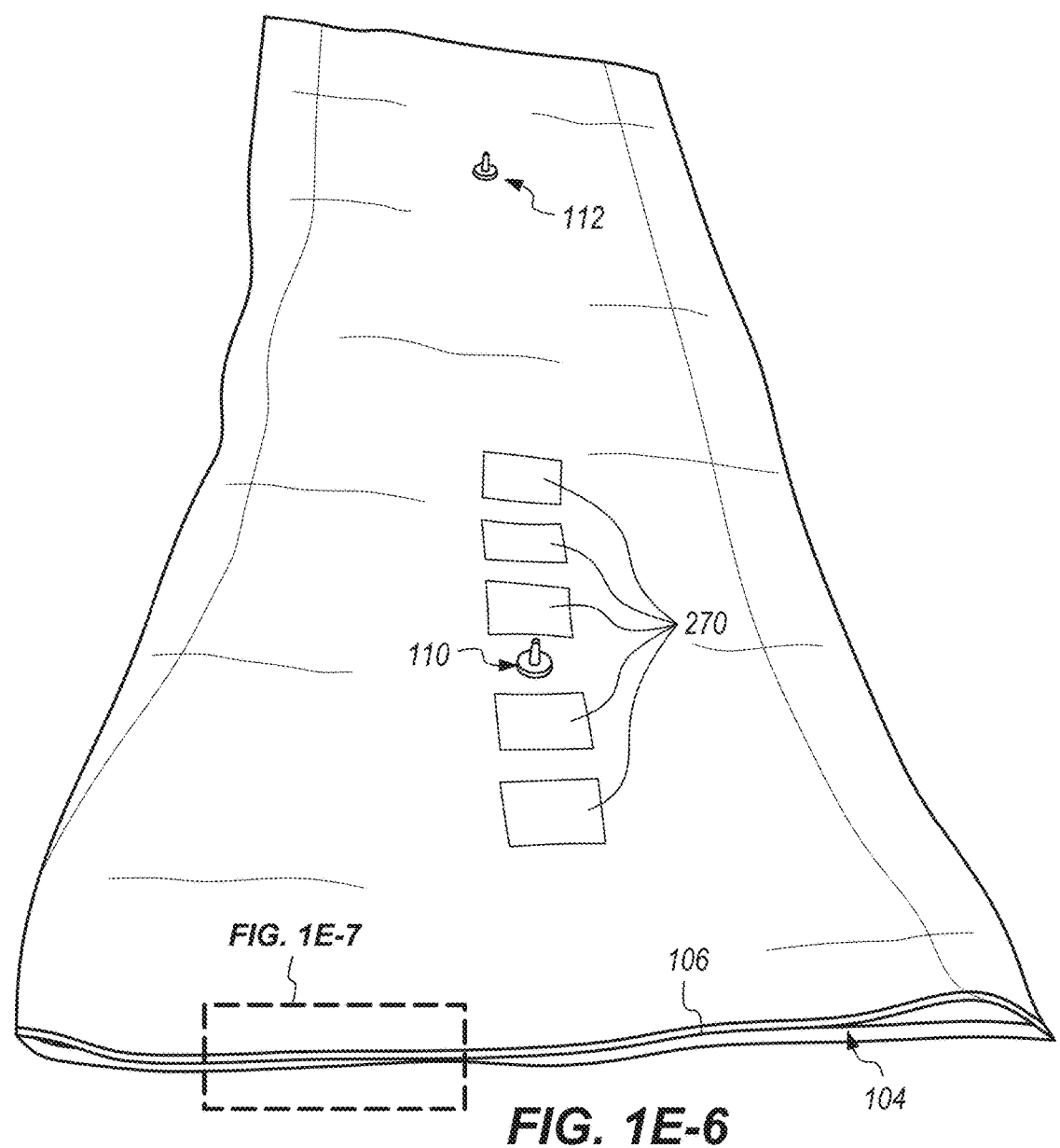
Figures 1, 1E, 2, 3, 4, 5, 6, 7:
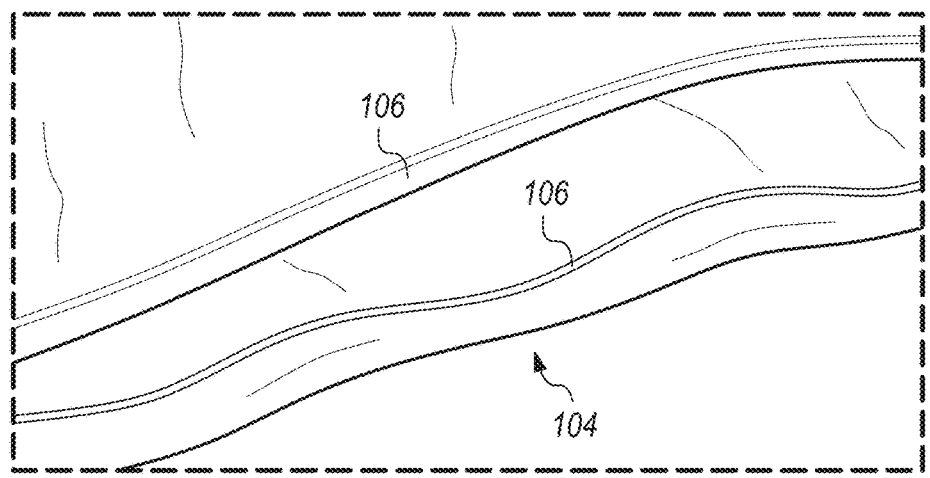
Figures 1, 1E, 2, 3, 4, 5, 6, 7, 8, 9, 10:
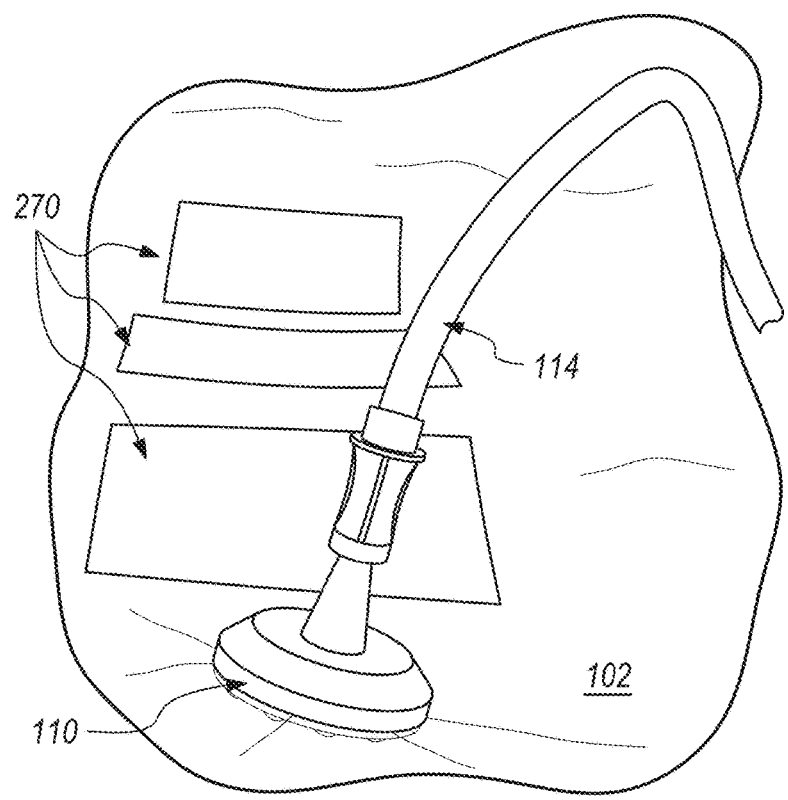
Figures 1, 1E, 2, 3, 4, 5, 6, 7, 8, 9, 10, 11:
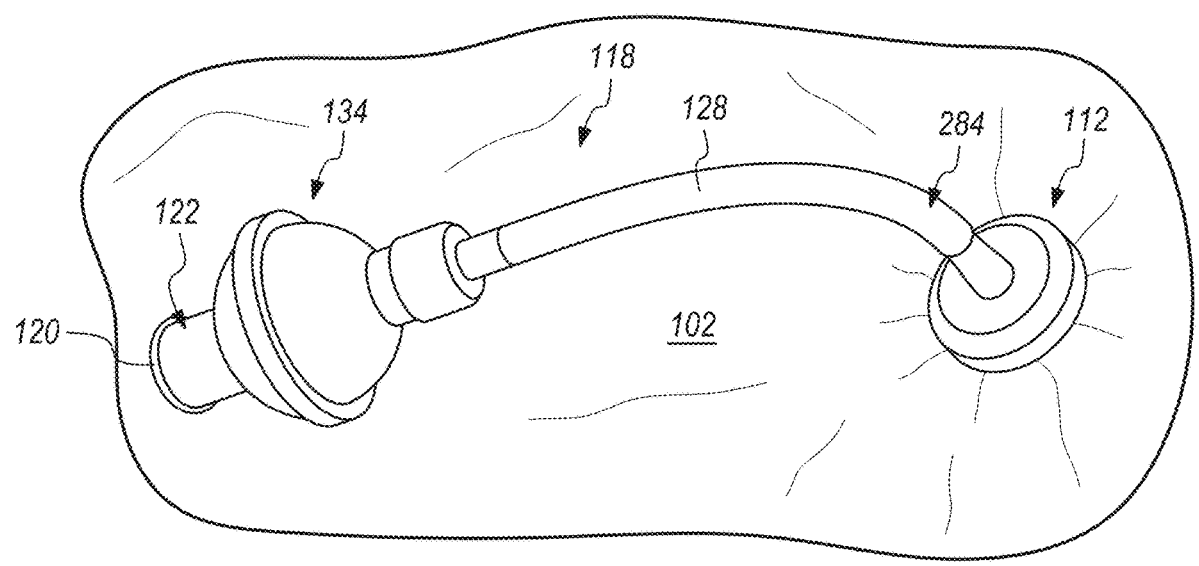

Referring to FIGS. 4A to 4B-5, a linear seal member 106 is associated with single access opening 104 that when closed, seals off the internal chamber of the polyethylene membrane 102. Seal member 106 is position parallel along a transverse axis 130 of the polyethylene membrane 102. The orientation of seal member 106 along shorter transverse axis 130 is important in that potential of any leakage (if any) is minimized due to the shorter distance required to actually close-off the seal member 102.

Seal member 106 may comprise of any mechanism that properly seals off the polyethylene membrane 102. Proper sealing in accordance with one or more embodiments of the present invention may be defined as a seal that may withstand (i.e., maintain seal) at 100 Pa internal pressure. Non-limiting, non-exhaustive examples of mechanisms that may be used as a seal member may include most well-known sealing zippers, or others such Ziploc® bag type zippers, adhesive strip, etc. It would be possible but less desirable to use an adhesive strip instead of the zipper. Of course, use of zippers is preferred in that they may be opened and resealed while an adhesive strip would likely be single use.

The material used for seal member 106 (including all components that constitute isolation system 100) must be compatible with the use of medical grade oxygen. In other words, the use of the combination of the medical grade oxygen and the material of the seal member 106 (and in fact, isolation system 100) used should not result in off-gassing harmful chemicals that may be detrimental to patient 108 sealed within the polyethylene membrane 102. Non-limiting example of a material that may be used for seal member 106 may comprise of polyethylene (the same as the polyethylene membrane 102).

Seal member 106 may comprise of a heavy duty, single track zipper type (Ziploc® zipper type) sealer with colored (e.g., red) visual indicator 160 (FIG. 4B-1) that shows a proper closure of seal member 106. Seal member 106 may comprise one of a 3-bead sealer and 6 bead sealer, and is fully compatible for use with polyethylene and medical grade oxygen.

Seal member 106 may be applied to the polyethylene membrane 102 using well known processes, non-limiting example of which may include application of heat and an impulse, pressurized seal of seal member 106 to polyethylene membrane 102, resulting in an integral, unitized construct. More particularly, seal member 106 may be thermally welded to membrane 102.

Referring back to FIG. 4A, first port 110 and second port 112 may be identical and form an integral unitized construct with the polyethylene membrane 102. A first location of a first position of first port 110 in relation to thermally sealed lateral sides 138 and 140 and single access opening 104 is identical to a second location of a second position of second port 112 in relation to thermally sealed lateral sides 138 and 140 and thermally sealed end 142.

The first location of the first position of first port 110 is defined by a first distance 156 oriented parallel central longitudinal axis 144 of the polyethylene membrane 102 from first port 110 to single access opening 104, and a second distance 158 oriented parallel transverse axis 130 of the polyethylene membrane 102 from first port 110 to one of the thermally sealed lateral sides (138 or 140). The distance 158 from first port 110 to both thermally sealed either lateral sides 138 and 140 is identical and hence, first port 110 is positioned on central longitudinal axis 144 of the polyethylene membrane 102.

The second location of the second position of second port 112 is defined by the same distance value 156, from second port 112 to thermally sealed end 142, and a second distance 158 oriented parallel transverse axis 130 of the polyethylene membrane 102 from second port 112 to one of the thermally sealed lateral sides (138 or 140).

Non-limiting examples of distance 156 may be about 61 cm and that of distance 158 about 48.3 cm. The critical and advantageous reasons for equal distances 156 and 158 for both first and second ports 110 and 112 is that, as detailed above, such an arrangement allows patient 108 to be moved into isolation within polyethylene membrane 102 head first or feet first, where in both instances, one of the first and second ports 110 or 112 will always be near the head of patient 108 (which will be used as the inflow or inlet port).

FIGS. 4C to 4V are non-limiting, exemplary illustrations of first and second ports shown in FIGS. 1A to 4B-5 in accordance with one or more embodiments of the present invention. As illustrated in FIGS. 1A to 4V, first and the second ports 110 and 112 are comprised of a first piece 160 and a second piece 162 for interlocking first piece 160 with the polyethylene membrane 102.

As best illustrated in FIGS. 4E, 4G, and 4H to 4K, a non-limiting, exemplary method of installing first and second ports 110 and 112 is to poke a through-opening 166 (FIG. 4H) on a mounting location 168 of the polyethylene membrane 102, with the polyethylene membrane through-opening 166 having sufficient diameter to only allow projection 206 of first piece 160 to pass through.

Projection 206 of first piece 160 is inserted passed through opening 166 from an interior side 170 (FIG. 4E) of mounting location 168 of the polyethylene membrane 102. Thereafter, mounting opening 180 of second piece 162 is aligned and positioned over top edge 182 of barb section 164 (hose barb 282) of projection 206 and moved (shown by arrows 184) and pressed down to be interlocked with first piece 160, with mounting location 168 of the polyethylene membrane 102 caught and securely fixed in between first and second pieces 160 and 162. Second piece 162 interference-fits onto first piece 160, thus fixing and sealing through-opening 166 of the polyethylene membrane 102 in between first and second pieces 160 and 162 without any thermal welding. It should be noted that inner diameter 216 (FIG. 4H) of mounting opening 180 of second piece 162 is smaller than outer diameter 218 of interlocking projection 210 of projection 206, resulting in interference fit interlocking of second piece 162 with first piece 160.

First piece 160 has an annular construction with through opening (shown by arrow 290 in FIG. 4G). Projection 206 (FIG. 4H) includes a part of through-opening 290 protrudes perpendicular from a base 176 of first piece 160.

Projection 206 includes an upper portion 164 that defines hose barb 282 of first piece 160, a lower portion 172 that defines an interlocking projection 210 for interference fit of second piece 162 with first piece 160, and a relief 174 for fixing second piece 162 in interlocked position in relation to first piece 160.

Base 176 includes a top side with radially extending beveled lateral surface 178, forming an annular frustum of right circular cone. Radial beveled lateral surface 178 facilitates to evenly spread-out mounting side 168 of the polyethylene membrane 102 around and away from the port, thus preventing potential kinking of the polyethylene membrane 102 when installing or mounting first or second ports 110 and 112.

As best illustrated in FIGS. 4P and 4Q, radially extending beveled lateral surface 178 includes a top portion 186 with a vertical drop 208 that leads to a beveled portion 188, and a bottom portion 220 that defines a horizontal portion 190. The structure of the radially extending beveled lateral surface 178 is complementary to bottom side structure 222 (FIGS. 4R and 4U) of second piece 162.

A bottom side 194 of first piece 160 includes circumferentially positioned protuberances 196 that function to substantially uniformly direct and distribute (more efficiently disburse) incoming medical grade oxygen or air shown by arrows 198 (FIGS. 4E and 4M) from opening 290 of first piece 162 into the internal chamber of the polyethylene membrane 102 and substantially uniformly direct and exhaust out exhaust air (shown by arrows 202) from the internal chamber of the polyethylene membrane 102 and into opening 290. Simply stated, protuberances 196 aid in providing laminar inflows 198 and laminar outflows 202.

Given the flexible nature of the polyethylene membrane 102, protuberances 196 also function to prevent the polyethylene membrane 102 to choke-off through-opening 290 when one of the first or second ports (110 or 112) is used as an outlet or exhaust port. That is, as exhaust is pushed out by incoming inflows 198 via through-opening 290, the force may potentially flex the polyethylene membrane 102 where it may "cave-in" or "collect" towards through-opening 290 of the exhaust port, potentially causing a choked-flow effect.

As best shown in FIGS. 4P and 4Q, protuberances 196 have sufficient bulk to provide sufficient space 214 in-between to thereby block to prevent the polyethylene membrane 102 to potentially "cave-in" and vacuum seal with bottom flat circumferential edge 212 of first piece 160, thus preventing blocking or choking off of outflows 202 from through-opening 200. Accordingly, both ingress inflows 198 and egress outflows 202 remain substantially laminar, regardless of the movements of patient 108 within the polyethylene membrane 102 or when sealed-off patient 108 is transported.

It should be noted that it is only for the purposes of teaching and discussion that both incoming medical grade oxygen or air inflows 198 and exhaust outflows 202 are both shown simultaneously in relation to the same first piece 160. As detailed above, obviously inflows will be through one port (110 or 112) and outflows through the other (112 or 110).

Referring back to FIG. 4P, as was indicated above, the internal positive pressure $P_{Mem}$ (i.e., the backpressure) within membrane 102 is regulated by the pneumatic resistance to the flow at the outlet interior passage (or tube portion) 292, dictated by diameter 294 and length 296. This pneumatic resistance to flow provides a nominal 50 Pa back pressure within membrane 102 ($P_{Mem}$). This pressure level of about 50 Pa is sufficient to support membrane 102 in an inflated state while minimizing leakage flow (if any). Accordingly, the outlet port (110 or 112) intrinsically functions as a passive pressure regulator.

The outlet port maintains an internal positive pressure $P_{Mem}$ of the membrane 102 at a constant level for a given rate of flow of oxygen or air (e.g., liters per minute) to allow membrane 102 to remain in the expanded (inflated) state. Internal positive pressure $P_{Mem}$ of membrane 102 is maintained as result of a back pressure generated by outlet port (110 or 112).

A pressure difference between interior or internal positive pressure $P_{Mem}$ of membrane 102 and that of an outside ambient pressure $P_{Amb}$ is determined by a pressure drop $\Delta P_{Outlet}$ at outlet port 110 or 112 at a given flow rate, wherein:

$$P_{Mem} - P_{Amb} = \Delta P_{Outlet},$$

with the pressure drop $\Delta P_{Outlet}$ through the outlet port 110/112 generating the back pressure to establish interior positive pressure $P_{Mem}$ of membrane 102 in accordance with:

$$P_{Mem} = \Delta P_{Outlet} + P_{Amb}.$$

As detailed below, outlet port 110 or 112 is a solid non-varying object and therefore, the $\Delta P_{Outlet}$ will be constant at a given flow rate. Further, outlet port functions an intrinsic passive pressure regulation that provides a back pressure (which is the $P_{Mem}$). Accordingly, for a given flow rate, $P_{Mem}$ will most likely also remain constant.

Further, interior positive pressure $P_{Mem}$ is normalized to the outside ambient pressure $P_{Amb}$. It should be noted that the differential pressure $\Delta P_{Outlet}$ will remain the same regardless of the altitude within which the isolation system is used for a give flow rate. Of course, the higher the flow rate, the greater the internal positive pressure $P_{Mem}$.

The pressure differential $\Delta P_{Outlet}$ at the outlet port is a function of the interior geometry of the outlet port 110 or 112 and rate of flow of exhaust gas through the outlet port. The interior geometry of the outlet port is defined by an inner diameter 294 of interior passage (or tube portion) 292 of outlet port, a longitudinal axial length 296 of the interior passage (or tube portion) 292 of the outlet port, and an inner surface roughness of the interior passage (or tube portion) 292 of the outlet port.

The longitudinal axial length 296 of the interior passage (or tube portion) 292 of the outlet port is an elongated, hollow cylinder (with diameter 294) of rigid plastic for transporting exhaust gases. The inner surface roughness coefficient of interior passage (or tube portion) 292 may be readily obtained from well known surface material charts/tables publications that include absolute roughness coefficients for various materials. In fact, it should be noted that all calculations related to fluid pressure drop (e.g., such as for $\Delta P_{Outlet}$) along pipe length of uniform diameter (e.g., such as interior passage (or tube portion) 292) are simple basic fluid dynamics calculations that are very well known.

One or more embodiments of the present invention use a gas flow rate of about 32 liters per minute as part of the calculations for determining $\Delta P_{Outlet}$, which is the flow rate at which the HEPA filter 228 (further detailed below) of the present invention is certified. Filter 228 is certified to have the filtering efficiencies provided by the manufacturer for all flow rates up to 32 liters per minute. It should also be noted that any pressure drop across the HEPA filter 228 at a flow rate of 32 liters per minute is insignificant and in fact, negligible. In fact, it is a very small fraction of the overall pressure drop $\Delta P_{Outlet}$. The pressure drop $\Delta P_{Outlet}$ in Pascal across the outlet port 110 or 112 as a function of the flow rate of exhaust gas (liters per minute) through the interior passage (or tube portion) 292 of outlet port 110 or 112 is summarized in the chart of FIG. 4V.

As is well known to those skilled in the art, as the Reynolds number is increased (due to the Velocity V of the exhaust gas through the outlet port 110 or 112), the exhaust gas flows through the outlet port move from the desired laminar flow conditions to a complete turbulent flow condition. The generated turbulent flow conditions within outlet port tube or pipe 292 would tend to hinder flow of exhaust gas, resulting in greater and greater back pressure (also known as "choked flow") at the outlet port, which would result in greater and greater internal positive pressure $P_{Mem}$.

Maximum flow rate for the filter is 32 liters per minute as indicated above. Accordingly, even at such a high flow rate of 32 liters per minute, the generated internal pressure of the membrane $P_{Mem}$ (of about 500 to 600 Pa) will not affect the structural integrity of membrane 102 nor the flow capacity of the filter.

As further shown in FIG. 4V, at 10 liters per minute $\Delta P_{Outlet}$ (which is also the backpressure or $P_{Mem}$) is about 50 Pa. Obviously, the greater the flow rate, the higher the internal pressure of the membrane $P_{Mem}$. It is preferred to maintain $P_{Mem}$ as low as possible (e.g., 50 Pa) to simply maintain membrane 102 at its expanded inflated state, away from contacting the subject body fully isolated inside membrane 102. Further, if there are any unintended openings (e.g., accidental puncture, for example, a small pin-hole sized opening at some section of membrane 102), the leakage flow rate at the pin hole sized opening (if any) would be insignificant and in fact, negligible due to the very low internal positive pressure $P_{Mem}$ (e.g., 50 Pa) of membrane 102, thus membrane 102 would continue to encapsulate and isolate the subject inside even with a small (e.g., pin sized) puncture hole.

Accordingly, outlet port 110 or 112 indeed functions as a passive pressure regulator for a given flow rate. It should be noted that the flow rate throughout the system is the same. That is, the flow rate of gas at the inlet port, the membrane, and outlet port are all equal. Further, the pressure drop at the inlet port $\Delta P_{Inlet}$ from the oxygen source into the member is not relevant for outlet port pressure drop calculations as the $\Delta P_{Outlet}$ is determined based on the flow rate at the outlet port and not pressure drop $\Delta P_{Inlet}$.

It should be noted that modifying or changing the size or dimensions of the outlet port is possible so long as the isolation intent of the membrane is not compromised.

In summary, a pressure differential $\Delta P_{Outlet}$ generates a back pressure within membrane 102 that enables membrane 102 to remain in the expanded or inflated state at a pressure ($P_{Mem}$). The outlet port generates the back pressure that leads to a pressure drop through the outlet port $\Delta P_{Outlet}$, while maintaining the interior positive pressure of the membrane $P_{Mem}$ constant at a given flow rate. Further, low interior positive pressures of about 50 Pa are critical and advantageous in that such pressures continue to maintain membrane 102 in the expanded (inflated) state while allowing for application of unintentional or unintended external pressures. That is, even at its expanded (inflated) state, a person may easily compress or push into the membrane from outside and press it inward without much affect to the overall operation of the membrane. In other words, the low pressure $P_{Mem}$ does not expand the membrane to be too taut to a point where if it comes into contact with a sharp object it may puncture (similar to puncturing a balloon with a pin).

Use of low interior positive pressures $P_{Mem}$ is further critical and advantageous because low interior positive pressures $P_{Mem}$ reduce a potential for leakage of exhaust gas from within the membrane. In fact, the interior positive pressures $P_{Mem}$ at 50 Pa is so low that even if there is a leak, the leaked exhaust gas would be insignificant.

FIGS. 5A-1 to 5I-3 are non-limiting, exemplary illustrations of an exhaust filter assembly shown in FIGS. 1A to 4V in accordance with one or more embodiments of the present invention. As illustrated in FIGS. 5A-1 to 5I-3, exhaust filter assembly 118 (fully compatible with use with medical grade oxygen) is comprised of a well-known filter sub-assembly 224 that includes a well-known filter housing 226 with a well-known filter 228. It is preferred if filter 228 is comprised of a Hight-Efficiency Particulate Air (HEPA) filter and more particularly, any HEPA filter 228 greater than HEPA class E12/H12 (based on European standard). In fact, present invention most preferably uses HEPA class U15 HEPA filters. In particular, exhaust gas filter assembly 118 may be a high flow, low pressure differential HEPA filter, certified to remove 99.99% of viral and 99.999% bacterial contamination.

Exhaust filter assembly 118 further includes a filter connector assembly 230 to connect exhaust filter subassembly 224 to the polyethylene membrane 102, and also includes filter protective output plug 120.

Filter connector assembly 230 is comprised of a medical grade oxygen rated outflow tubing 128 (identical to inflow tube 114), including a barb 232 that receives down-stream end 234 of the medical grade oxygen rated outflow tubing 128. Further included is an adapter-cap 236 that allows mounting and sealing of barb 232 to filter subassembly 224.

Barb 232 is secured with adapter-cap 236 by a washer 238 and a nut 240 via a top opening 242 of adapter-cap 236. Adapter-cap 236 is an annular piece with a smaller diameter top opening 242 to receive threaded end 244 of barb 232, and a larger diameter bottom opening 246 for mounting onto and over upstream end 248 of filter subassembly 224. As best illustrated in FIGS. 4I-1 to 4I-4, filter assembly plug 120 is configured to plug into downstream end 250 of filter subassembly 224.

It should be noted that filter 228 does not impede the flow rate of exhaust gas via the outlet port and thus, the rate of outflow of exhaust gas via the outlet port is equal to the rate of inflow of oxygen via the inlet port, while the internal positive pressure of membrane 102 remains constant for a given flow rate.

Although the invention has been described in considerable detail in language specific to structural features (e.g., measurements, etc.) and or method acts, it is to be understood that the invention defined in the appended claims (if any) is not necessarily limited to the specific features or acts described. Rather, the specific features and acts are disclosed as exemplary preferred forms of implementing the claimed invention. Stated otherwise, it is to be understood that the phraseology and terminology employed herein, as well as the abstract, are for the purpose of description and should not be regarded as limiting. Further, the specification is not confined to the disclosed embodiments. Therefore, while exemplary illustrative embodiments of the invention have been described, numerous variations and alternative embodiments will occur to those skilled in the art. For example, Because the isolation system is intended for operation with either medical grade oxygen or compressed air, all components, including the polyethylene membrane, and the exhaust filter assembly must be medical grade oxygen compatible. Additionally, a one-to-one correspondence between isolation system 100 and a source of oxygen, air, or air enriched with oxygen should not be assumed. For example, a single canister of oxygen may be used to simultaneously supply oxygen to multiple separate isolation systems 100 using any well-known oxygen flowmeter tee-branch or other well known adapter connectors. Such variations and alternate embodiments are contemplated, and can be made without departing from the spirit and scope of the invention.

It should further be noted that throughout the entire disclosure, the labels such as left, right, front, back, top, inside, outside, bottom, forward, reverse, clockwise, counter clockwise, up, down, or other similar terms such as upper, lower, aft, fore, vertical, horizontal, lateral, oblique, proximal, distal, parallel, perpendicular, transverse, longitudinal, etc. have been used for convenience purposes only and are not intended to imply any particular fixed direction, orientation, or position. Instead, they are used to reflect relative locations/positions and/or directions/orientations between various portions of an object.

In addition, reference to "first," "second," "third," and etc. members throughout the disclosure (and in particular, claims) is not used to show a serial or numerical limitation but instead is used to distinguish or identify the various members of the group.

Further the terms "a" and "an" throughout the disclosure (and in particular, claims) do not denote a limitation of quantity, but rather denote the presence of at least one of the referenced item.

The use of the phrases "and or," "and/or" throughout the specification (if any used) indicate an inclusive "or" where for example, A and or B should be interpreted as "A," "B," or both "A and B."

In addition, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of," "act of," "operation of," or "operational act of" in the claims herein is not intended to invoke the provisions of 35 U.S.C. 112, Paragraph 6.

What is claimed is:

1. An isolation system, comprising:
a flexible, portable, disposable membrane with no support structures comprised of a medical grade polymer;
the membrane expands from a contracted state for storage to an expanded state for use;
the membrane in the expanded state has an internal positive pressure, forming a chamber with an opening on one side only;
the opening has a sealing member that when closed, seals off the chamber;
the membrane includes:
an inlet port for ingress of oxygen, compressed air, or air enriched with oxygen into the chamber; and
an outlet port for egress of exhaust gases through a detachably connected exhaust filter assembly, with the outlet port intrinsically functioning as a passive positive pressure regulator.

2. The isolation system as set forth in claim 1, wherein:
the outlet port maintains the internal positive pressure of the membrane ($P_{Mem}$) at a constant level for a given rate of flow of oxygen to allow the membrane to remain in the expanded state.

3. The isolation system as set forth in claim 2, wherein:
the internal positive pressure of the membrane ($P_{Mem}$) is maintained as a result of a back pressure at the outlet port.

4. The isolation device as set forth in claim 3, wherein:
a pressure difference between the interior positive pressure of the membrane PMem and that of an outside ambient pressure $P_{Amb}$ is determined by a pressure drop at the outlet port $\Delta P_{Outlet}$ at a given flow rate, wherein:

$$P_{Mem} - P_{Amb} = \Delta P_{Outlet},$$

with the pressure drop through the outlet port $\Delta P_{Outlet}$ generating the back pressure to establish the interior positive pressure of the membrane $P_{Mem}$ in accordance with:

$$P_{Mem} = \Delta P_{Outlet} + P_{Amb}.$$

5. The isolation device as set forth in claim 4, wherein:
the pressure differential at the outlet port $\Delta P_{Outlet}$ is a function of an interior geometry of the outlet port and a rate of flow of exhaust gas through the outlet port; wherein:
the interior geometry of the outlet port is defined by an inner diameter of the outlet port, a longitudinal axial length of a tube portion of the outlet port, and an inner surface roughness of the outlet port.

6. The isolation device as set forth in claim 2, wherein:
a pressure differential APOutlet generating a back pressure enables the membrane to remain in the expanded state.

7. The isolation device as set forth in claim 2, wherein:
the outlet port generates a back pressure that leads to a pressure drop through the outlet port $\Delta P_{Outlet}$, while maintaining the interior positive pressure of the membrane $P_{Mem}$ constant at a given flow rate.

8. The isolation device as set forth in claim 1, wherein:
the exhaust filter assembly includes:
a filter that prevents pathogens from exiting the chamber and into an outside environment, thereby preventing cross-contamination of the outside environment.

9. The isolation device as set forth in claim 8, wherein:
the filter is a High-Efficiency Particulate absorbing (HEPA) filter.

10. The isolation device as set forth in claim 8, wherein:
the filter does not impede a flow rate of exhaust gas via the outlet port and thus, the flow rate of outflow of exhaust gas via the outlet port is equal to a rate of inflow of oxygen via the inlet port, while an internal positive pressure of the membrane remains constant for a given flow rate.

11. The isolation system as set forth in claim 1, wherein:
the sealing member is oriented along a transverse axis of the membrane, minimizing a potential of leakage.

12. The isolation system as set forth in claim 1, wherein:
the membrane has sufficient size and is adapted to completely encompass and completely encapsulate a subject.

13. The isolation system as set forth in claim 12, wherein:
the membrane is configured for enclosure of the subject within the membrane head first or feet first.

14. The isolation system as set forth in claim 1, wherein:
the expanded state of the chamber is maintained at an overall minimum membrane circumference by the internal positive pressure.

15. The isolation device as set forth in claim 1, wherein:
the sealing member is positioned along a transverse axis of the membrane;
the position of the sealing member along a shorter transverse axis compared with a longer longitudinal axis of the membrane minimizes potential of leakage.

16. The isolation device as set forth in claim 1, wherein:
the inlet port of the membrane is adapted to be near a subject's head, and the outlet port of the membrane is adapated to be near the subject's feet.

17. The isolation device as set forth in claim 1, wherein:
the exhaust filter assembly is comprised of:
a cap that prevents exhaust of internal gas from the membrane thereby quickly inflating the membrane.

18. The isolation device as set forth in claim 1, wherein:
the exhaust filter assembly is comprised of a High-efficiency Particulate Air absorbing (HEPA) filter.

19. An isolation system, comprising:
a flexible, portable, disposable membrane with no support structures;
the membrane expands from a contracted state for storage to an expanded state for use;
the membrane in the expanded state has an internal positive pressure, forming a chamber with an opening on one side only;
the opening has a sealing member that when closed, seals off the chamber;
the membrane includes:
an inlet port for ingress of gas into the chamber;
the inlet port is adapted to be near a head of a subject; and
an outlet port for egress of exhaust gases through a detachably connected exhaust filter assembly, with the outlet port adapted to be near the feet of the subject, with the outlet port intrinsically functioning as a passive positive pressure regulator.

20. The isolation system as set forth in claim 19, wherein:
the inlet port and the outlet port are identical and interchangeable.

21. The isolation system as set forth in claim 19, wherein:
the membrane is comprised of a medical grade polyethylene.

22. A method for isolation, comprising:
providing a disposable isolation kit;
unfurling a membrane of the disposable isolation kit;
surrounding a subject within the membrane;
laying the subject prone while within the membrane;
aligning a first port and a second port of the membrane to lie approximate on a frontal midplane of the subject, with the first port near the subject head and the second port near the subject feet;
connecting gas tubing to the first port of the membrane;
connecting an exhaust filter assembly to the second port of the membrane;
delivering medical grade oxygen, air, or air enriched with oxygen into the membrane at a rate regulated to control internal positive pressure of the membrane to maintain the membrane in the expanded state;
sealing an open end of the membrane;
maintaining visual observation to assure inflow of continuous unabated medical grade oxygen, air, or air enriched with oxygen.

* * * * *